US006294655B1

(12) United States Patent
Ford et al.

(10) Patent No.: US 6,294,655 B1
(45) Date of Patent: Sep. 25, 2001

(54) ANTI-INTERLEUKIN-1 RECEPTOR ANTAGONIST ANTIBODIES AND USES THEREOF

(75) Inventors: John Ford, San Mateo; Ann Pace, Scotts Valley, both of CA (US)

(73) Assignee: Hyseq, Inc., Sunnyvale, CA (US)

( * ) Notice: Subject to any disclaimer, the term of this patent is extended or adjusted under 35 U.S.C. 154(b) by 0 days.

(21) Appl. No.: 09/417,455

(22) Filed: Oct. 13, 1999

Related U.S. Application Data

(63) Continuation-in-part of application No. 09/348,942, filed on Jul. 7, 1999, which is a continuation of application No. 09/287,210, filed on Apr. 5, 1999, now abandoned, which is a continuation-in-part of application No. 09/251,370, filed on Feb. 17, 1999, now abandoned, which is a continuation-in-part of application No. 09/127,698, filed on Jul. 31, 1998, now abandoned, and a continuation-in-part of application No. 09/229,591, filed on Jan. 13, 1999, now abandoned, which is a continuation of application No. 09/099,818, filed on Jun. 19, 1998, now abandoned, said application No. 09/127,698, is a continuation-in-part of application No. 09/082,364, filed on May 20, 1998, now abandoned, said application No. 09/099,818, is a continuation-in-part of application No. 09/082,364, filed on May 20, 1998, now abandoned, which is a continuation-in-part of application No. 09/079,909, filed on May 15, 1998, now abandoned, which is a continuation-in-part of application No. 09/055,010, filed on Apr. 3, 1998, now abandoned.

(51) Int. Cl.$^7$ .............................. C07K 16/18; C12P 21/08

(52) U.S. Cl. ................................ 530/388.23; 530/387.9; 530/388.1; 530/388.15; 530/389.1; 530/391.1; 530/391.3; 530/350; 536/23.5; 436/501; 435/7.1; 424/134.1; 424/139.1; 424/141.1; 424/145.1

(58) Field of Search .............................. 435/69.1, 69.7, 435/7.1; 536/23.5, 23.53; 436/501; 424/134.1, 139.1, 141.1, 145.1; 530/387.9, 388.1, 388.15, 388.23, 389.1, 391.1, 391.3, 350

(56) References Cited

U.S. PATENT DOCUMENTS

| | | | |
|---|---|---|---|
| 4,235,871 | 11/1980 | Papahadjopoulos et al. | 424/19 |
| 4,439,196 | 3/1984 | Higuchi | 604/890 |
| 4,447,224 | 5/1984 | DeCant, Jr. et al. | 604/67 |
| 4,447,233 | 5/1984 | Mayfield | 604/152 |
| 4,475,196 | 10/1984 | La Zor | 371/29 |
| 4,486,194 | 12/1984 | Ferrara | 604/897 |
| 4,487,603 | 12/1984 | Harris | 604/152 |
| 4,501,728 | 2/1985 | Geho et al. | 424/38 |
| 4,518,584 | 5/1985 | Mark et al. | 424/85 |
| 4,683,195 | 7/1987 | Mullis et al. | 435/6 |
| 4,737,323 | 4/1988 | Martin et al. | 264/4.3 |
| 4,798,885 | 1/1989 | Mason et al. | 530/350 |
| 4,837,028 | 6/1989 | Allen | 424/450 |
| 4,946,778 | 8/1990 | Ladner et al. | 435/69.6 |
| 4,965,188 | 10/1990 | Mullis et al. | 435/6 |
| 5,202,231 | 4/1993 | Drmanac et al. | 435/6 |
| 5,272,071 | 12/1993 | Chappel | 435/172.3 |
| 5,334,380 | 8/1994 | Kilbourn et al. | 424/85.2 |
| 5,413,778 | 5/1995 | Kunkel et al. | 424/1.41 |
| 5,508,262 | 4/1996 | Norman, Jr. | 514/8 |
| 5,525,464 | 6/1996 | Drmanac et al. | 435/6 |
| 5,578,461 | 11/1996 | Sherwin et al. | 435/69.1 |

FOREIGN PATENT DOCUMENTS

| | | |
|---|---|---|
| 0 343 684 A | 11/1989 | (EP) . |
| 90/03382 | 4/1990 | (WO) . |
| 90/14148 | 11/1990 | (WO) . |
| 91/06667 | 5/1991 | (WO) . |
| 91/07491 | 5/1991 | (WO) . |
| 91/09955 | 7/1991 | (WO) . |
| 91/17249 | 11/1991 | (WO) . |
| 92/20808 | 11/1992 | (WO) . |
| 93/09222 | 5/1993 | (WO) . |
| 94/12650 | 6/1994 | (WO) . |
| 95/05846 | 3/1995 | (WO) . |
| 95/09248 | 4/1995 | (WO) . |
| 95/16035 | 6/1995 | (WO) . |
| 98/47921 | 10/1998 | (WO) . |
| 99/35268 | 7/1999 | (WO) . |

OTHER PUBLICATIONS

Adelman, J. et al., "In Vitro Deletional Mutagenesis for Bacterial Production of the 20,000–Dalton Form of Human Pituitary Growth Hormone," *DNA*, 2:183–193 (1983).

Altschul S.F. et al., "Basic Local Alignment Search Tool," *J. Mol. Biol.*, 215:403–410 (1990).

Altschul, S.F., "A Protein Alignment Scoring System Sensitive to All Evolutionary Distances," *J. Mol. Evol*, 36:290–300 (1993).

Anderson, W.F., "Human Gene Therapy," *Nature (Supp.)*, 392 (6679):25–30 (1998).

Antica, M. et al ., "Thymic Stem Cell in Mouse Bone Marrow," *Blood* 84:111–117 (1994).

Arakawa, Y. et al., "Survival Effect of Ciliary Neurotrophic Factor (CNTF) on Chick Embryonic Motoneurons in Culture: Comparison with Other Neurotrophic Factors and Cytokines," *J. Neuroscience*, 10:3507–3515 (Nov., 1990).

Arend, W.P. et al., "Effects of Immune Complexes on Production By Human Monocytes of Interleukin 1 or an Interleukin 1 Inhibitor," *J. Immunol.*, 134:3868–3875 (Jun., 1985).

Arend, W.P. et al., "Interleukin–1 Receptor Antagonist: Role in Biology," Annu. Rev. Immunol., 16:27–55 (1998).

(List continued on next page.)

*Primary Examiner*—Lorraine Spector
(74) *Attorney, Agent, or Firm*—Marshall, O'Toole Gerstein, Murray & Borun

(57) ABSTRACT

The present invention provides novel nucleic acids, the novel polypeptide sequences encoded by these nucleic acids and uses thereof. These novel polynucleotide and polypeptide sequences were determined to be a novel Interleukin-1 Receptor Antagonist. Also provided are antibodies which bind the antagonist, methods of detecting the antagonist, and kits containing the antibodies.

14 Claims, 14 Drawing Sheets

OTHER PUBLICATIONS

Asseline U. et al., "Nucleic Acid–Binding Molecules with High Affinity and Base Sequence Specificity: Intercalating Agents Covalently Linked to Oligodeoxynucleotides," *Proc. Natl. Acad. Sci.*, 81:3297–3301 (1984).

Bakouche, O. et al., "Subcellular Localization of Human Monocyte Interleukin–1: Evidence for an Inactive Precursor Molecule and a Possible Mechanism For IL 1 Release," *J. Immunol.*, 138:4249–4255 (Jun., 1987).

Bayer, E.A. et al., "The Avidin–Biotin Complex in Affinity Cytochemistry," *Meth. Enzym.*, 62:308–315 (1979).

Beal et al., "Second Structural Motif for Recognition of DNA by Oligonucleotide–Directed Triple–Helix Formation," *Science*, 251:1360–1363 (Mar., 1991).

Beg, A. et al., "Tumor Necrosis Factor and Interleukin–1 Lead to Phosphorylation and Loss of IκBα: a Mechanism for NF–κB Activation," *Mol. Cell. Biol.*, 13:3301–3310 (Jun., 1993).

Bertagnolli, M. et al., "IL–12 Augments Antigen–Dependent Proliferation of Activated T Lymphocytes," *J. Immunol.*, 149:3778–3783 (Dec., 1992).

Bertagnolli, M. et al., "IL–4–Supported Induction of Cytolytic T Lymphocytes Requires IL–2 and IL–6," *Cell Immunol.*, 133:327–341 (1991).

Bertagnolli, M. et al., "IL–7 Supports the Generation of Cytotyoxic T Lymphocytes From Thymocytes," *J. Immunol.* 145:1706–1712 (Sep., 1990).

Bevilaqua, M., "Recombinant tumor necrosis factor induces procoagulant activity in cultured human vascular endothelium: Characterization and comparison with the actions of interleukin 1," *Proc. Natl. Acad. Sci.*, 83:4533–4537 (Jun., 1986).

Bhardwaj, N. et al., "Influenza Virus–infected Dendritic Cells Stimulate Strong Proliferative and Cytolytic Responses from Human CD8+ T Cells," *J. Clin. Investigation*, 94:797–807 (Aug., 1994).

Bierer, B. et al., "Synergistic T Cell Activation Via the Physiological Ligands for CD2 and the T Cell Receptor," *J. Exp. Med.*, 168:1145–1156 (Sep., 1988).

Bonaldo M. et al., "Normalization and Subtraction: Two Approaches to Facilitate Gene Discovery," *Genome Res.*, 6:791–806 (1996).

Boorstein, W. et al., "Primer Extension Analysis of RNA," *Methods Enzymol.*, 180:347–369 (1989).

Bowman, M. et al., "Possible Mechanisms by Which the H–2K$^{bm3}$ Mutation May Decrease Cytotoxic T–Lymphocyte Recognition of Vesicular Stomatitis Virus Nucleoprotein Antigen," *J. Virology*, 61:1992–1998 (Jun., 1987).

Bowman, M. et al., "The Cloning of CD70 and Its Identification as the Ligand for CD27," *J. Immunol.*, 152:1756–1761 (1994).

Bresslauer K.J. et al., "Predicting DNA Duplex Stability from the Base Sequence," *Proc. Natl. Acad. Sci., USA*, 83:3746–3750 (1986).

Broude, N.E. et al., "Enhanced DNA Sequencing by Hybridization," *Proc. Natl. Acad. Sci., USA*, 91: 3072–3076 (1994).

Brown, E. et al., "Characterization of Peptide Binding to the Murine MHC Class I H–sK$^k$ Molecule," *J. Immunol.*, 153:3079–3092 (1994).

Brown, M. et al., "Motor Nerve Sprouting," *Ann. Rev. Neurosci.*, 4:17–42 (1981).

Brumbaugh J.A. et al., "Continuous, On–line DNA Sequencing Using Oligodeoxynucleotide Primers with Multiple Fluorophores," *Proc. Natl. Acad. Sci., USA*, 85:5610–5614 (1988).

Burdick, M. et al., "Human Protein C Induces Anticoagulation and Increased Fibrinolytic Activity in the Cat," *Thrombosis Res.* 45:413–419 (1987).

Carter et al., "Purification, cloning, expression and biological characterization of an interleukin–1 receptor antagonist protein," *Nature*, 344:633–638 (1990).

Cate R.L. et al. "Genomic Southern Analysis with Alkaline–Phosphate–Conjugated Oligonucleotide Probes and the Chemiluminescent Substrate AMPPD," *Genet. Anal. Tech. Appl.*, 8(3):102–106 (1991).

Cavender, D. et al., "Superinduction of T Lymphocyte–Endothelial Cell (EC) Binding by Treatment of EC with Interleukin 1 and Protein Synthesis Inhibitors," *J. Immunol.*, 138:2149–2154 (Apr., 1987).

Cole, S.P.C. et al., "The EBV–Hybridoma Technique and It's Application to Human Lung Cancer," *Monoclonal Antibodies and Cancer Therapy*, Alan R. Liss, Inc., pp. 77–96 (1985).

Coligan, J.E et al. (eds.), In: *Current Protocols in Immunology*, vol. 1, pp. 3.1.1–3.1.5, 3.8.1–3.8.16, 3–12.1–3.12.14, 6.3.1–6.3.12, 6.6.1.–6.6.5, 6.8.1–6.8.8, 6.12.1–6.12.28, 6.13.1, 6.15.1, 7.28.1–7.28.22, John Wiley and Sons, Inc. (1991–1994 and 1994–1998).

Collins, T. et al., "A Common Theme in Endothelial Activation" Trends Cardiovasc. Med., 3:92–97 (1993).

Cooney, M. et al., "Site–Specific Oligonucleotide Binding Represses Transcription of the Human c–myc Gene in Vitro," *Science*, 241:456–459 (1988).

Craig, M.E. et al., "Relaxation Kinetics of Dimer Formation by Self Complementary Oligonucleotides," *J. Mol. Biol.*, 62:383–401 (1971).

Dahlén et al., "Sensitive Detection of Genes by Sandwich Hybridization and Time–Resolved Fluorometry," *Mol. Cell. Probes (England)*, 1:159–168 (1987).

Darzynkiewicz, Z. et al., "Features of Apoptotic Cells Measured by Flow Cytometry," *Cytometry*, 13:795–808 (1992).

deVries, P. et al., "The Effect of Recombinant Mast Cell Growth Factor on Purified Murine Hematopoietic Stem Cells," *J. Exp. Med.*, 173:1205–1211 (May, 1991).

Dinarello, C. et al., "The Role of Interleukin–1 in Disease," *N. England J. Med.*, 328:106–113 (Jan., 1993).

Dinarello, C., "Modalities for reducing interleukin 1 activity in disease," *Immunol. Today*, 14:260–264 (1993).

Dinarello, C., "The Interleukin–1 family: 10 years of discovery," *FASEB J.*, :1314–1325 (Dec., 1994).

Dinarello, C.A., "Interleukin–1 and Interleukin–1 Antagonism," *Blood*, 77:1627–1652 (Apr., 1991).

Dolinnaya et al., "Site–directed modification of DNA duplexes by chemical ligation," *Nucleic Acids Research*, (England) 16(9):3721–3738 (May, 1988).

Dolinnaya, N. et al., "The use of BrCN for assembling modified DNA duplexes and DNA–RNA hybrids; comparison with water–soluble carbodiimide," *Nucleic Acids Res.*, 19(11):3067–72 (Jun., 1991).

Drmanac et al., "DNA Sequence Determination of Hybridization: A Strategy for Efficient Large–Scale Sequencing," *Science*, 260:1649–1652 (Jun., 1993).

Drmanac et al., "Reliable hybridization of oligonucleotides as short as six nucleotides," *DNA Cell Biol.*, 9(7):527–534 (Sep., 1990).

Drmanac, R et al., Sequencing of Megabase Plus DNA by Hybridization: Theory of the Method, *Genomics,* 4:114–128 (1989).

Drmanac, R. et al., "A calculation of fragment lengths from human DNA with 78 restriction enzymes: an aid for cloning and mapping," *Nucleic Acids Research,* 14(11): 4691–4692 (1986).

Drmanac, R. et al., "An Algorithm for the DNA Sequence Generation from k–Tuple Word Contents of the Minimal Number of Random Fragments," *J. Biomol. Struct. Syn.,* 8(5):1085–1102 (1991).

Drmanac, R. et al., "DNA Sequence Determination by Hybridization: A Strategy for Efficient Large–Scale Sequencing," *Science,* 260(5114):1649–1652 (1993).

Drmanac, R. et al., "Sequencing By Oligonucleotide Hybridization: A Promising Framework in Decoding of the Genome Program?" Proceedings of the First International Conference Electrophoresis Supercomputing Human Genome, Cantor et al., (Eds.), World Scientific Publishing Co., Singapore, pp. 47–59 (1991).

Drmanac, R. et al., "W (A or T) Sequences as Probes and Primers Suitable for Genomic Mapping and Fingerprinting," *Nucleic Acids Research,* 19(21):5839–5842 (1991).

Drmanac, S. et al., "Processing of cDNA and Genomic Kilobase–Size Clones for Massive Screening, Mapping and Sequence by Hybridization," *Biotechniques,* 17:328–329, 332–336 (1994).

Duncan, C.H. et al., "Affinity Chromatography of a Sequence–Specific DNA Binding Protein using Teflon––linked Oligonucleotides," *Anal Biochem.,* 169:104–108 (1988).

Dvorak, H. et al., "Microvascular Injury in Pathogenesis of Interferon–Induced Necrosis of Subcutaneous Tumors in Mice," *J. Natl. Cancer Institute,* 81:497–502 (Apr., 1989).

Eaglstein, W. et al., "New Method for Assessing Epidermal Wound Healing: the Effects of Triamcinolone Acetonide and Polyethelene Film Occlusion" *J. Invest. Dermatol.,* 71:382–384 (1978).

Eisenberg et al., "Primary Structure and functional expression from complementary DNA of a Human Interleukin–1 receptor antagonist," *Nature,* 343:341–346 (Jan., 1990).

Engvall, E. et al., Enzyme–Linked Immunosorbent Assay, ELISA III. Quantitation of Specific Antibodies by Enzyme––Labeled Anti–Immunoglobulin in Antigen–Coated Tubes, *Immunol.,* 109:129–135 (1972).

Falus, A. et al., "Regulation of IL–6 Receptor and GP130 Expression on Human Cell Lines of Lymphoid and Myeloid Origin," *Cytokine,* 4:495–499 (Nov., 1992).

Fine, J. et al., "Interleukin–10 Enhances γδ T Cell Development in the Murine Fetal Thymus," *Cell. Immunol.,* 155:111–122 (1994).

Fingl et al., in "The Pharmacological Basis of Therapeutics," Ch. 1, p. 1 (1975).

Fischer, E. et al., "Comparison between effects on interleukin–1α administration and sublethal endotoxemia in primates," *Am. J. Physiol.,* 261:R442–R452 (1991).

Forage, R. et al., "Cloning and sequence analysis of cDNA species coding for the two subunits of inhibin from bovine follicular fluid," *Proc. Natl. Acad. Sci., USA,* 83:3091–3095 (May, 1996).

Freshney, M.G., "Colony–Forming Assay for CFC–GM, BFU–E, CFC–GEMM, and CFC–mix," In: *Culture of Hematopoietic Cells,* Freshney et al. (Eds.), Wiley–Liss, Inc., New York, N.Y., pp. 265–268 (1994).

Friedman, T., "Progress Toward Human Gene Therapy," *Science,* 244: 1275–1281 (1989).

Fulmer, R. et al., "Transplantation of Cardiac Tissue into the Mouse Ear," *Am. J. Anat.,* 113:273–285 (1963).

Galy, A. et al., "Delineation of T–Progenitor Cell Activity Within the CD34$^+$ Compartment of Adult Bone Marrow, "*Blood,* 85:2770–2778 (May, 1995).

Gluzman, Y., "SV40–Transformed Simian Cells Support the Replication of Early SV40 Mutants," *Cell,* 23:175–182 (1981).

Goding, J.W., "Conjugation of Antibodies with Fluorochromes: Modifications to the Standard Methods," *J. Immunol. Meth.,* 13:215–226 (1976).

Gorczyca, W. et al., "Detection of DNA Strand Breaks in Individual Apoptotic Cells by the in Situ Terminal Deoxynucleotidyl Transferase and Nick Translation Assays," *Cancer Research,* 53:1945–1951 (Apr., 1993).

Gorczyca, W. et al., "DNA strand breaks occurring during apoptosis: Their early in situ detection by the terminal deoxynucleotidyl transferase and nick translation assays and prevention by serine protease inhibitors," *Internat. J. Oncol.,* 1:639–648 (1992).

Gorczyca, W. et al., "Induction of DNA Strand Breaks Associated with Apoptosis during Treatment of Leukemias," *Leukemia,* 7:659–670 (May, 1993).

Green, L. et al., "Analysis of Nitrate, Nitrite, and [$^{15}$N] Nitrate in Biological Fluids," *Anal. Biochem.,* 126:131–138 (1982).

Greenberger, J. et al., "Demonstration of permanent factor–dependent multipotential (erythroid/neutrophil/basophil) hematopoietic progenitor cell lines," *Proc. Natl. Acad. Sci., USA,* 80:2931–2935 (May, 1983).

Gross, S. et al., "Cytokine–Activated Endothelial Cells Express an Isotype of Nitric Oxide Synthase Which Is Tetrahydrobiopterin–Dependent, Calmodulin–Independent and Inhibited By Arginine Analogs With A Rank–Order Of Potency Characteristic Of Activated Macrophages," *Biochem. Biophys. Res. Commun.,* 178:823–829 (Aug., 1991).

Gruber, B. et al., "Transforming Growth Factor–β1 Mediates Mast Cell Chemotaxis," *J. Immunol.,* 152:5860–5867 (1994).

Guéry, J–C et al., "Dendritic Cells Are the Most Efficient in Presenting Endogenous Naturally Processed Self–Epitopes to Class II–Restricted T Cells," *J. Immunol.,* 134:536–544 (1995).

Guice, K. et al., "Anti–tumor Necrosis Factor Antibody Augments Edema Formation in Caerulein–Induced Acute Pancreatitis," *J. Surg Res.,* 51:495–499 (1991).

Gyuris et al., "Cdi, a Human G1 and S Phase Protein Phosphatase That Associates with Cdk2," *Cell,* 75:791–803 (Nov., 1993).

Handa, K. et al., "Defining Cytolytic T Lymphocyte Recognition of Chemically Modified Self," *J. Immunol.,* 135:1564–1572 (Sep., 1985).

Hannum et al., "Interleukin–1 receptor antagonist activity of a human interleukin–1 inhibitor," *Nature,* 343:336–340 (Jan., 1990).

Heath, D.I. et al., "Role of Interleukin–6 in mediating the acute phase protein response and potential as an early means of severity assessment in acute pancreatitis," *Gut,* 34:41–45 (1993).

Herrmann, S. et al., "Analysis of the Two–Signal Requirement For Precursor Cytolytic T Lymphocyte Activation Using H–2K$^k$ in Liposomes,"*J. Immunol.*, 128:1968–1974 (May, 1982).

Herrmann, S. et al., "Secondary cytolytic T lymphocyte stimulation by purified H–2K$^K$ in liposomes," *Proc. Natl. Acad. Sci., USA*, 78:2488–2492 (Apr., 1981).

Hillenkamp, F. et al., "Matrix Assisted UV–Laser Desorption/Ionization: A New Approach to Mass Spectrometry of Large Biomolecules," in: *Biological Mass Spectrometry*, Burlingame et al., (eds.), Elsevier Science Pub., Amsterdam, p. 49–60 (1990).

Hirayama, F. et al., "Clonal proliferation of murine lympho–hemopoietic progenitors in culture," *Proc. Natl. Acad. Sci., USA*, 89:5907–5911 (Jul., 1992).

Hoheisel et al., "Quantitative Measurements on the Duplex Stability of 2,6–Diaminopurine and 5–Chloro–Uracil Nucleotides using Enzymatically Synthesized Oligomers," *FEBS Lett*, 274:103–106 (1990).

Holoshitz, J. et al., "Lines of T lymphocytes Induce or Vaccinate Against Autoimmune Arthritis," *Science*, 219:56–58 (Jan., 1983).

Huang et al., "Role of Bone Marrow–Derived Cells in Presenting MHC Class I–Restricted Tumor Antigens," *Science*, 264:961–965 (May, 1994).

Humphrey, W. et al., "Effect of Intravenous Prostaglandin E1 on Thrombolysis Induced by Human Recombinant Tissue–type Plasminogen Activator in Feline Peripheral Arterial Thrombosis," *Fibrinolysis*, 5:71–79 (1991).

Hurby et al., "Application of Synthetic Peptides: Antisense Peptides," In *Synthetic Peptides, A User's Guide*, W.H. Freeman, NY, pp. 289–307 (1992).

Huth–Fehre, T. et al., "Matrix Assisted Laser Desorption Mass Spectrometry of Oligodeoxythymidylic Acids," *Rapid Comm. Mass Spect.*, 6:209–213 (1992).

Ikuta, S. et al., "Dissociation Kinetics of 19 Base Paired Oligonucleotide–DNA Duplexes Containing Different Single Mismatched Base Pairs," *Nucleic Acids Research*, 15:797–811 (1987).

Inaba, K. et al., "Dendritic Cells Pulsed with Protein Antigens In Vitro Can Prime Antigen–specific, MHC–restricted T Cells In Situ," *J. Exp. Med.*, 172:631–640 (Aug., 1990).

Inaba, M. et al., "Distinct Mechanisms of Neonatal Tolerance Induced by Dendritic Cells and Thymic B Cells," *J. Exp. Med.*, 173:549–559 (Mar., 1991).

Inouye, S. et al., "Microplate Hybridization of Amplified Viral DNA Segment," *J. Clin. Microbiol.*, 28:1469–1472 (1990).

Itoh et al., "The Polypeptide Encoded by the cDNA for Human Cell Surface Antigen Fas Can Mediate Apoptosis," *Cell*, 66:233–243 (Jul., 1991).

Johansson, B. et al., "Evidence for Involvement of Activin A and Bone Morphogenetic Protein 4 in Mammalian Mesoderm and Hematopoietic Development," *Mol. Cell. Biol.*, 15:141–151 (Jan., 1995).

Johnston, J. et al., "Human T Lymphocyte Chemotaxis and Adhesion Induced by Vasoactive Intestinal Peptide," *J. Immunol.*, 153:1762–1768 (1994).

Kasprzak, A. et al., "Location of a Contact Site between Actin and Myosin in the Three–Dimensional Structure of the Acto–S1 Complex," *Biochemistry*, 28:9230–9238 (1989).

Kaufman, R. et al., "Improved vectors for stable expression of foreign genes in mammalian cells by use of the untranslated leader sequence from EMC virus," *Nucleic Acids Research*, 19:4485–4490 (1991).

Kaufman, R., "Selection and Coamplification of Heterologous Genes in Mammalian Cells," *Methods in Enzymology*, 185:537–566 (1990).

Keller, G. et al., "Hematopoietic Commitment during Embryonic Stem Cell Differentiation in Culture," *Mol. Cell. Biol.*, 13:473–486 (Jan., 1993).

Kohler, G. et al, "Continuous Cultures of Fused Cells Secreting Antibody of Predefined Specificity," *Nature*, 256:495–497 (1975).

Kozbor, D. et al., "The Production of Monoclonal Antibodies from Human Lymphocytes," *Immunology Today*, 4:72–79 (1983).

Krasney, P.A. et al., "Further Aspects of IL–1$\beta$ Secretion Revealed By Transfected Monkey Kidney Cells," *Cytokine*, 4(2):134–143 (Mar., 1992).

Krasnow, S. et al., "Tumor Necrosis Factor–$\alpha$, Interleukin 1, and Phorbol Myristate Acetate Are Independent Activators of NF–$\kappa$B Which Differentially Activate T Cells," *Cytokine*, 3:372–379 (Sep., 1991).

Krstenansky, J. et al., "Antithrombin properties of C–terminus of hirudin using synthetic unsulfated N$^\alpha$–acetyl–hirudin$_{45-65}$," *FEBS Lett.*, 211:10–16 (Jan., 1987).

Lamture, J. et al., "Direct detection of nucleic acid hybridization on the surface of a charge coupled device," *Nucleic Acids Research*, 22:2121–2125 (Jun., 1994).

Landegren, U. et al., "A Ligase–Mediated Gene Detection Technique," *Science*, 241:1077–1080 (1988).

Lee, J.S. et al., "Complexes formed by (pyrimidine)$_n$ (purine)$_n$ DNAs on lowering the pH are three–stranded," *Nucl. Acids Res.*, 6:3073–3091 (1979).

Lehrach, H. et al., "Hybridization Fingerprinting in Genome Mapping and Sequencing," in: *Genomic Analysis Volume 1: Genetic and Physical Mapping*, Cold Spring Harbor Laboratory Press, pp.39–81 (1990).

Lenschow et al., "Long–Term Survival of Xenogeneic Pancreatic Islet Grafts Induced by CTLA4Ig," *Science*, 257:789–792 (Aug., 1992).

Lind, M. et al., "Effects of osteotropic growth factors," *APMIS*, 103:140–146 (1995).

Linet, O. et al., "Tolerance and Pharmacology of Ciprostene, a Stable Epoprostenol (Prostacyclin) Analogue in Humans," *J. Clin. Pharmacol.*, 26:131–140 (1986).

Ling, N. et al., "Pituitary FSH is released by a heterodimer of the $\beta$–subunits from the two forms of inhibin," *Nature*, 321:779–782 (Jun., 1986).

Liou, H–C et al., "Regulation of the NF–$\chi$B/rel transcription factor and I$_\chi$B inhibitor system," *Cur. Opin. Cell Biol.*, 5:477–487 (1993).

Lovenberg, T. et al., "Cloning of a cDNA Encoding a Novel Interleukin–1 Receptor Related Protein (IL1R–rp2)," *J. Neuroimmunol.*, 70:113–122 (1996).

Lutz, Y. et al., "The Distribution of Two hnRNP–Associated Proteins Defined by a Monoclonal Antibody Is Altered in Heat–Shocked HeLa Cells," *Exp. Cell Research.*, 175:109–124 (1988).

Macatonia, S. et al., "Dendritic Cells Produced IL–12 and Direct the Development of Th1 Cells from Naive CD4$^+$ T Cells," *J. Immunology*, 154:5071–5079 (1995).

Macatonia, S. et al., "Primary Stimulation By Dendritic Cells Induces Antiviral Proliferative and Cytotoxic T Cell Responses in Vitro," *J. Exp. Med.,* 169:1255–1264 (Apr., 1989).

Maliszewski, C. et al., "Cytokine Receptors and B Cell Functions," *J. Immunol.,* 144:3028–3033 (Apr., 1990).

Mandrup–Poulsen, T. et al., "Affinity–purified human Interleukin I is cytotoxic to isolated islets of Langerhans," *Diabetologia,* 29:63–67 (1986).

Manso, M. et al., "Cerulein–Induced Acute Pancreatitis in the Rat," *Digestive Disease and Sciences,* 37:364–368 (Mar., 1992).

Mason, A. et al., "Complementary DNA sequences of ovarian follicular fluid inhibin show precursor structure and homology with transforming growth factor–$\beta$," *Nature,* 318:659–663 (Dec., 1985).

McClanahan, T. et al., "Hematopoietic Growth Factor Receptor Genes as Markers of Lineage Commitment During In Vitro Development of Hematopoietic Cells," *Blood,* 81:2903–2915 (Jun., 1993).

McDowell, R.S. et al., "Structural Studies of Potent Constrained RGD Peptides," *J. Amer. Chem. Soc.,* 114:9245–9253 (Nov., 1992).

McNiece, I. et al., "Primitive Hematopoietic Colony Forming Cells with High Proliferative Potential," In: *Culture of Hematopoietic Cells,* Freshney et al. (Eds.), Wiley–Liss, Inc., New York, N.Y., pp. 23–39 (1994).

Merrifield, R.P., "Solid Phase Peptide Synthesis: I. The Synthesis of a Tetrapeptide," *J. Amer. Chem. Soc.,* 85:2149–2154 (Jul., 1963).

Miller, A.D., "Human Gene Therapy Comes of Age," *Nature,* 357: 455–460 (1992).

Moreau et al., "Leukaemia inhibitory factor is identical to the myeloid growth factor human interleukin for DA cells," *Nature,* 336:690–692 (Dec., 1988).

Morrisey, D. et al., "Nucleic Acid Hybridization Assays Employing dA–Tailed Capture Probes. Single Capture Methods," *Mol. Cell. Probes,* 2:189–207 (1989).

Mulero, J.J. et al., "IL1HY1:A Novel Interleukin–1 Receptor Antagonist Gene," *Biochem. Biophys. Res. Comm.,* 263(3):702–706 (1999).

Müller, S. et al. "Cloning of ATAC, an activation–induced, chemokine–related molecule exclusively expressed in $CD8^+$ T lymphocytes," *Eur. J. Immunol.,* 25:1744–1748 (1995).

Murakami, A. et al., "Fluorescent–Labeled Oligonucleotide Probes : Detection of Hybrid Formation in Solution by Fluorescence Polarization Spectroscopy," *Nucleic Acids Res.,* (England), 19:4097–102 (1991).

Murayama, K. et al., "Does Somatostatin Analogue Prevent Experimental Acute Pancreatitis," *Arch. Surg.,* 125:1570–1572 (Dec., 1990).

Nagata, Y. et al., "Quantification of Picogram Levels of Specific DNA Immobilized in Microtiter Wells," *FEBS Lett* (*Netherlands*), 183: 379–382 (1985).

Nair, S. et al., "Induction of Primary, Antiviral Cytotoxic, and Proliferative Responses with Antigens Administered via Dendritic Cells," *J. Virol.,* 67:4062–4069 (Jul., 1993).

Natanson, C. et al., "Endotoxin and Tumor Necrosis Factor Challenges in Dogs Simulate the Cardiovascular Profile of Human Septic Shock," *J. Exp. Med.,* 169:823–832 (Mar., 1989).

Neben, S. et al., "Synergistic effects of interleukin–11 with other growth factors on the expansion of murine hematopoietic progenitors and maintenance of stem cells in liquid culture," *Experimental Hematology,* 22:353–359 (1994).

Nichols, R. et al. "A Universal Nucleoside for Use at Ambiguous Sites in DNA Primers," *Nature,* 369:492–493 (1994).

Nizetic, D. et al., "An Improved Bacterial Colony Lysis Procedure Enables Direct DNA Hybridisation Using Short (10, 11 bases) Oligonucleotides to Cosmids," *Nucleic Acids Research,* 19:182 (1991).

Ohlsson et al., "Interleukin–1 receptor antagonist reduces mortality from endotoxin shock," *Nature,* 348:550–552 (Dec., 1990).

Okano, H. et al., "Myelin Basic Protein Gene and the Function of Antisense RNA in Its Repression in Myelin–Deficient Mutant Mouse," *J. Neurochem.,* 56:560–567 (1991).

Okusawa, S. et al., "Interleukin 1 Induces a Shock–like State in Rabbits," *J. Clin. Invest.,* 81:1162–1172 (Apr., 1988).

Osborn, L. et al., "Tumor necrosis factor $\alpha$ and interleukin 1 stimulate the human immunodeficiency virus enhancer by activation of the nuclear factor $\kappa B$," *Proc. Natl. Acad. Sci., USA,* 86:2336–2340 (Apr., 1989).

Parnet, P. et al.,"IL–1Rrp is a Novel Receptor–Like Molecule Similar to the Type I Interleukin–1 Receptor and Its Homologous T1/ST2 and IL–IR AcP," *J. Biol. Chem.,* 271:3967–3970 (Feb., 1996).

Parrillo, J.E., "Septic Shock in Humans: Clinical Evaluation, Pathogenesis, and Therapeutic Approach," In: *Textbook of Critical Care,* Shoemaker et al., (eds.), 2nd ed.) Saunders Publishing Co., Philadelphia, PA, p.1006–1024 (1989).

Paterson, B. et al., "Structural gene identification and mapping by DNA–mRNA hybrid–arrested cell–free translation," *Proc. Natl. Acad. Sci.,* 74:4370–4374 (Oct., 1977).

Paul (ed.), in *Fundamental Immunology,* Raven Press, New York, pp. 840–856 (1989).

Paunesku, T. et al., "Origin of Rat $\beta$–Globulin Haplotypes Containing Three and Five Genes," *Mol. Biol. Evol.,* 7(5):407–422 (1990).

Pease, A.C. et al., "Light–generated Oligonucleotide Arrays for Rapid DNA Sequence Analysis," *Proc. Natl. Acad. Sci. USA,* 91:5022–5026 (1994).

Pestronk, A. et al., "Effects of Aging on Nerve Sprouting and Regeneration," *Exp. Neurol.,* 70:65–82 (1980).

Pevzner, P.A., "1–Tuple DNA Sequencing: Computer Analysis," *J. Biomol. Struct. & Dyn.,* 7(1):63–73 (1989).

Ploemacher, R.E., "Cobblestone Area Forming Cell (CAFC) Assay," In: *Culture of Hematopoietic Cells,* Freshney et al. (Eds.), Wiley–Liss, Inc., New York, N.Y., pp. 1–21 (1994).

Pober, J., "Activation of Cultured Human Endothelial Cells by Recombinant Lymphotoxin: Comparison with Tumor Necrosis Factor and Interleukin I Species," *J. Immunol.,* 138:3319–3324 (May, 1987).

Pontius, B.W. et al., "Rapid Renaturation of Complementary DNA Strands Mediated by Cationic Detergents: A Role for High–Probability Binding Domains in Enhancing the Kinetics of Molecular Assembly Processes,"*Proc. Natl. Acad. Sci., USA,* 88:8327–8241 (1991).

Porgador, A. et al., "Bone Marrow–generated Dendritic Cells Pulsed with a Class I–restricted Peptide Are Potent Inducers of Cytotoxic T Lymphocytes," *J. Exp. Med.,* 182:255–260 (Jul., 1995).

Pörshke, D. et al.,"Co–operative Non–enzymatic Base Recognition," *J. Mol. Biol.,* 62:361–381 (1971).

Rasmussen, S.R. et al., "Covalent Immobilization of DNA onto Polystyrene Microwells: The Molecules Are Only Bound at the 5' End," *Anal. Biochem.,* 198:138–142 (1991).

Rosenstein, Y. et al., "Direct Evidence For Binding of CD8 to HLA Class I Antigens," *J. Exp. Med.,* 169:149–160 (Jan., 1989).

Rossi et al., "Prostacyclin Synthesis Induced in Vascular Cells by Interleukin–1," *Science,* 229:174–176 (1985).

Saluja, A. et al., "In vivo rat pancreatic acinar cell function during supramaximal stimulation with caerulein," *Am. J. Physiol.,* 249 (Amer. Physiological Society):G702–G710 (1985).

Sambrook et al., Molecular Cloning: A Laboratory Manual, Cold Spring Harbor Laboratory, NY 9.14–9.23; 9.24–9.28 (1989).

Saragovi et al., "Loops and Secondary Structure Mimetics: Development and Applications in Basic Science and Rational Drug Design," *Bio/Technology,* 10:773–778 (Jul., 1992).

Schaub, R., "Ciprostene, A Stable Prostacyclin Analog, Produces Peripheral Vasodilation, Platelet Inhibition and Increased Clot Dissolution in the Cat," *Prostaglandins,* 35:467–474 (Mar., 1988).

Schoenberg, M. et al., "The Role of Oxygen Radicals in Experimental Acute Pancreatitis," *Free Radical Biology Medicine,* 12:515–522 (1992).

Schriefer, L.A. et al., "Low Pressure DNA Shearing: A Method for Random DNA Sequence Analysis," *Nucleic Acids Res. (England),* 18(24):7455–6 (1990).

Schubert, F. et al., "One–step Labeling of Oligonucleotides with Fluorsciene During Automated Synthesis," *Nucleic Acids Res. (England),* 18:3427 (1990).

Seckinger, P. et al., "A Urine Inhibitor of Interleukin 1 Activity Affects Both Interleukin $1\alpha$ and $1\beta$ But Not Tumor Necrosis Factor $\alpha$," *J. Immunol.,* 139:1541–1545 (Sep., 1987).

Shirakawa, F. et al., "In Vitro Activation and Nuclear Translocation of NF–κB Catalyzed by Cyclic AMP–Dependent Protein Kinase and Protein Kinase C," *Mol. Cell. Biol.,* 9:2424–2430 (Jun., 1989).

Smith, C. et al., "Characterization of a murine lymphokine distinct from interleukin 2 and interleukin 3 (IL–3) possessing a T–cell growth factor activity and a mast–cell growth factor activity that synergizes with IL–3," *Proc. Natl. Acad. Sci., USA,* 83:1857–1861 (Mar., 1986).

Smith, R.D. et al., "New Developments in Biochemical Mass Spectrometry: Electrospray Ionization," *Anal. Chem.,* 62:882–899 (1990).

Spooncer, E. et al., "Long–Term Mouse Myeloid Bone Marrow Cultures," in *Culture of Hematopoietic Cells,* Freshney et al. (Eds.), Wiley–Liss, Inc., New York, N.Y., pp. 163–179 (1994).

Steer, M.L., "How and Where Does Acute Pancreatitis Begin?" *Arch. Surg.,* 127:1350–1353 (Nov., 1992).

Sternberger, L.A. et al., "The Unlabeled Antibody Enzyme Method of immunohistochemistry—Preparation and Properties of Soluble Antigen–Antibody Complex (Horseradish Peroxidase—Antihorseradish Peroxidase) and Its Use in Identification of Spriochetes," *J. Histochem. Cytochem.,* 18: 315–333 (1970).

Stevanović, M. et al., Variant chromosomal arrangement of adult β–globin genes in rat *Gene,* 79:139–150 (1989).

Stitt, T. et al., "The Anticoagulation Factor Protein S and Its Relative, Gas6, Are Ligands for the Tyro 3/Axl Family of Receptor Tyrosine Kinases," *Cell,* 80:661–670 (Feb., 1995).

Stoltenborg, J. et al., "A fluorescent cellular adhesion assay using insect cell produced human VCAM1," *J. Immunol. Methods,* 175:59–68 (1994).

Strezoska, Z. et al., "DNA Sequencing by Hybridization: 100 Bases Read by a Non–Gel–Based Method," *Proc. Natl. Acad. Sci., USA,* 88:10089–10093 (1991).

Summers, M. et al., In: A Manual of Methods for Baculovirus Vectors and Insect Cell Culture Procedures, Department of Entomology, Texas Agricultural Experiment Station and Texas A & M University, College Station, Texas, Texas Agricultural Experiment Station, Bulletin No. 1555, pp.1–56 (May, 1987).

Sutherland, H. et al.,"Long–Term Culture of Human Myeloid Cells," In: *Culture of Hematopoietic Cells,* Freshney et al. (Eds.), Wiley–Liss, Inc., New York, N.Y., pp. 139–162 (1994).

Takai, Y. et al., "B Cell Stimulatory Factor–2 Is Involved In The Differentiation of Cytotoxic T Lymphocytes," *J. Immunol.,* 140:508–512 (Jan., 1988).

Takai, Y. et al, "Direct evidence for a receptor–ligand interaction between the T–cell surface antigen CD2 and lymphocyte–function–associated antigen 3," *Proc. Natl. Acad. Sci., USA,* 84:6864–6868 (Oct., 1987).

Takai, Y. et al., "Requirement For Three Distinct Lymphokines For The Induction of Cytotoxic T Lymphocytes From Thymocytes," *J. Immunol.,* 137:3494–3500 (Dec., 1986).

Tani, S. et al., "Histologic and biochemical alterations in experimental acute pancreatitis induced by supramaximal caerulein stimulation," *International J. Pancreatology,* 2:337–348 (1987).

Taub, D. et al. "Monocyte Chemotactic Protein–1 (MCP–1), –2, –3 Are Chemotactic for Human T Lymphocytes,"*J. Clin. Invest.,* 95:1370–1376 (Mar., 1995).

Toki, J. et al., "Analyses of T–cell differentiation from hemopoietic stem cells in the $G_O$ phase by an in vitro method," *Proc. Nat. Acad. Sci., USA,* 88:7548–7551 (Sep., 1991).

Tracey, K. et al.,"Shock and Tissue Injury Induced by Recombinant Human Cachectin," *Science,* 234:470–474 (Oct., 1986).

Trager, D. et al., "Cardiac Allograft Prolongation in Mice Treated with Combined Posttransplantation Total–Lymphoid Irradiation and Anti–L3T4 Antibody Therapy," *Transplantation,* 47:587–591 (Apr., 1989).

Turka, L. et al., "T–cell activation by the CD28 ligand B7 is required for cardiac allograft rejection in vivo," *Proc. Natl. Acad. Sci., USA,* 89:11102–11105 (Nov., 1992).

Vale, W. et al., "Culture of Enzymatically Dispersed Anterior Pituitary Cells: Functional Validation of a Method," *Endocrinology,* 91:562–572 (1972).

Vale, W. et al., "Purification and characterization of an FSH releasing protein from porcine ovarian follicular fluid," *Nature,* 321:776–779 (Jun., 1986).

Van Buren, C. et al., "Synergistic Effect of a Nucleotide––Free Diet and Cyclosporine on Allograft Survival," *Transplant. Proc.,* 15:2967–2968 (Dec., 1983).

Van Ness, J. et al., "A Versatile Solid Support System for Oligodeoxynucleotide Probe–Based Hybridization Assays," *Nucleic Acids Res.,* (England)19:3345–3350 (1991).

Verma, I.M., "Gene Therapy—Treatment of Disease by Introducing Healthy Genes into the Body is Becoming Feasible. But the Therapy will not Reach its Full Potential until the Genes Can Be Coaxed to Work throughout Life," *Scientific American*, pp. 68–72, 81–84 (1990).

Vollrath, D. et al., "The Human Y Chromosome: A 43–Interval Map Based on Naturally Occurring Deletions," *Science*, 258:52–59 (1992).

Wakabayashi, G. et al., "A specific receptor antagonist for interleukin 1 prevents *Escherichia coli*–induced shock in rabbits," *FASEB J.*, 5:338–343 (1991).

Waksman, B. et al., "Passive Transfer of Adjuvant Arthritis in Rats with Living Lymphoid Cells of Sensitized Donors," *Int. Arch. Allergy Appl. Immunol.*, 23:129–139 1963).

Wallace, R.B. et al., "Hybridization of Synthetic Oligodeoxyribonucleotides to Φχ 174 DNA: The Effect of Single Base Pair Mismatch," *Nucleic Acids Research*, 6:3543–3557 (1979).

Walsh, P.S. et al., "Preferential PCR Amplification of Alleles: Mechanisms and Solutions," *PCR Methods Appl*, 1:241–250 (1992).

Weinberger, O. et al., "Cellular interactions in the generation of cytolytic T Lymphocyte responses: Role of Ia–positive splenic adherent cells in presentation of H–2 antigen," *Proc. Natl. Acad. Sci., USA*, 77:6091–6095 (Oct., 1980).

Weinberger, O. et al., "Cellular interactions in the generation of cytolytic T lymphocyte responses Analysis of the helper T cell pathway," *Eur. J. Immunol.*, 11:405–411 (1981).

Wells, J.A. et al.,"Cassette Mutagenesis: An Efficient Method for Generation of Multiple Mutations at Defined Sites," Gene, 34:315–323 (1985).

Winter, G., "Epidermal Regeneration Studied in the Domestic Pig," pp. 71–112, Maibach et al., (eds.), Year Book Medical Publishers, Inc., Chicago.

Wolter, A. et al., "Negative Ion FAB Mass Spectrometric Analysis of Non–Charged Key Intermediates in Oligonucleotide Synthesis: Rapid Identification of Partially Protected Dinucleoside Monophosphates," *Biomedical Environ. Mass Spec.*, 14:111–116 (1987).

Xu, L. et al., "Ketone Electrophores and an Olefin–Release Group Electrophore–Labeled DNA Oligomer Detection via Electron Capture," *Chromatography*, 764:95–102 (1997).

Yamashita, M. et al., "Electrospray Ion Source. Another Variation on the Free–Jet Theme," *J. Phys. Chem.*, 88:4451–4459 (1984).

Zacharchuk,, C. et al., "Programmed T Lymphocyte Death: Cell Activation–and Steroid–Induced Pathways Are Mutually Antagonistic," *J. Immunol.*, 145:4037–4045 (Dec., 1990).

Zamai, L. et al., "Optimal Detection of Apoptosis by Flow Cytometry Depends on Cell Morphology," *Cytometry*, 14:891–897 (1993).

Zoller, M.J. et al., Oligonucleotide–Directed Mutagenesis Using M13–Derived Vectors: An Efficient and General Procedure for the Production of Point Mutations in any Fragment of DNA, *Nucleic Acids Res.*, 10:6487–6500 (1982).

International Search Report, International Application No. PCT/US99/04291, filed Apr. 5, 1999, mailing date of International search report Nov. 1, 2000.

```
                                                                                                              70
                                                                10        20        30        40        50        60
                  (SEQ ID NO:3)      ----------------------------------------------------------------------   1
SEQ ID NO: 30)    Il-1Ra-human       MEICRGLRSHLITLLL-FLFHSETICRPSGRKSSKMQAFRIWDVNQKTFYLRNNQLVAGYLQGPNVNLEE  69
SEQ ID NO:9)      Il-1Ra-mouse       MEICWGPYSHLISLLILLLFHSEAACRPSGKRPCKMQAFRIWDTNQKTFYLRNNQLIAGYLQGPNIKLEE 70
SEQ ID NO:10)     Il-1Ra-rat         MEICRGPYSHLISLLLILLFRSESAGHPAGKRPCKMQAFRIWDTNQKTFYLRNNQLIAGYLQGPNTKLEE 70
SEQ ID NO:11)     Il-1Ra-rabbit      MRPSRSTRRHLISLLL-FLFHSETACRPSGKRPCRMQAFRIWDVNQKTFYLRNNQLVAGYLQGPNAKLEE 69

80        90        100       110       120       130       140
                  (SEQ ID NO:3)      -----------------------------PTLTLEPVNIMELYLGAKESKSFTFYRRDMGLTSSFESA  39
SEQ ID NO: 30)    Il-1Ra-human       KIDVVPIEPHALFLGIHGGKMCLSCVKSGDETRLQLEAVNITDLSENRKQDKRFAFIRSDSGPTTSFESA 139
SEQ ID NO:9)      Il-1Ra-mouse       KIDMVPIDLHSVFLGIHGGKLCLSCAKSGDDIKLQLEEVNITDLSKNKEEDKRFTFIRSEKGPTTSFESA 140
SEQ ID NO:10)     Il-1Ra-rat         KIDMVPIDFRNVFLGIHGGKLCLSCVKSGDDTKLQLEEVNITDLNKNKEEDKRFTFIRSETGPTTSFESL 140
SEQ ID NO:11)     Il-1Ra-rabbit      RIDVVPLEPQLLFLGIQRGKLCLSCVKSGDKMKLHLEAVNITDLGKNKEQDKRFTFIRSNSGPTTFESA 139

150       160       170       180
                  (SEQ ID NO:3)      AYPGWFLCTVPEADQPVRLTQLPENGGWNAPITDFYFQQCD                              80
SEQ ID NO: 30)    Il-1Ra-human       ACPGWFLCTAMEADQPVSLTNMPDEG---VMVTKFYFQEDE                             177
SEQ ID NO:9)      Il-1Ra-mouse       ACPGWFLCTTLEADRPVSLTNTPEEP---LIVTKFYFQEDQ                             178
SEQ ID NO:10)     Il-1Ra-rat         ACPGWFLCTTLEADHPVSLTNTPKEP---CTVTKFYFQEDQ                             178
SEQ ID NO:11)     Il-1Ra-rabbit      SCPGWFLCTALEADQPVSLTNTPDDS---IVVTKFYFQEDQ                             177
```

FIG. 1

(SEQ ID NO:1)

CCGACTCTAACACTAGAGCCAGTGAACATCATGGAGCTCTATCTTGGTGCCAAGGAA
TCCAAGAGCTTCACCTTCTACCGGGGACATGGGGCTCACCTCCAGCTTCGAGTCG
GCTGCCTACCCGGGCTGTTCCTGTGCACGGTGCCTGAAGCCGATCAGCCTGTCAGA
CTCACCCAGCTTCCCGAGAATGGCTGGCAGCCCCATCACAGACTTCTACTTC
CAGCAGTGTGACTAGGGCAACGTGCCCCCAGAACTCCCTGGGCAGAGCCAGCTCG
GNTGANGGGNGAGNGNNNNNNNNNNNNNGNNNNNNNNNNNNNNNNNNNNN
NANNNNNNNNNG (SEQ ID NO:2)

CCGACTCTAACACTAGAGCCAGTGAACATCATGGAGCTCTATCTTGGTGCCAAGGAATCCAAGAGCTTCACCTTCTACCG
GCGGGACATGGGGCTCACCTCCAGCTTCGAGTCGGCTGCCTACCCGGGCTGTTCCTGTGCACGGTGCCTGAAGCCGATC
AGCCTGTCAGACTGTCAGCTTCACCCAGCTTCCCGAGAATGGTGGCTGAATGCCCCCATCACAGACTTCTACTTCCAGCAGTGTGAC
TAGGGCAACGTGCCCCCAGAACTCCCTGGGCAGAGCCAGCTCGGGGTGAGTGGAGGACCCATGGCGGACAA
TCACTCTCTCTGCTCTCAGGACCCCACGTCGACTTAGTGGGCACCACTTTGTCTTCTGGTTCCCAGTTTGGAT
AAATTCTGAGATTTGGAGCTCAGTCCACGGTCCTCCCCACTGGATGGTGCTACTGCTGTGGGAACCTTGTAAAAACCATG
TGGGTAAACTGGGAATAACATGAAAAGATTTCTGTGGGGGTGGTGGGGAGTGGGGAATCATTCCTGCTTAATGG
TAACTGACAAGTGTTACCCTGAGCCCCGCAGGAGAGGGAGGGTGGTCATAGAGTCAGGGATCTATGGCCCTTGGCCCACC
AGTCCTGTCACTCACACTGTGCCACTGTCATATCCTGTCATATGCTCATCATCTTGTTGTGGGCATGAGGAGG
CCCTTCCCTTAATCCTGCCACTGTGCCACTGTCATATCCTGTCATATGCTGATCCTCTTTAAAACCCAAG
TGGTGATGTCAGAAGAAATGGCTCGAGCTCAGAAGATAAAAGATAAGTAGGTATGCTGATCCTCTTTGATCCTCTTTAAAACCCAAG
ATACAATCAAAATCCCAGATGCTGGTCTCTATTCCCATGAAAAGTGCTCATGACATATTGAGAAGACCTACTTACAAAG
TGGCATATATTGCAATTAATTTA

FIG. 2

(SEQ ID NO:3)

PTLTLEPVNIMELYLGAKESKSFTFYRRDMGLTSSFESAAYPGWFLCTVPEADQPVRLTQLPENGGWNAPIT
DFYFQQCD

FIG. 3

RECEPTOR BINDING REGION OF IL-1β

| | |
|---|---|
| IL-1β (SEQ ID NO:12) | N Y P K K K M E K R F V F N K I E I |
| IL-1Ra (SEQ ID NO:13) | L S E N R K Q D K R F A F I R S D S |
| (SEQ ID NO:3) | L Y L G A K E S K S F T F Y R R D M |

FIG. 4

(SEQ ID NO:4)

CCACGCGTCCGCACAGCTCCCGCCAGGAGAAAGGAACATTCTGAGGGGAGTCTACACCCTG
TGGAGCTCAAGATGGTCCTGAGTGGGGCGCTGTGCTTCCGAATGAAGGACTCGGCATTGAA
GGTGCTTTATCTGCATAATAACCAGCTTCTAGCTGGAGGGCTGCATGCAGGGAAGGTCATT
AAAGGTGAAGAGATCAGCGTGGTCCCCAATCGGTGGCTGGATGCCAGCCTGTCCCCCGTCA
TCCTGGGTGTCCAGGGTGGAAGCCAGTGCCTGTCATGTGGGGTGGGGCAGGAGCCGACTCT
AACACTAGAGCCAGTGAACATCATGGAGCTCTATCTTGGTGCCAAGGAATCCAAGAGCTTC
ACCTTCTACCGGCGGGACATGGGGCTCACCTCCAGCTTCGAGTCGGCTGCCTACCCGGGCT
GGTTCCTGTGCACGGTGCCTGAAGCCGATCAGCCTGTCAGACTCACCCAGCTTCCCGAGAA
TGGTGGCTGGAATGCCCCCATCACAGACTTCTACTTCCAGCAGTGTGACTAGGGCAACGTG
CCCCCCAGAACTCCCTGGGCAGAGCCAGCTCGGGTGAGGGTGAGTGGAGGAGACCCATGG
CGGACAATCACTCTCTCTGCTCTCAGGACCCCCACGTCTGACTTAGTGGGCACCTGACCAC
TTTGTCTTCTGGTTCCCAGTTTGGATAAATTCTGAGATTTGGAGCTCAGTCCACGGTCCTC
CCCCACTGGATGGTGCTACTGCTGTGGAACCTTGTAAAACCATGTGGGTAAACTGGGAA
TAACATGAAAAGATTTCTGTGGGGGTGGGGTGGGGAGTGGTGGGAATCATTCCTGCTTAA
TGGTAACTGACAAGTGTTACCCTGAGCCCCGCAGGCCAACCCATCCCCAGTTGAGCCTTAT
AGGGTCAGTAGCTCTCCACATGAAGTCCTGTCACTCACCACTGTGCAGGAGAGGGAGGTGG
TCATAGAGTCAGGGATCTATGGCCCTTGGCCCAGCCCCACCCCCTTCCCTTTAATCCTGCC
ACTGTCATATGCTACCTTTCCTATCTCTTCCCTCATCATCTTGTTGTGGGCATGAGGAGGT
GGTGATGTCAGAAGAAATGGCTCGAGCTCAGAAGATAAAAGATAAGTAGGGTATGCTGATC
CTCTTTTAAAAACCCAAGATACAATCAAAATCCCAGATGCTGGTCTCTATTCCCATGAAAA
AGTGCTCATGACATATTGAGAAGACCTACTTACAAAGTGGCATATATTTGCAATTAATTTT
A

FIG. 5

(SEQ ID NO:5)

MVLSGALCFRMKDSALKVLYLHNNQLLAGGLHAGKVIKGEEISVVPNRWLDASLSPVILGV
QGGSQCLSCGVGQEPTLTLEPVNIMELYLGAKESKSFTYRRDMGLTSSFESAAYPGWFLC
TVPEADQPVRLTQLPENGGWNAPITDFYFQQCD

FIG. 6

```
SEQ ID NO:5)                    MVLSGALC--------FRMKDSALKVLYLHNNQLLAGGLHAGKVIKGEEISVVPNRWLDASLSPVI   58
SEQ ID NO:14) HUMIL1RASIC  MALE-TICRPSGRKSSKMQAFRIWDVNQKTFYLRNNQLVAGYLQGPNVNLEEKIDVVP----IEPHALF   64
                                                                      *   *

SEQ ID NO:5)                    LGVQGGSQCLSCG-VGQEPTLTLEPVNIMELYLGAKESKSFTYRRDMGLTSSFESAAYPGWFLCTVPEA  127
SEQ ID NO:14) HUMIL1RASIC  LGIHGGKMCLSCVKSGDETRLQLEAVNITDLSENRKQDKRFAFIRSDSGPTTSFESAACPGWFLCTAMEA  134

SEQ ID NO:5)                    DQPVRLTQLPENGGWNAPITDFYFQQCD
SEQ ID NO:14) HUMIL1RASIC  DQPVSLTNMPDEG---VMVTKFYFQEDE
                                                    *
```

FIG. 7

(SEQ ID NO:6)

```
CACAGCTCCCGCCAGGAGAAAGGAACATTCTGAGGGGAGTCTACACCCTGTGGAGCTCAA
GATGGTCCTGAGTGGGGCGCTGTGCTTCCGAATGAAGGACTCGGCATTGAAGGTGCTTTA
TCTGCATAATAACCAGCTTCTAGCTGGAGGGCTGCATGCAGGGAAGGTCATTAAAGGTGA
AGAGATCAGCGTGGTCCCCAATCGGTGGCTGGATGCCAGCCTGTCCCCGTCATCCTGGG
TGTCCAGGGTGGAAGCCAGTGCCTGTCATGTGGGTGGGGCAGGAGCCGACTCTAACACT
AGAGCCAGTGAACATCATGGAGCTCTATCTTGGTGCCAAGGAATCCAAGAGCTTCACCTT
CTACCGGCGGGACATGGGGCTCACCTCCAGCTTCGAGTCGGCTGCCTACCCGGGCTGGTT
CCTGTGCACGGTGCCTGAAGCCGATCAGCCTGTCAGACTCACCCAGCTTCCCGAGAATGG
TGGCTGGAATGCCCCCATCACAGACTTCTACTTCCAGCAGTGTGACTAGGGCAACGTGCC
CCCCAGAACTCCCTGGGCAGAGCCAGCTCGGGTGAGGGGTGAGTGGAGGAGACCCATGGC
GGACAATCACTCTCTCTGCTCTCAGGACCCCACGTCTGACTTAGTGGGCACCTGACCAC
TTTGTCTTCTGGTTCCCAGTTTGGATAAATTCTGAGATTTGGAGCTCAGTCCACGGTCCT
CCCCCACTGGATGGTGCTACTGCTGTGGAACCTTGTAAAACCATGTGGGGTAAACTGGG
AATAACATGAAAGATTTCTGTGGGGGTGGGGTGGGGAGTGGTGGGAATCATTCCTGCT
TAATGGTAACTGACAAGTGTTACCCTGAGCCCCGCAGGCCAACCCATCCCCAGTTGAGCC
TTATAGGGTCAGTAGCTCTCCACATGAAGTCCTGTCACTCACCACTGTGCAGGAGAGGGA
GGTGGTCATAGAGTCAGGGATCTATGGCCCTTGGCCCAGCCCCACCCCCTTCCCTTTAAT
CCTGCCACTGTCATATGCTACCTTTCCTATCTCTTCCCTCATCATCTTGTTGTGGGCATG
AGGAGGTGGTGATGTCAGAAGAAATGGCTCGAGCTCAGAAGATAAAGATAAGTAGGGTA
TGCTGATCCTCTTTTAAAAACCCAAGATACAATCAAATCCCAGATGCTGGTCTCTATTC
CCATGAAAAGTGCTCATGACATATTGAGAAGACCTACTTACAAAGTGGCATATATTTGC
AATTAATTTTAATTAAAAGATACCTATTTATATATTTCTTTATAGAAAAAAGTCTGGAAG
AGTTTACTTCAATTGTAGCAATGTCAGGGTGGTGGCAGTATAGGTGATTTTTCTTTTAAT
TCTGTTAATTTATCTGTATTTCCTAATTTTTCTACAATGAAGATGAATTCCTTGTATAAA
AATAAGAAAAGAAATTAATCTTGAGGTAAGCAGAGCAGACATCATCTCTGATTGTCCTCA
GCCTCCACTTCCCCAGAGTAAATTCAAATTGAATCGAGCTCTGCTGCTCTGGTTGGTTGT
AGTAGTGATCAGGAAACAGATCTCAGCAAAGCCACTGAGGAGGAGGCTGTGCTGAAGTTG
TGTGGCTGGAATCTCTGGGTAAGGAACTTAAAGAACAAAAATCATCTGGTAATTCTTTCC
TAGAAGGATCACAGCCCTGGGATTCCAAGGCATTGGATCCAGTCTCTAAGAAGGCTGCT
GTACTGGTTGAATTGTGTCCCCCTCAAATTCACATCCTTCTTGGAATCTCAGTCTGTGAG
TTTATTTGGAGATAAGGTCTCTGCAGATGTAGTTAGTTAAGACAAGGTCATGCTGGATGA
AGGTAGACCTAAATTCAATATGACTGGTTTCCTTGTATGAAAAGGAGAGGACACAGAGAC
AGAGGAGACGCGGGGAAGACTATGTAAAGATGAAGGCAGAGATCGGAGTTTTGCAGCCAC
AAGCTAAGAAACACCAAGGATTGTGGCAACCATCAGAAGCTTGGAAGAGGCAAAGAAGAA
TTCTTCCCTAGAGGCTTTAGAGGGATAACGGCTCTGCTGAAACCTTAATCTCAGACTTCC
AGCCTCCTGAACGAAGAAAGAATAAATTTCGGCTGTTTTAAGCCACCAAGGATAATTGGT
TACAGCAGCTCTAGGAAACTAATACAGCTGCTAAAATGATCCCTGTCTCCTCGTGTTTAC
ATTCTGTGTGTGTCCCCTCCCACAATGTACCAAAGTTGTCTTTGTGACCAATAGAATATG
GCAGAAGTGATGGCATGCCACTTCCAAGATTAGGTTATAAAAGACACTGCAGCTTCTACT
TGAGCCCTCTCTCTCTGCCACCCACCGCCCCAATCTATCTTGGCTCACTCGCTCTGGGG
GAAGCTAGCTGCCATGCTATGAGCAGGCCTATAAAGAGACTTACGTGGTAAAAAATGAAG
TCTCCTGCCCACAGCCACATTAGTGAACCTAGAAGCAGAGACTCTGTGAGATAATCGATG
TTTGTTGTTTTAAAGTTGCTCAGTTTTGGTCTAACTTGTTATGCAGCAATAGATAAATAA
TATGCAGAGAAGAGAAAAAAAAAAAAAAAAAAAAAAAAAAAAAAAAAAAAAAAAAAAAAA
AAAAAAAA
```

FIG. 8

(SEQ ID NO:7)

CNGTTAATCCTACCACTATGAGNATGTCTTATCATTTAGTANGAAGATTTTTG
CTTTTTGCACATGAAAAATAGGTTGGAAAAAGTATAGGTTTTGTGATCTGTGT
ATGAAAGCTGTCTATAGTACATGTGTATGTGTGGGAGAAAAAGTGTTGTCATT
GGTTTTCTRATGANTCACTMAGAAAAGCAAGTATTCACATTTTTCTTGTGGC
TGTCTGATTTTCAGGTTTTTCTACAATGACATGTAGGCTGANCATTCCCTARG
CAGAGAGTCCCACYTCTAACATCTCYTGTAGGCCTGGCAAKGCAGCAGAAAS
NCAGAGGAAGGAAGGAGGRAGAAGGAAGGAGTGAAGRAAGGAGTAAAAAG
GTAAGGAAGAAAGGGAATAGGGRAGRAAGGGAGRAAATGGGAAGGGAAAR
AAGGAAAGGAAGGAAAGAGGGAGGGAAGAAAGRAAGGGAAAAGGGAGGGA
GTGAGTGAATGAAAGATGGAAAGAAGRAAGAAAGGGAGGGAGGCAGGGAG
GAAAGAAAGTTGCGCTTCCCTTGASCTGCCATGGGCACTGMYTCTTAGGGTC
TGAAAGCCCCTGAGATGCAAAAGCCTAGTGCTCACAAAGAGCTGGAAAGCCT
CAAGGAAGTTCTTCAATATTTCTGGAAGGAAACTGTCTCCAGAAGCTTCCCTC
CCCACGACAGATAATGAGCAGCAAGTGCTTCTGGCGACTTAGGGTGATGTGA
AATCACGCTGGGAATCCTGCTCCTCCTCAGGTCCTGGCAGTTTCAGGGCCCCT
CCCTAGGCCTTACTTAAAAGGCTGAGGCATCCTTGGAGGAACAGGCAGACTC
CACAGCTCCCGCCAGGAGAAAGGAACATTCTGAGGTATGCTCTGGGGCGCTG
GTGGTACCGGAGCTCTCTCCTGACCCCAGACCCAGAATCTGCTCCGTGGAGG
CTGTTCACATGCTGGGGAGCTCGGTGCAGCTGCTTGCTCCCAGACCCCAGCC
AACTCAGCCTCTCTCTCCATGATTTTCTGTTGTTTATTCCAAAATAGGGGAGT
CTACACCCTGTGGAGCTCAAGATGGTCCTGAGTGGGGCGCTGTGCTTCCGGT
GAGTGTATGAGGCCCTGGTTTGGTGGTGTCCTCCGGAGGAAGTGAGTTCTGG
ATAGACCCGTTGTCCAGCTCTGAGCAGGAGGGAGGAAGGGAGGGGCTGCCA
TTGSRGCTGKBAAATTGTGACCAGCACCTCATTGCTCTTAGAGTTTTCCCAGC
CTTTTTCAAATAGGGGCAGGACTGGGGCARGCCATCTCACAAGGGGWCCCTG
ATGCTGAGGGGGACAAGTGAACCTCCCAGWCTARAGCTCCAGCCAAGTCTAT
CCAAGGTGGGAACGGGGGCCAGGATCCCTGCTCAGAGCTCCGCCATTGTCCC
CCATCACAGTGAATGGATGTAAGCTCACCCACTCTGTGCCCCTACCTYCCTGC
TACTCTTTGGGGATAATWATAAAACAAAAACCATTACCATCAGCCAGTYTGT
MCACCCACTGGCATGTACCAAGCCAGACACTCTGCCGTGTTCTGGGCTTAAC
AACAGAGGATGAARAGTGGGCCTTTCTCTCAGKCTAATAAAGVACTTCCCAC
GATGKGTTCTATGGGACTCGATTAGAGGAGKCCCCAGAGGCATCCAGGAGAT
GCTTTACACAGKGGAGCTCTCTGATCAAGTAAAWGCAGGGAATWCTGCTTTC
TACATCCTCTCATAAGAGAACCACAGCCCAGCTCAGCATATGAGWGACTGAG
GKTTTCTGAAGKAAGGCAACTTGTTGAATCGYATTDAGCTATGCATCGACCC

FIG. 9(a)

(Continuation of SEQ ID NO:7)

AATTTTTACACTGCATCCTTTTCCCCCATATAACTTTTGGAGAAACCCACTTTA
GGATACATCTTCCACCTCATAGGATGCCAGGAAATCAACTGAGTTCAAAGAT
GAGAAACAACTTTGAAAAGTTAAATAAAAGAAATTTAAATTTAAAGAAMCTC
CTCACTTAGTAAGGAATATATGACCAAATAGAAATMCATGTATCTTGAAGAA
TTGAAGAATCAGGCTTTAACGTGGAAGAGGCCTGGATGTWATCCMCCCCATC
ATCTTAGTGTAGCAATGGGGAGGCTMARACCCAGAGTGGGCGAGAGAGTTGT
CTCCTGCGACTCAGCAGCTTGGAGGMATAGATGGGGCAAGATCCTAGGGCTS
TGACTCACCGSCAGCTTCTCTTCCAACAGTAGATGGGTTGGGACAGAAAAGG
TTAAATAGGGTSAAGSAKCTWRCCMCASAYTCCAGTGKGAGACTGTGRGGTC
ATCCTCCTTGTAGRGCATGAKCCCAGCAGGGCTGRGAGACAARGCTGTGCTG
TTACTTCTGGCTACAGTAGKAAGAAAGAGAGACAAAATGCYTGAGWYCMGG
GGGYYCYCTGGATCCAGGGCAKGCTGRAGTGTCCACCCTCCTCCTAATGTAG
TCCTCWCCCCTTCCTGATGTTTCAGAATGAAGGACTCGGCATTGAAGGTGCTT
TATCTGCATAATAACCAGCTTCTAGCTGGAGGGCTGCATGCAGGGAAGGTCA
TTAAAGGTYGGTRATGAAACATGACCCACTTTCCKKGGKCTCTATACACTCTC
AGGGGAGGGGGCCTGAAGAGGGCTTAGAATAGTCATACAGATTAKCATAGG
CCTACRGAGCCCAGGCATTAGGGCAGHACAAACCAGGCTCTAAGCAAAGGC
AAATAAAATACTACACCTMTCAGCAAAGTGAAGACACACGCTCTGGGGCCA
CCTGAAGCTTYTGTGCAGAAGTGAGAATGTTTTCCAAKAKGCTTGTCTTGTYA
TTCCCTTACAGGTAGATWTAGGTCAAGCATTGCATTCCTGGGAGCCAGTAA
GTACCAAGGAGAGAACTAACGTAGATTCTCTATACCTTTTTTCCCATATGGGA
GWGGGTTTCTGCCTCTCCACCCTGGGTCCCCTCTGCTCTCTGAAGATCCTCAG
TCACTTAGAGTGGAGGGACCCAGAGAACAGGTGGCATTGWTGGACCTCCTGC
TTGCTCACTMTGCMCCATGCACTGCAACAGGTCCCTCTSTAAAATAGTTYGC
ACCTGCCCACCTGGGGCACCCTTGCTGAGCWCAGATGCCAGGTAGATCCKTC
AGCTAGGCCATATGTGTATGYGTGTGCTTACTGGTGKATGDATGTGTGCATSC
AGGCATATATGTGTRARCATATGTGTSCATGCATGTATCTGTATGTAACCATG
TATGTGTRAGTGCAGKTATGTAGGTATGASCATGTGTGTGAATATGTATATGT
GTSCATGCATGTATCTGTGCATGTATGATCTGATGTATGTGGGTGGTGAGGGR
ATGTACAGAGAGGAATGAGACCCTCTTTTGCTCTCAGCARCCTCACAGGGTG
TAGAAAGTTGTCCAAMCAATTCCAAAGGGGGCTTATTAAGACAGGGTTCAG
AAAAAGGCCTGAGACCCAAGGGGCATTAAAGGAGGGGGTTGAGTCTATTTTG
GGTTGTAGAGGCTTGAAGATTTGMCCCTGAAYTAGAGGGTGGAGTGGAGGTG
GTACAATGTGCTTCCATGCCTTGATGTCCACTCTGGGCCAGTGGACAGGAGA
ANCCATGTMATGCCAGCTGCTRAGAAGCCTCCCTTCTGCCCAGCCTGGGGGC
AGGCCGTCTCACAGCAGTCYTGTGCCATAGARSGCAGGACARGGARAAAAGA

FIG. 9(b)

(Continuation of SEQ ID NO:7)

AGGAAAGGCATCCAGGCCYTGCATCTGGCNTTTTTCCCACAGGTGAAGAGAT
CAAGCGTGGTCCCCAATCGGTGGCTGGATGCCAGCCTGTCCCCGTCATCTTG
GGTGTCCAGGGTGGAAGCCAGTGCCTGTCATGTGGGGTGGGGCAGGAGCCGA
CTCTTAACACTAGAGGTGAGACTTGGGGCATCCTCACTGGGGACTCAGCCAC
AGATGCTGAGCCTACTGAAGCCGGGCAGYCCACAGCCYTGGTGCTGTGGGAC
ACCCTAGCAGGATTCTGTTGATGGCAGCTTTGCCTCCTCCMTAAGGATCCTGC
CCAGCCCTCCCTCTGCCCCTGCTTCTGCCCTCACCTGACCTCCCCTCCTCTGCC
GGCAGCCAGTGAACATCATGGAGCTCTATCTTGTGCCAAGGAATCCAAGAG
CTTCACCTTCTACCGGCGGGACATGGGGCTCACCTCCAGCTTCGAGTCGGCTG
CCTACCCGGGCTGGTTCCTGTGCACGGTGCCTGAAGCCGATCAGCCTGTCAG
ACTCACCCAGCTTCCCGAGAATGGTGGCTGGAATGCCCCCATCACAGACTTCT
ACTTCCAGCAGTGTGACTAGGGCAACGTGCCCCCAGAACTCCCTGGGCAGA
GCCAGCTCGGGTGAGGGGTGAGTGGAGGAGACCCATGGCGGACAATCACTCT
CTCTGCTCTCAGGACCCCCACGTCTGACTTAGTGGGCACCTGACCACTTGTC
TTCTGGTTCCCAGTTTGGATAAATTCTGAGATTTGGAGCTCAGTCCACGGTCC
TCCCCCACTGGATGGTGCTACTGCTGTGGAACCTTGTAAAACCATGTGGGGT
AAACTGGGAATAACATGAAAAGATTTCTGTGGGGGTGGGGTGGGGAGTGGT
GGGAATCATTCCTGCTTAATGGTAACTGACAAGTGTTACCCTGAGCCCCGCA
GGCCAACCCATCCCCAGTTGAGCCTTATAGGGTCAGTAGCTCTCCACATGAA
GTCCTGTCACTCACCACTGTGCAGGAGAGGGAGGTGGTCATAGAGTCAGGGA
TCTATGGCCCTTGGCCCAGCCCCACCCCCTTCCCTTTAATCCTGCCACTGTCAT
ATGCTACCTTTCCTATCTCTTCCCTCATCATCTTGTTGTGGGCATGAGGAGGTG
GTGATGTCAGAAGAAATGGCTCGAGCTCAGAAGATAAAGATAAGTAGGGT
ATGCTGATCCTCTTTTAAAAACCCAAGATACAATCAAAATCCCCAGATGCTG
GTCTCTATTCCCATGAAAAGTGCTCATGACATATTGAGAAGACCTACTTACA
AAGTGGCATATATTGCAATTTATTTAATTAAAAGATACCTATTTATATATTTC
TTTATAGAAAAAAGTCTGGAAGAGTTTACTTCAATTGTAGCAATGTCAGGGTGGT
GGCAGTATAGGTGATWTTTCTTTTAATTCTGTTAATTTATCTGTATTTCCT
AATTTTTCTACAATGAAGATGAATTCCTTGTATAAAAATAAGAAAAGAAATT
AATCTTGAGGTAAGCAGAGCAGACATCATCTCTGATKGCCTCAGCCTCCACTT
CCCCAGAGTAAATTCAAATTGAATCGAGCTCTGCTGCTCTGGTTGGTTGTAGT
AGTGATCAGGAAWCAGATCTCAGCAAAGCCACTGAGGAGGAGGCTGTGATG
AGTTTGTGTGGCTGGAATCTCTGGGTAAGGAACTTAAAGAACAAAAATCATC
TGGTAATTCTTTCCTAGAAGGATCACAGCCCTGGGATTCCAAGGCATTGGAT
CCAGTCTCTAAGAAGGCTGCTGTACTGGTTGAATTGTGTCCCCCTCAAATTCA
CATCCTTCTTGGAATCTCAGTCTGTGAGTTTATTTGGAGATAAGGTCTCTGCA
GATGTAGTTAGTTAAGACAAGGTCATGCTGGATGAAGGTAGACCTAAATTYA
ATATGACTGGTTTYCTTGTATGAAAAGGAGAGGACACAGAGACAGAGGAGA
CGCGGGGAAGACTATGTAAAGATGAAGGCAGAGATCGGAGTTTTGCAGCCAC
AA

FIG. 9(c)

(SEQ ID NO:8)

```
AATATTGACAGTATGCACAGTCATAGTTTCATTTTACTTATTATTTATTTATTTATTGAGGCAG
AAGTCTAGCTCTCTTCTGTCATCCAGCTGGGAGTACAGTGGCTCAATCTTGGCTCACCGCA
ATCTCACCTCCAGGTTCAAGCAATTCTCACACCTCAGCCTCCTGAGTAGCTTGGATTACAA
ATGTGCACTACAACCCGGCTAATTTTGTGTTTTCAGTAAAGATGGGGTTTTGCCATGTTGG
CCAGGCTTGTCTCATTTCATCTTATTTCTACTGTCATTCCATTTGGTCAATTTGTAATTTAATA
ATTTTGTACAAGGCAGTTTCTACATTAATTTTATTTTTCTGAAAAGTGTCTATCATATTAGTG
GCATTATGAAAATCGTAGATTATTTCTGTGTTTTGAACAACTTGATATTTATTTATTCTTGA
ACACTTGTAGGACCTCTTGGCTCATATGTCTGAATACCATTTCTTTAAAATGTACGCTTTAAC
ATGTATACATATGTAACAAACCTGCACATTGTACACATGTATCCTAAAACTTAAAGTATAATA
ATAATAATAAAAGAAAAAGAAAATAAAACTTAAAAAAATAAAGTGTATGCTTTAACAATAA
ATTATTAATAAATAGTTATCTGTGTTATTCAAGATATAATTAAATTGTTTTTGTGCACTGACC
CTTACCTTTATTTCAGATCCATCACAGAGAGTGCATGGAGGTATTTAAACTGCATTACTGTT
TCACAATTAAGTATTATCTTTATCAATTAGGATTCAAGAAAGATCACTTACAGAATTATAGAT
GGCATGAGCTAGATTTTACTTTCTAAAGAAATAACCAGATACATGAGCAAAGATGTTAATAC
AAAGATGTTTGTCACAACATGGTTTTCAATAGCAAAAAAGAGAGAAAATATATAAAAGAC
AAATAACAGTGGATAGGTTTCAATAAATAATGTTACAGTGATACAGTTAAATACTATACAGCT
ATTGAAGCATGTCATTATTCATATTTAGTATGGAAAGATATTTTGCTATTTTGCTACATGAAA
AAATGAGGTTGGAAAAAGTATAGGTTTTGTGAATCTGTTGTATGAAAGCTGTCTTATAGTTA
CATGTGTATGTGTGTGGAGGAAAAAGTGTTGTCATTGGTTTTCTGATGATGCACTCAGAAA
AGACAAGTATTCACATTTTTCTTGTGGCTGATCTGGATTTTCAGGTTTTTCTACAATGAACA
TGTAGGCTGAACATTCCCTAAGCAGGAGAGTCCCACCTCTAACATCTCCTGTAGGCCTGGC
AATGGCAGGCAGGAAAGACAGAGGAAGGAAGGAGGGAGAAGGGAAGGAGTGAAGGAAG
GAGTGAAAAAGGTAAGGAAGAAAGGGAATAGGGGAGGAAGGGAGGAAATGGGAAGGGAA
AGAAGGAAAKGAAGGGAAAGAGGGAGGGGAAGAAAGGAAGGGGAAAAGGGAGGGAGTG
AGTTGAATGAAAGATGGAAAGAAGGAAGAAAGGGAGGGAGGCAGGGAGGAAAGAAAGTT
GCGCTTCCCTTGAGCTGCCCATGGGCACCTGACTCTTAGGGTCTGAAAGGCCCTGAGAT
GCAAAAGCCTAGTGCTCACAAAGAGCTGGAAAGCCTCAAGGAAGTTCTTCAATATTTCTGG
AAGGAAACTGTCTCCAGAAGCTTCCCTCCCCACGACAGATAATGAGCAGCAAGTGCTTCTG
GCGACTTAGGGTGATGTGAAATTCACGCTGGGAATCCTGCTCCTCCTCAGGTCCTGGCAA
GTTTCAGGGCCCCTCCCTAGGCCTTACTTAAAAGGCTGAGGCATCCTTGGAGGAACAGGC
AGACTCCACAGCTCCCGCCAGGAGAAAGGAACATTCTGAGGTATGCTCTGGGGCGCTGGT
GGTACCGGAGCTCTCTCCTGACCCCAGACCCAGAATCTGCTCCGTGGAGGCTGTTCACAT
GCTGGGGAGCTCGGTGCAGCTGCTTGCTCCCCAGACCCCAGCCAACTCAGCCTCTCTCTC
CATGATTTTCTGTTGTTTATTCCAAAATAGGGGAGTCTACACCCTGTGGAGCTCAAGATGGT
CCTGAGTGGGGCGCTGTGCTTCCGGTGAGTGTATGAGGCCCTGGTTTGGTGGTGTCCTC
CGGAGGAAGTGAGTTCTGGATAGACCCGTTGTCCAGCTCTGAGCAGGAGGGAGGAAGGG
AGGGGGCTGCCATTGCAGCTGGGAAATTGTGACCAGCACCTCATTGCTCTTAGAGTTTTCC
CAGCCTTTTTCAAATAGGGGCAGGACTGGGGCAGGCCATCTCACAAGGGGTCCCTGATGC
TGAGGGGACAAGTGAACCTCCCAGTCTAGAGCTCCAGCCAAGTCTATCCAAGGTGGGAA
CGGGGGCCAGGATCCCTGCTCAGAGCTCCGCCATTGTCCCCATCACAGTGAATGGATGT
AAGCTCACCCACTCTGTGCCCCTACCTCCTGCTACTCTTTGGGGGATAATAATAAAACAA
AAACCATTACCATCAGCCAAGTCTGTCCACCCACTGGCATGTACCAAGCCAGACACTCTGC
CGTGTTCTGGGCTTAACAACCAGAGGATGAGAGTGGTCCTTTCTCTCAGTCTAATAAAGCA
CTTCCCACGATGTGTTCTATGGGACTCGATTAGAGGAGTCCCACAGAGGCATCCAGGAGA
TGCTTTACACAGTGGAGCTCTCTGATCAAGTAAATGCAGGGAATTCTGCTTTCTACATCCTC
TCATAAGAGAACCACAGCCCAGCTCAGCATATGAGTGACTGAGGKTTTCTGAAGTAAGGCA
ACTTGTTGAATCGYATTTAGCTATGCATCGACCCAATTTTTACACTGCATCCTTTTCCCCCAT
ATAACTTTTGGAGAAACCCACTTTAGGATACATCTTCCACCTCATAGGATGCCAGGAAATCA
```

FIG. 10(a)

(Continuation of SEQ ID NO:8)

```
ACTGAGTTCAAAGATGAGAAACAACTTTGAAAAGTTAAATAAAAGAAATTTAAATTTAAAGAA
ACTCCTCACTTAGTAAGGAATATATGACCAAATAGAAATACATGTATCTTGAAGAATTGAAG
AATCAGGCTTTAACGTGGAAGAGGCCTGGATGTTATCCAACCCATCATCTTAGTGTAGCAA
TGGGGAGGCTCAGACCCAAGAGTGGGCGAGAGAGTTGTCTCCTGCGACTCAGCAGCATT
GGAGGCATAGATGGGGCAAGATCCTAGGGCTCTGACTCACCGAGCAGCTTCTCTTCCAAC
AGGAGATGGGTTGGGGCAGAAAAGGTTGAATAGGGTGAAGGAGCAAACCACAGACTCCA
GTGGGAGACTGTGGGGTCATCCTCCTTGTAGGGCATGAGCCCAGCAGGGCTGGGAGACA
AGGCTGTGCTGTTACTTCTGGCACAGTAGGAAGAAAGAGAGACAAAATGCCTGAGATCAG
GGGGTTCTCTGGATCCAGGGCATGCTGGAGTGTCCACCCTCCTCCTAATGTAGTCCTCAC
CCCTTCCTGATGTTTCAGAATGAAGGACTCGGCATTGAAGGTGCTTTATCTGCATAATAACC
AGCTTCTAGCTGGAGGGCTGCATGCAGGGAAGGTCATTAAAGGTTGGTGATGAAACATGA
CCCACTTTCCTTGGTCTCTATACACTCTCAGGGGAGGGGGCCTGAAGAGGGCTTAGAATA
GTCATACAGATTAGCATAGGCCTACAGAGCCCAGGCATTAGGGCAGCACAAACCAGGCTC
TAAGCAAAGGCAAATAAATACTACACCTCTCAGCAAAGTGAAGACACACGCTCTGGGGCC
ACCTGAAGCTTCTGTGCAGAAGTGAGAATGTTTTCCAAGAGGCTTGTCTTGTCATTCCCTTA
CAGGTAGATWTAGGTCAAGCATTGCATTCCCTGGGAGCCAGTAAGTACCAAGGAGAGAAC
TAACGTAGATTCTCTATACCTTTTTTCCCATATGGGAGTGGGTTTCTGCCTCTCCACCCTGG
GTCCCCTCTGCTCTCTGAAGATCCTCAGTCACTTAGAGTGGAGGGACCCAGAGAACAGGT
GGCATTGTTGGACCTCCTGCTTGCTCACTCTGCCCCATGCACTGCAACAGGTCCCTCTCTA
AAATAGTTYGCACCTGCCCACCTGGGGCACCCTTGCTGAGCACAGATGCCAGGTAGATCC
TTCAGCTAGGCCATATGTGTATGTGTGCTTACTGGTGTATGTATGTGTGCATGCAGGCA
TATATGTGTGAGCATATGTGTGCATGCATGTATCTGTATGTAACCATGTATGTGTGAGTGCA
GGTATGTAGGTATGAGCATGTGTGTGAATATGTATATGTGTGCATGCATGTATCTGTGCAT
GTATGATCTGATGTATGTGGGTGGTGAGGGGATGTACAGAGAGGAATGAGACCCTCTTTT
GCTCTCAGCAACCTCACAGGGTGTAGAAAGTTGTCCAAACAATTCCAAAGGGGGCTTATT
AAGACAGGGTTCAGAAAAAGGCCTGAGACCCAAGGGGCATTAAAGGAGGGGGTTGAGTC
TATTTTGGGTTGTAGAGGCTTGAAGATTTGACCCTGAACTAGAGGGTGGAGTGGAGGTGG
TACAATGTGCTTCCATGCCTTGATGTCCACTCTGGGCCAGTGGACAGGAGAAGCCATGTC
ATGACAGCTGCTGAGAAGCCTCCCTTCTGCCCAGCCTGGGGGCAGGCCGTCTCACAGCA
GTCCTGTGCCCTAGAGCCCAGGACAGGGGAAGAAGGAGGGAAAGGCATCCAGGGCCCTG
CATCTGGCCTCTTTCCCACAGGTGAAGAGATCAGCGTGGTCCCCAATCGGTGGCTGGATG
CCAGCCTGTCCCCCGTCATCCTGGGTGTCCAGGGTGGAAGCCAGTGCCTGTCATGTGGG
GTGGGGCAGGAGCCGACTCTTAACACTAGAGGTGAGACTTGGGGCATCCTCACTGGGGA
CTCAGCCACAGATGCTGAGCCTACTGAAGCCGGGCAGCCCACAGCCCTGGTGCTGTGGG
ACACCCTAGCAGGATTCTGTTGATGGCAGCTTTGCCTCCTCCCTAAGGATCCTGCCCAGCC
CTCCCTCTGCCCCTGCTTCTGCCCTCACCTGACCTCCCCTCCTCTGCCGGCAGCCAGTGA
ACATCATGGAGCTCTATCTTGGTGCCAAGGAATCCAAGAGCTTCACCTTCTACCGGCGGG
ACATGGGGCTCACCTCCAGCTTCGAGTCGGCTGCCTACCCGGGCTGGTTCCTGTGCACG
GTGCCTGAAGCCGATCAGCCTGTCAGACTCACCCAGCTTCCCGAGAATGGTGGCTGGAAT
GCCCCCATCACAGACTTCTACTTCCAGCAGTGTGACTAGGGCAACGTGCCCCCAGAACT
CCCTGGGCAGAGCCAGCTCGGGTGAGGGTGAGTGGAGGAGACCCATGGCGGACAATC
ACTCTCTCTGCTCTCAGGACCCCCACGTCTGACTTAGTGGGCACCTGACCACTTTGTCTTC
TGGTTCCCAGTTTGGATAAATTCTGAGATTTGGAGCTCAGTCCACGGTCCTCCCCCACTGG
ATGGTGCTACTGCTGTGGAACCTTGTAAAAACCATGTGGGGTAAACTGGGAATAACATGAA
AAGATTTCTGTGGGGTGGGTGGGGAGTGGTGGGAATCATTCCTGCTTAATGGTAACT
GACAAGTGTTACCCTGAGCCCCGCAGGCCAACCCATCCCCAGTTGAGCCTTATAGGGTCA
GTAGCTCTCCACATGAAGTCCTGTCACTCACCACTGTGCAGGAGAGGGAGGTGGTCATAG
AGTCAGGGATCTATGGCCCTTGGCCCAGCCCCACCCCCTTCCCTTTAATCCTGCCACTGTC
ATATGCTACCTTTCCTATCTCTTCCCTCATCATCTTGTTGTGGGCATGAGGAGGTGGTGAT
```

FIG. 10(b)

(Continuation of SEQ ID NO:8)

```
GTCAGAAGAAATGGCTCGAGCTCAGAAGATAAAAGATAAGTAGGGTATGCTGATCCTCTTT
TAAAAACCCAAGATACAATCAAAATCCCAGATGCTGGTCTCTATTCCCATGAAAAAGTGCTC
ATGACATATTGAGAAGACCTACTTACAAAGTGGCATATATTGCAATTTATTTTAATTAAAAGA
TACCTATTTATATATTTCTTTATAGAAAAAAGTCTGGAAGAGTTTACTTCAATTGTAGCAATG
TCAGGGTGGTGGCAGTATAGGTGATTTTTCTTTTAATTCTGTTAATTTATCTGTATTTCCTAA
TTTTTCTACAATGAAGATGAATTCCTTGTATAAAAATAAGAAAAGAAATTAATCTTGAGGTAA
GCAGAGCAGACATCATCTCTGATTGCCTCAGCCTcCACTTCCCCAGAGTAAATTCAAATTGA
ATCGAGCTCTGCTGCTCTGGTTGGTTGTAGTAGTGATCAGGAATCAGATCTCAGCAAAGCC
ACTGAGGAGGAGGCTGTGATGAGTTTGTGTGGCTGGAATCTCTGGGTAAGGAACTTAAAG
AACAAAAATCATCTGGTAATTCTTTCCTAGAAGGATCACAGCCCCTGGGATTCCAAGGCATT
GGATCCAGTCTCTAAGAAGGCTGCTGTACTGGTTGAATTGTGTCCCCCTCAAATTCACATC
CTTCTTGGAATCTCAGTCTGTGAGTTTATTTGGAGATAAGGTCTCTGCAGATGTAGTTAGTT
AAGACAAGGTCATGCTGGATGAAGGTAGACCTAAATTCAATATGACTGGTTTCCTTGTATG
AAAAGGAGAGGACACAGAGACAGAGGAGACGCGGGGAAGACTATGTAAAGATGAAGGCA
GAGATCGGAGTTTTGCAGCCACAAGCTAAGAAACACCAAGGATTGTGGCAACCATCAGAA
GCTTGGAAGAGGCAAAGAAGAATTCTTCCCTAGAGGCTTTAGAGGGATAACGGCTCTGCT
GACACCTTAATCTCAGACTTCCAGCCTCCTGAACGAAGAAAGAATAAATTTCGGCTGTTTTA
AGCCACCAAGGATAATTGGTTATGGCAGCTCTAGGAAACTAATACAGCTGCTAAAATGATC
CCTGTCTCCTCGTGTTTACATTCTGTGTGTGTCCCCTCCCACAATGTACCAAAGTTGTCTTT
GTGACCAATAGAATATGGCAGAAGTGATGGCATGCCACTTCCAAGATTAGGTTATAAAAGA
CACTGCAGCTTCTACTTGAGCCCTCTCTCTCTGCCACCCACCGCCCCCAATCTATCTTGGC
TCACTCGCTCTGGGGGAAGCTAGCTTCCATGCTATGAGCAGGCCTATAAAGAGACTTATGT
GGTAAAAAATGAAGTCTCCTGCCCACAGCCACATTAGTGAACCTAGAAGCAGAGACTCTGT
GAGATAATCAATGTTTGTTGTTTTAAGTTGCTCAGTTTTGGTCTAACTTGTTATGCAGCAATA
GATAAATAATATGCAGAGAAAGAGAAACAAATGCATTTGTTTTATTATTGCAATTTTCTCCAA
TATTTTTTATTTTCTTTCTCACAATGAACAACTATCCTTCATTTACCCAAATATTCTATTTAAAA
GCTAATAATACAGCATTTGTTGAGTCATCTGGTTCTGCAAGATTGAGATCCTCTTGTCCTAT
GTGCCAGGAATGAACTCCAGTGCCCCACCCAAACCCTGGGGAATG
```

FIG. 10(c)

SEQUENCE LISTING

```
<160> NUMBER OF SEQ ID NOS: 30

<210> SEQ ID NO 1
<211> LENGTH: 357
<212> TYPE: DNA
<213> ORGANISM: Homo sapiens
<220> FEATURE:
<221> NAME/KEY: misc_feature
<222> LOCATION: (1)...(357)
<223> OTHER INFORMATION: n = A,T,C or G

<400> SEQUENCE: 1
ccgactctaa cactagagcc agtgaacatc atggagctct atcttggtgc caaggaatcc      60
aagagcttca ccttctaccg gcgggacatg gggctcacct ccagcttcga gtcggctgcc     120
tacccgggct ggttcctgtg cacggtgcct gaagccgatc agcctgtcag actcacccag     180
cttcccgaga atggtggctg gaatgccccc atcacagact tctacttcca gcagtgtgac     240
tagggcaacg tgcccccag aactccctgg gcagagccag ctcggntgan gggngagngn      300
nnnnnnnnnn ngnnnnnnnn nnnnnnnnnn nnnnnnnna nnnnnnnnnn nnnnnng        357

<210> SEQ ID NO 2
<211> LENGTH: 985
<212> TYPE: DNA
<213> ORGANISM: Homo sapiens
<220> FEATURE:
<221> NAME/KEY: CDS
<222> LOCATION: (1)...(240)

<400> SEQUENCE: 2 ccg act cta aca cta gag cca gtg aac atc atg gag ctc tat ctt ggt       48
Pro Thr Leu Thr Leu Glu Pro Val Asn Ile Met Glu Leu Tyr Leu Gly
  1               5                  10                  15 gcc aag gaa tcc aag agc ttc acc ttc tac cgg cgg gac atg ggg ctc       96
Ala Lys Glu Ser Lys Ser Phe Thr Phe Tyr Arg Arg Asp Met Gly Leu
             20                  25                  30 acc tcc agc ttc gag tcg gct gcc tac ccg ggc tgg ttc ctg tgc acg      144
Thr Ser Ser Phe Glu Ser Ala Ala Tyr Pro Gly Trp Phe Leu Cys Thr
         35                  40                  45 gtg cct gaa gcc gat cag cct gtc aga ctc acc cag ctt ccc gag aat      192
Val Pro Glu Ala Asp Gln Pro Val Arg Leu Thr Gln Leu Pro Glu Asn
     50                  55                  60 ggt ggc tgg aat gcc ccc atc aca gac ttc tac ttc cag cag tgt gac      240
Gly Gly Trp Asn Ala Pro Ile Thr Asp Phe Tyr Phe Gln Gln Cys Asp
```

-continued

```
                65                 70                 75                 80 taggggcaacg tgcccccccag aactccctgg gcagagccag ctcgggtgag gggtgagtgg      300
aggagaccca tggcggacaa tcactctctc tgctctcagg accccacgt ctgacttagt        360 gggcacctga ccactttgtc ttctggttcc cagtttggat aaattctgag atttggagct      420
cagtccacgg tcctccccca ctggatggtg ctactgctgt ggaaccttgt aaaaaccatg      480
tggggtaaac tgggaataac atgaaaagat ttctgtgggg gtggggtggg ggagtggtgg      540
gaatcattcc tgcttaatgg taactgacaa gtgttaccct gagccccgca ggccaaccca      600
tccccagttg agccttatag ggtcagtagc tctccacatg aagtcctgtc actcaccact      660
gtgcaggaga gggaggtggt catagagtca gggatctatg gcccttggcc cagccccacc      720
cccttccctt taatcctgcc actgtcatat gctaccttc ctatctcttc cctcatcatc       780
ttgttgtggg catgaggagg tggtgatgtc agaagaaatg gctcgagctc agaagataaa      840
agataagtag ggtatgctga tcctctttta aaaacccaag atacaatcaa atcccagat       900 gctggtctct attcccatga aaaagtgctc atgacatatt gagaagacct acttacaaag      960
tggcatatat ttgcaattaa tttta                                            985
```

<210> SEQ ID NO 3
<211> LENGTH: 80
<212> TYPE: PRT
<213> ORGANISM: Homo sapiens

<400> SEQUENCE: 3

```
Pro Thr Leu Thr Leu Glu Pro Val Asn Ile Met Glu Leu Tyr Leu Gly
1               5                   10                  15

Ala Lys Glu Ser Lys Ser Phe Thr Phe Tyr Arg Arg Asp Met Gly Leu
            20                  25                  30

Thr Ser Ser Phe Glu Ser Ala Ala Tyr Pro Gly Trp Phe Leu Cys Thr
        35                  40                  45

Val Pro Glu Ala Asp Gln Pro Val Arg Leu Thr Gln Leu Pro Glu Asn
    50                  55                  60

Gly Gly Trp Asn Ala Pro Ile Thr Asp Phe Tyr Phe Gln Gln Cys Asp
65                  70                  75                  80
```

<210> SEQ ID NO 4
<211> LENGTH: 1282
<212> TYPE: DNA
<213> ORGANISM: Homo sapiens
<220> FEATURE:
<221> NAME/KEY: CDS
<222> LOCATION: (73)...(537)

<400> SEQUENCE: 4

```
ccacgcgtcc gcacagctcc cgccaggaga aaggaacatt ctgaggggag tctacaccct       60
gtggagctca ag atg gtc ctg agt ggg gcg ctg tgc ttc cga atg aag gac    111
              Met Val Leu Ser Gly Ala Leu Cys Phe Arg Met Lys Asp
              1               5                   10 tcg gca ttg aag gtg ctt tat ctg cat aat aac cag ctt cta gct gga    159
Ser Ala Leu Lys Val Leu Tyr Leu His Asn Asn Gln Leu Leu Ala Gly
        15                  20                  25 ggg ctg cat gca ggg aag gtc att aaa ggt gaa gag atc agc gtg gtc   207
Gly Leu His Ala Gly Lys Val Ile Lys Gly Glu Glu Ile Ser Val Val
30                  35                  40                  45 ccc aat cgg tgg ctg gat gcc agc ctg tcc ccc gtc atc ctg ggt gtc   255
Pro Asn Arg Trp Leu Asp Ala Ser Leu Ser Pro Val Ile Leu Gly Val
                50                  55                  60
```

-continued

```
cag ggt gga agc cag tgc ctg tca tgt ggg gtg ggg cag gag ccg act      303
Gln Gly Gly Ser Gln Cys Leu Ser Cys Gly Val Gly Gln Glu Pro Thr
             65                  70                  75 cta aca cta gag cca gtg aac atc atg gag ctc tat ctt ggt gcc aag      351
Leu Thr Leu Glu Pro Val Asn Ile Met Glu Leu Tyr Leu Gly Ala Lys
         80                  85                  90 gaa tcc aag agc ttc acc ttc tac cgg cgg gac atg ggg ctc acc tcc      399
Glu Ser Lys Ser Phe Thr Phe Tyr Arg Arg Asp Met Gly Leu Thr Ser
     95                 100                 105 agc ttc gag tcg gct gcc tac ccg ggc tgg ttc ctg tgc acg gtg cct      447
Ser Phe Glu Ser Ala Ala Tyr Pro Gly Trp Phe Leu Cys Thr Val Pro
110                 115                 120                 125 gaa gcc gat cag cct gtc aga ctc acc cag ctt ccc gag aat ggt ggc      495
Glu Ala Asp Gln Pro Val Arg Leu Thr Gln Leu Pro Glu Asn Gly Gly
                130                 135                 140 tgg aat gcc ccc atc aca gac ttc tac ttc cag cag tgt gac              537
Trp Asn Ala Pro Ile Thr Asp Phe Tyr Phe Gln Gln Cys Asp
                145                 150                 155 tagggcaacg tgcccccag aactccctgg gcagagccag ctcgggtgag gggtgagtgg      597
aggagaccca tggcggacaa tcactctctc tgctctcagg acccccacgt ctgacttagt     657
gggcacctga ccactttgtc ttctggttcc cagtttggat aaattctgag atttggagct     717
cagtccacgg tcctccccca ctggatggtg ctactgctgt ggaaccttgt aaaaaccatg     777
tggggtaaac tggaataac atgaaaagat ttctgtgggg gtggggtggg ggagtggtgg      837
gaatcattcc tgcttaatgg taactgacaa gtgttaccct gagccccgca ggccaaccca     897
tccccagttg agccttatag ggtcagtagc tctccacatg aagtcctgtc actcaccact     957
gtgcaggaga gggaggtggt catagagtca gggatctatg gcccttggcc cagccccacc    1017
cccttccctt taatcctgcc actgtcatat gctacctttc ctatctcttc cctcatcatc    1077
ttgttgtggg catgaggagg tggtgatgtc agaagaaatg gctcgagctc agaagataaa    1137
agataagtag ggtatgctga tcctctttta aaaaacccaag atacaatcaa atcccagat    1197
gctggtctct attcccatga aaaagtgctc atgacatatt gagaagacct acttacaaag    1257
tggcatatat ttgcaattaa tttta                                          1282
```

<210> SEQ ID NO 5
<211> LENGTH: 155
<212> TYPE: PRT
<213> ORGANISM: Homo sapiens

<400> SEQUENCE: 5

```
Met Val Leu Ser Gly Ala Leu Cys Phe Arg Met Lys Asp Ser Ala Leu
 1               5                  10                  15

Lys Val Leu Tyr Leu His Asn Asn Gln Leu Leu Ala Gly Gly Leu His
             20                  25                  30

Ala Gly Lys Val Ile Lys Gly Glu Glu Ile Ser Val Val Pro Asn Arg
         35                  40                  45

Trp Leu Asp Ala Ser Leu Ser Pro Val Ile Leu Gly Val Gln Gly Gly
     50                  55                  60

Ser Gln Cys Leu Ser Cys Gly Val Gly Gln Glu Pro Thr Leu Thr Leu
 65                  70                  75                  80

Glu Pro Val Asn Ile Met Glu Leu Tyr Leu Gly Ala Lys Glu Ser Lys
                 85                  90                  95

Ser Phe Thr Phe Tyr Arg Arg Asp Met Gly Leu Thr Ser Ser Phe Glu
            100                 105                 110
```

```
Ser Ala Ala Tyr Pro Gly Trp Phe Leu Cys Thr Val Pro Glu Ala Asp
        115                 120                 125

Gln Pro Val Arg Leu Thr Gln Leu Pro Glu Asn Gly Gly Trp Asn Ala
    130                 135                 140

Pro Ile Thr Asp Phe Tyr Phe Gln Gln Cys Asp
145                 150                 155

<210> SEQ ID NO 6
<211> LENGTH: 2648
<212> TYPE: DNA
<213> ORGANISM: Homo sapiens

<400> SEQUENCE: 6
cacagctccc gccaggagaa aggaacattc tgagggagt ctacaccctg tggagctcaa      60
gatggtcctg agtggggcgc tgtgcttccg aatgaaggac tcggcattga aggtgcttta    120
tctgcataat aaccagcttc tagctggagg gctgcatgca gggaaggtca ttaaaggtga    180
agagatcagc gtggtcccca tcggtggct ggatgccagc ctgtccccg tcatcctggg     240 tgtccagggt ggaagccagt gcctgtcatg tggggtgggg caggagccga ctctaacact    300
agagccagtg aacatcatgg agctctatct tggtgccaag aatccaaga gcttcacctt     360 ctaccggcgg gacatgggc tcacctccag cttcgagtcg gctgcctacc cgggctggtt    420
cctgtgcacg gtgcctgaag ccgatcagcc tgtcagactc acccagcttc ccgagaatgg    480
tggctggaat gcccccatca gacttctca cttccagcag tgtgactagg caacgtgcc     540 ccccagaact ccctgggcag agccagctcg ggtgaggggt gagtggagga gacccatggc    600
ggacaatcac tctctctgct ctcaggaccc ccacgtctga cttagtgggc acctgaccac    660
tttgtcttct ggttcccagt ttggataaat tctgagattt ggagctcagt ccacggtcct    720
cccccactgg atggtgctac tgctgtggaa ccttgtaaaa accatgtggg gtaaactggg    780
aataacatga aaagatttct gtgggggtgg ggtgggggag tggtgggaat cattcctgct    840
taatggtaac tgacaagtgt taccctgagc cccgcaggcc aacccatccc cagttgagcc    900
ttatagggtc agtagctctc cacatgaagt cctgtcactc accactgtgc aggagaggga    960
ggtggtcata gagtcaggga tctatggccc ttggcccagc cccacccct tccctttaat    1020 cctgccactg tcatatgcta cctttcctat ctcttccctc atcatcttgt tgtgggcatg   1080
aggaggtggt gatgtcagaa gaatggctc gagctcagaa gataaaagat aagtagggta    1140
tgctgatcct cttttaaaaa cccaagatac aatcaaaatc ccagatgctg tctctattc    1200 ccatgaaaaa gtgctcatga catattgaga agacctactt acaaagtggc atatatttgc    1260
aattaatttt aattaaaaga tacctattta tatttctt tatagaaaaa agtctggaag    1320
agtttacttc aattgtagca atgtcagggt ggtggcagta taggtgattt ttctttaat    1380 tctgttaatt tatctgtatt tcctaattt tctacaatga agatgaattc cttgtataaa    1440
aataagaaaa gaaattaatc ttgaggtaag cagagcagac atcatctctg attgtcctca    1500
gcctccactt ccccagagta aattcaaatt gaatcgagct ctgctgctct ggttggttgt    1560
agtagtgatc aggaaacaga tctcagcaaa gccactgagg aggaggctgt gctgaagttg    1620
tgtggctgga atctctgggt aaggaactta agaacaaaa atcatctggt aattctttcc    1680
tagaaggatc acagccctg ggattccaag gcattggatc cagtctctaa gaaggctgct    1740
gtactggttg aattgtgtcc ccctcaaatt cacatccttc ttggaatctc agtctgtgag    1800
tttatttgga gataaggtct ctgcagatgt agttagttaa gacaaggtca tgctggatga   1860
```

```
aggtagacct aaaattcaata tgactggttt ccttgtatga aaaggagagg acacagagac    1920
agaggagacg cggggaagac tatgtaaaga tgaaggcaga gatcggagtt ttgcagccac    1980
aagctaagaa acaccaagga ttgtggcaac catcagaagc ttggaagagg caaagaagaa    2040
ttcttcccta gaggctttag agggataacg gctctgctga aaccttaatc tcagacttcc    2100
agcctcctga acgaagaaag aataaatttc ggctgtttta agccaccaag gataattggt    2160
tacagcagct ctaggaaact aatacagctg ctaaaatgat ccctgtctcc tcgtgtttac    2220
attctgtgtg tgtcccctcc cacaatgtac caaagttgtc tttgtgacca atagaatatg    2280
gcagaagtga tggcatgcca cttccaagat taggttataa aagacactgc agcttctact    2340
tgagccctct ctctctgcca cccaccgccc ccaatctatc ttggctcact cgctctgggg    2400
gaagctagct gccatgctat gagcaggcct ataaagagac ttacgtggta aaaaatgaag    2460
tctcctgccc acagccacat tagtgaacct agaagcagag actctgtgag ataatcgatg    2520
tttgttgttt taaagttgct cagttttggt ctaacttgtt atgcagcaat agataaataa    2580
tatgcagaga aagagaaaaa aaaaaaaaa aaaaaaaaa aaaaaaaaa aaaaaaaaa    2640 aaaaaaaa                                                           2648

<210> SEQ ID NO 7
<211> LENGTH: 5751
<212> TYPE: DNA
<213> ORGANISM: Homo sapiens
<220> FEATURE:
<221> NAME/KEY: misc_feature
<222> LOCATION: (1)...(5751)
<223> OTHER INFORMATION: n = A,T,C or G

<400> SEQUENCE: 7
cngttaatcc taccactatg agnatgtctt atcatttagt angaagattt ttgcttttg      60 cacatgaaaa ataggttgga aaaagtatag gttttgtgat ctgtgtatga aagctgtcta    120
tagtacatgt gtatgtgtgg gagaaaaagt gttgtcattg gttttctrat gantcactma    180
gaaaagcaag tattcacatt ttttcttgtg gctgtctgat tttcaggttt ttctacaatg    240
acatgtaggc tgancattcc ctargcagag agtcccacyt ctaacatctc ytgtaggcct    300
ggcaakgcag cagaaasnca gaggaaggaa ggaggragaa ggaaggagtg aagraaggag    360
taaaaaggta aggaagaaag ggaatagggr agraagggag raaatgggaa gggaaaraag    420
gaaaggaagg aaagagggag ggaagaaagr aagggaaaag ggagggagtg agtgaatgaa    480
agatggaaag aagraagaaa gggagggagg cagggaggaa agaaagttgc gcttcccttg    540
asctgccatg ggcactgmyt cttagggtct gaaagcccct gagatgcaaa agcctagtgc    600
tcacaaagag ctggaaagcc tcaaggaagt tcttcaatat ttctggaagg aaactgtctc    660
cagaagcttc cctccccacg acagataatg agcagcaagt gcttctggcg acttagggtg    720
atgtgaaatc acgctgggaa tcctgctcct cctcaggtcc tggcagtttc agggcccctc    780
cctaggcctt acttaaaagg ctgaggcatc cttggaggaa caggcagact ccacagctcc    840
cgccaggaga aaggaacatt ctgaggtatg ctctggggcg ctggtggtac cggagctctc    900
tcctgacccc agacccagaa tctgctccgt ggaggctgtt cacatgctgg ggagctcggt    960
gcagctgctt gctccccaga ccccagccaa ctcagcctct ctctccatga ttttctgttg   1020
tttattccaa aataggggag tctacaccct gtggagctca agatggtcct gagtggggcg   1080
ctgtgcttcc ggtgagtgta tgaggccctg gtttggtggt gtcctccgga ggaagtgagt   1140
```

```
tctggataga cccgttgtcc agctctgagc aggagggagg aagggagggg ctgccattgs    1200
rgctgkbaaa ttgtgaccag cacctcattg ctcttagagt tttcccagcc tttttcaaat    1260
aggggcagga ctggggcarg ccatctcaca aggggwccct gatgctgagg gggacaagtg    1320
aacctcccag wctaragctc cagccaagtc tatccaaggt gggaacgggg gccaggatcc    1380
ctgctcagag ctccgccatt gtcccccatc acagtgaatg gatgtaagct cacccactct    1440
gtgcccctac ctycctgcta ctctttgggg ataatwataa aacaaaaacc attaccatca    1500
gccagtytgt mcacccactg gcatgtacca agccagacac tctgccgtgt tctgggctta    1560
acaacagagg atgaaragtg ggcctttctc tcagkctaat aaagvacttc ccacgatgkg    1620
ttctatggga ctcgattaga ggagkcccca gaggcatcca ggagatgctt tacacagkgg    1680
agctctctga tcaagtaaaw gcagggaatw ctgctttcta catcctctca aagagaacc     1740
acagcccagc tcagcatatg agwgactgag gktttctgaa gkaaggcaac ttgttgaatc    1800
gyattdagct atgcatcgac ccaattttta cactgcatcc ttttccccca tataactttt    1860
ggagaaaccc actttaggat acatcttcca cctcatagga tgccaggaaa tcaactgagt    1920
tcaaagatga gaaacaactt tgaaaagtta ataaaagaa atttaaattt aaagaamctc      1980
ctcacttagt aaggaatata tgaccaaata gaaatmcatg tatcttgaag aattgaagaa    2040
tcaggcttta acgtggaaga ggcctggatg twatccmccc catcatctta gtgtagcaat    2100
ggggaggctm aracccagag tgggcgagag agttgtctcc tgcgactcag cagcttggag    2160
gmatagatgg ggcaagatcc tagggctstg actcaccgsc agcttctctt ccaacagtag    2220
atgggttggg acagaaaagg ttaaataggg tsaagsakct wrccmcasay tccagtgkga    2280
gactgtgrgg tcatcctcct tgtagrgcat gakcccagca gggctgrgag acaargctgt    2340
gctgttactt ctggctacag tagkaagaaa gagagacaaa atgcytgagw ycmggggyy     2400
cyctggatcc agggcakgct gragtgtcca ccctcctcct aatgtagtcc tcwcccttc     2460
ctgatgtttc agaatgaagg actcggcatt gaaggtgctt tatctgcata ataaccagct    2520
tctagctgga gggctgcatg cagggaaggt cattaaaggt yggtratgaa acatgaccca    2580
cttccckkgg kctctataca ctctcagggg aggggggcctg aagagggctt agaatagtca    2640
tacagattak cataggccta crgagcccag gcattagggc aghacaaacc aggctctaag    2700
caaaggcaaa taaaatacta cacctmtcag caaagtgaag acacacgctc tggggccacc    2760
tgaagcttyt gtgcagaagt gagaatgttt tccaakakgc ttgtcttgty attcccttac    2820
aggtagatwt aggtcaagca ttgcattccc tgggagccag taagtaccaa ggagagaact    2880
aacgtagatt ctctataccct ttttcccat atgggagwgg gtttctgcct ctccaccctg    2940
ggtcccctct gctctctgaa gatcctcagt cacttagagt ggagggaccc agagaacagg    3000
tggcattgwt ggacctcctg cttgctcact mtgcmccatg cactgcaaca ggtccctcts    3060
taaaatagtt ygcacctgcc cacctggggc acccttgctg agcwcagatg ccaggtagat    3120
ccktcagcta ggccatatgt gtatgygtgt gcttactggt gkatgdatgt gtgcatscag    3180
gcatatatgt gtrarcatat gtgtscatgc atgtatctgt atgtaaccat gtatgtgtra    3240
gtgcagktat gtaggtatga scatgtgtgt gaatatgtat atgtgtscat gcatgtatct    3300
gtgcatgtat gatctgatgt atgtgggtgg tgagggratg tacagagagg aatgagaccc    3360
tcttttgctc tcagcarcct cacagggtgt agaaagttgt ccaamcaatt ccaaggggg     3420
gcttattaag acagggttca gaaaaaggcc tgagacccaa ggggcattaa aggagggggt    3480
tgagtctatt ttgggttgta gaggcttgaa gatttgmccc tgaaytagag ggtggagtgg    3540
```

```
aggtggtaca atgtgcttcc atgccttgat gtccactctg ggccagtgga caggagaanc    3600
catgtmatgc cagctgctra gaagcctccc ttctgcccag cctggggggca ggccgtctca    3660 cagcagtcyt gtgccataga rsgcaggaca rggaraaaag aaggaaaggc atccaggccy    3720
tgcatctggc nttttttccca caggtgaaga gatcaagcgt ggtccccaat cggtggctgg    3780
atgccagcct gtcccccgtc atcttgggtg tccaggtgg aagccagtgc ctgtcatgtg     3840
gggtggggca ggagccgact cttaacacta gaggtgagac ttggggcatc ctcactgggg    3900
actcagccac agatgctgag cctactgaag ccgggcagyc cacagccytg gtgctgtggg    3960
acaccctagc aggattctgt tgatggcagc tttgcctcct ccmtaaggat cctgcccagc    4020
cctccctctg cccctgcttc tgccctcacc tgacctcccc tcctctgccg gcagccagtg    4080
aacatcatgg agctctatct tggtgccaag gaatccaaga gcttcacctt ctaccggcgg    4140
gacatggggc tcacctccag cttcgagtcg gctgcctacc cgggctggtt cctgtgcacg    4200
gtgcctgaag ccgatcagcc tgtcagactc acccagcttc ccgagaatgg tggctggaat    4260
gcccccatca cagacttcta cttccagcag tgtgactagg gcaacgtgcc ccccagaact    4320
ccctgggcag agccagctcg ggtgagggt gagtggagga gacccatggc ggacaatcac     4380
tctctctgct ctcaggaccc ccacgtctga cttagtgggc acctgaccac tttgtcttct    4440
ggttcccagt ttggataaat tctgagattt ggagctcagt ccacggtcct cccccactgg    4500
atggtgctac tgctgtggaa ccttgtaaaa accatgtggg gtaaactggg aataacatga    4560
aaagatttct gtgggggtgg ggtgggggag tggtgggaat cattcctgct taatggtaac    4620
tgacaagtgt taccctgagc cccgcaggcc aacccatccc cagttgagcc ttatagggtc    4680
agtagctctc cacatgaagt cctgtcactc accactgtgc aggagaggga ggtggtcata    4740
gagtcaggga tctatggccc ttggcccagc cccacccccct tccctttaat cctgccactg    4800
tcatatgcta cctttcctat ctcttccctc atcatcttgt tgtgggcatg aggaggtggt    4860
gatgtcagaa gaaatggctc gagctcagaa gataaaagat aagtagggta tgctgatcct    4920
cttttaaaaa cccaagatac aatcaaaatc cccagatgct ggtctctatt cccatgaaaa    4980
agtgctcatg acatattgag aagacctact tacaaagtgg catatattgc aatttatttt    5040
aattaaaaga tacctattta tatatttctt tatagaaaaa agtctggaag agtttacttc    5100
aattgtagca atgtcagggt ggtggcagta taggtgatwt ttctttttaat tctgttaatt    5160 tatctgtatt tcctaattt tctacaatga agatgaattc cttgtataaa aataagaaaa    5220
gaaattaatc ttgaggtaag cagagcgac atcatctctg atkgcctcag cctccacttc     5280
cccagagtaa attcaaattg aatcgagctc tgctgctctg gttggttgta gtagtgatca    5340
ggaawcagat ctcagcaaag ccactgagga ggaggctgtg atgagtttgt gtggctggaa    5400
tctctgggta aggaacttaa agaacaaaaa tcatctggta attctttcct agaaggatca    5460
cagcccctgg gattccaagg cattggatcc agtctctaag aaggctgctg tactggttga    5520
attgtgtccc cctcaaattc acatccttct tggaatctca gtctgtgagt ttatttggag    5580
ataaggtctc tgcagatgta gttagttaag acaaggtcat gctggatgaa ggtagaccta    5640
aattyaatat gactggttty cttgtatgaa aaggagagga cacagagaca gaggagacgc    5700
ggggaagact atgtaaagat gaaggcagag atcggagttt tgcagccaca a             5751
```

<210> SEQ ID NO 8
<211> LENGTH: 7605
<212> TYPE: DNA

<213> ORGANISM: Homo sapiens

<400> SEQUENCE: 8

| | | | | | |
|---|---|---|---|---|---|
| aatattgaca | gtatgcacag | tcatagtttc | attttactta | ttatttattt | atttattgag | 60 |
| gcagaagtct | agctctcttc | tgtcatccag | ctgggagtac | agtggctcaa | tcttggctca | 120 |
| ccgcaatctc | acctccaggt | tcaagcaatt | ctcacacctc | agcctcctga | gtagcttgga | 180 |
| ttacaaatgt | gcactacaac | ccggctaatt | tttgtgtttt | cagtaaagat | ggggttttgc | 240 |
| catgttggcc | aggcttgtct | catttcatct | tatttctact | gtcattccat | ttggtcaatt | 300 |
| tgtaatttaa | taattttgta | caaggcagtt | tctacattaa | ttttattttt | ctgaaaagtg | 360 |
| tctatcatat | tagtggcatt | atgaaaatcg | tagattattt | tctgtgtttt | gaacaacttg | 420 |
| atattttatt | tattcttgaa | cacttgtagg | acctcttggc | tcatatgtct | gaataccatt | 480 |
| tctttaaaat | gtacgcttta | acatgtatac | atatgtaaca | aacctgcaca | ttgtacacat | 540 |
| gtatcctaaa | acttaaagta | taataataat | aataaaagaa | aaagaaaaa | taaaacttaa | 600 |
| aaaaataaag | tgtatgcttt | aacaataaat | tattaataaa | tagttatctg | tgttattcaa | 660 |
| gatataatta | aattgttttt | tgtgcactga | cccttacctt | tatttcagat | ccatcacaga | 720 |
| gagtgcatgg | aggtatttaa | actgcattac | tgtttcacaa | ttaagtatta | tctttatcaa | 780 |
| ttaggattca | agaaagatca | cttacagaat | tatagatggc | atgagctaga | ttttactttc | 840 |
| taaagaaata | accagataca | tgagcaaaga | tgttaataca | aagatgtttg | tcacaacatg | 900 |
| gttttcaata | gcaaaaaaag | agagaaaaat | atataaaaga | caaataacag | tggataggtt | 960 |
| tcaataaata | atgttacagt | gatacagtta | aatactatac | agctattgaa | gcatgtcatt | 1020 |
| attcatattt | agtatggaaa | gatattttgc | tattttgcta | catgaaaaaa | tgaggttgga | 1080 |
| aaaagtatag | gttttgtgaa | tctgttgtat | gaaagctgtc | ttatagttac | atgtgtatgt | 1140 |
| gtgtggagga | aaaagtgttg | tcattggttt | tctgatgatg | cactcagaaa | agacaagtat | 1200 |
| tcacattttt | tcttgtggct | gatctggatt | ttcaggtttt | tctacaatga | acatgtaggc | 1260 |
| tgaacattcc | ctaagcagga | gagtcccacc | tctaacatct | cctgtaggcc | tggcaatggc | 1320 |
| aggcaggaaa | gacagaggaa | ggaaggaggg | agaagggaag | gagtgaagga | aggagtgaaa | 1380 |
| aaggtaagga | agaaagggaa | tagggaggga | agggaggaaa | tgggaaggga | aagaaggaaa | 1440 |
| kgaagggaaa | gagggagggg | aagaaaggaa | ggggaaaagg | gagggagtga | gttgaatgaa | 1500 |
| agatggaaag | aaggaagaaa | gggagggagg | cagggaggaa | agaaagttgc | gcttcccttg | 1560 |
| agctgcccat | gggcacctga | ctcttagggt | ctgaaaggcc | cctgagatgc | aaaagcctag | 1620 |
| tgctcacaaa | gagctggaaa | gcctcaagga | agttcttcaa | tatttctgga | aggaaactgt | 1680 |
| ctccagaagc | ttccctcccc | acgacagata | tgagcagca | agtgcttctg | gcgacttagg | 1740 |
| gtgatgtgaa | attcacgctg | ggaatcctgc | tcctcctcag | gtcctggcaa | gtttcagggc | 1800 |
| ccctccctag | gccttactta | aaaggctgag | gcatccttgg | aggaacaggc | agactccaca | 1860 |
| gctcccgcca | ggagaaagga | acattctgag | gtatgctctg | gggcgctggt | ggtaccggag | 1920 |
| ctctctcctg | accccagacc | cagaatctgc | tccgtggagg | ctgttcacat | gctggggagc | 1980 |
| tcggtgcagc | tgcttgctcc | ccagacccca | gccaactcag | cctctctctc | catgattttc | 2040 |
| tgttgtttat | tccaaaatag | gggagtctac | accctgtgga | gctcaagatg | gtcctgagtg | 2100 |
| gggcgctgtg | cttccggtga | gtgtatgagg | ccctggtttg | gtggtgtcct | ccggaggaag | 2160 |
| tgagttctgg | atagacccgt | tgtccagctc | tgagcaggag | ggaggaaggg | aggggctgc | 2220 |
| cattgcagct | gggaaattgt | gaccagcacc | tcattgctct | tagagttttc | ccagccttt | 2280 |

```
tcaaataggg gcaggactgg ggcaggccat ctcacaaggg gtccctgatg ctgaggggga    2340
caagtgaacc tcccagtcta gagctccagc caagtctatc caaggtggga acggggccca    2400
ggatccctgc tcagagctcc gccattgtcc cccatcacag tgaatggatg taagctcacc    2460
cactctgtgc ccctacctcc ctgctactct ttgggggata ataataaaac aaaaaccatt    2520
accatcagcc aagtctgtcc acccactggc atgtaccaag ccagacactc tgccgtgttc    2580
tgggcttaac aaccagagga tgagagtggt cctttctctc agtctaataa agcacttccc    2640
acgatgtgtt ctatgggact cgattagagg agtcccacag aggcatccag gagatgcttt    2700
acacagtgga gctctctgat caagtaaatg cagggaattc tgctttctac atcctctcat    2760
aagagaacca cagcccagct cagcatatga gtgactgagg ktttctgaag taaggcaact    2820
tgttgaatcg yatttagcta tgcatcgacc caattttttac actgcatcct tttcccccat    2880
ataacttttg gagaaaccca ctttaggata catcttccac ctcataggat gccaggaaat    2940
caactgagtt caaagatgag aaacaacttt gaaaagttaa ataaaagaaa tttaaattta    3000
aagaaactcc tcacttagta aggaatatat gaccaaaatag aaatacatgt atcttgaaga    3060
attgaagaat caggctttaa cgtggaagag gcctggatgt tatccaaccc atcatcttag    3120
tgtagcaatg gggaggctca gacccaagag tgggcgagag agttgtctcc tgcgactcag    3180
cagcattgga ggcatagatg gggcaagatc ctagggctct gactcaccga gcagcttctc    3240
ttccaacagg agatggggttg gggcagaaaa ggttgaatag ggtgaaggag caaaccacag    3300
actccagtgg gagactgtgg ggtcatcctc cttgtagggc atgagcccag cagggctggg    3360
agacaaggct gtgctgttac ttctggcaca gtaggaagaa agagagacaa aatgcctgag    3420 atcaggggggt tctctggatc cagggcatgc tggagtgtcc accctcctcc taatgtagtc    3480
ctcacccctt cctgatgttt cagaatgaag gactcggcat tgaaggtgct ttatctgcat    3540
aataaccagc ttctagctgg agggctgcat gcagggaagg tcattaaagg ttggtgatga    3600
aacatgaccc actttccttg gtctctatac actctcaggg gagggggcct gaagagggct    3660
tagaatagtc atacagatta gcataggcct acagagccca ggcattaggg cagcacaaac    3720
caggctctaa gcaaaggcaa ataaaatact acacctctca gcaaagtgaa gacacacgct    3780
ctggggccac ctgaagcttc tgtgcagaag tgagaatgtt ttccaagagg cttgtcttgt    3840 cattcccttta caggtagatw taggtcaagc attgcattcc ctgggagcca gtaagtacca    3900
aggagagaac taacgtagat tctctatacc tttttttccca tatgggagtg ggtttctgcc    3960
tctccaccct gggtcccctc tgctctctga agatcctcag tcacttagag tggagggacc    4020
cagagaacag gtggcattgt tggacctcct gcttgctcac tctgccccat gcactgcaac    4080
aggtccctct ctaaaatagt tygcacctgc ccacctgggg caccccttgct gagcacagat    4140 gccaggtaga tccttcagct aggccatatg tgtatgtgtg tgcttactgg tgtatgtatg    4200
tgtgcatgca ggcatatatg tgtgagcata tgtgtgcatg catgtatctg tatgtaacca    4260
tgtatgtgtg agtgcaggta tgtaggtatg agcatgtgtg tgaatatgta tatgtgtgca    4320
tgcatgtatc tgtgcatgta tgatctgatg tatgtgggtg gtgagggggat gtacagagag    4380 gaatgagacc ctcttttgct ctcagcaacc tcacaggggta tagaaagttg tccaaacaat    4440
tccaaagggg ggcttattaa gacagggttc agaaaaaggc ctgagaccca aggggcatta    4500
aaggaggggg ttgagtctat tttgggttgt agaggcttga agatttgacc ctgaactaga    4560
gggtggagtg gaggtggtac aatgtgcttc catgccttga tgtccactct gggccagtgg    4620
```

-continued

```
acaggagaag ccatgtcatg acagctgctg agaagcctcc cttctgccca gcctgggggc    4680
aggccgtctc acagcagtcc tgtgccctag agcccaggac aggggaagaa ggagggaaag    4740
gcatccaggg ccctgcatct ggcctctttc ccacaggtga agagatcagc gtggtcccca    4800
atcggtggct ggatgccagc ctgtcccccg tcatcctggg tgtccagggt ggaagccagt    4860
gcctgtcatg tggggtgggg caggagccga ctcttaacac tagaggtgag acttggggca    4920
tcctcactgg ggactcagcc acagatgctg agcctactga agccgggcag cccacagccc    4980
tggtgctgtg ggacacccta gcaggattct gttgatggca gctttgcctc ctccctaagg    5040
atcctgccca gccctccctc tgcccctgct tctgccctca cctgacctcc cctcctctgc    5100
cggcagccag tgaacatcat ggagctctat cttggtgcca aggaatccaa gagcttcacc    5160
ttctaccggc gggacatggg gctcacctcc agcttcgagt cggctgccta cccgggctgg    5220
ttcctgtgca cggtgcctga agccgatcag cctgtcagac tcacccagct tcccgagaat    5280
ggtggctgga atgcccccat cacagacttc tacttccagc agtgtgacta gggcaacgtg    5340
ccccccagaa ctccctgggc agagccagct cgggtgaggg gtgagtggag gagacccatg    5400
gcggacaatc actctctctg ctctcaggac ccccacgtct gacttagtgg gcacctgacc    5460
actttgtctt ctggttccca gtttggataa attctgagat ttggagctca gtccacggtc    5520
ctcccccact ggatggtgct actgctgtgg aaccttgtaa aaaccatgtg gggtaaactg    5580
ggaataacat gaaagatttt ctgtgggggt ggggtggggg agtggtggga atcattcctg    5640
cttaatggta actgacaagt gttaccctga gccccgcagg ccaacccatc cccagttgag    5700
ccttataggg tcagtagctc tccacatgaa gtcctgtcac tcaccactgt gcaggagagg    5760
gaggtggtca tagagtcagg gatctatggc ccttggccca gccccacccc cttccctta    5820 atcctgccac tgtcatatgc tacctttcct atctcttccc tcatcatctt gttgtgggca    5880
tgaggaggtg gtgatgtcag aagaaatggc tcgagctcag aagataaaag ataagtaggg    5940
tatgctgatc ctcttttaaa aacccaagat acaatcaaaa tcccagatgc tggtctctat    6000
tcccatgaaa aagtgctcat gacatattga gaagacctac ttacaaagtg gcatatattg    6060
caatttattt taattaaaag atacctattt atatatttct ttatagaaaa aagtctggaa    6120
gagtttactt caattgtagc aatgtcaggg tggtggcagt ataggtgatt tttcttttaa    6180
ttctgttaat ttatctgtat ttcctaattt ttctacaatg aagatgaatt ccttgtataa    6240
aaataagaaa agaaattaat cttgaggtaa gcagagcaga catcatctct gattgcctca    6300
gcctccactt ccccagagta aattcaaatt gaatcgagct ctgctgctct ggttggttgt    6360
agtagtgatc aggaatcaga tctcagcaaa gccactgagg aggaggctgt gatgagtttg    6420
tgtggctgga atctctgggt aaggaactta agaacaaaa atcatctggt aattctttcc    6480
tagaaggatc acagccctg ggattccaag gcattggatc cagtctctaa gaaggctgct    6540
gtactggttg aattgtgtcc ccctcaaatt cacatccttc ttggaatctc agtctgtgag    6600
tttatttgga gataaggtct ctgcagatgt agttagttaa gacaaggtca tgctggatga    6660
aggtagacct aaattcaata tgactggttt ccttgtatga aaaggagagg acacagagac    6720
agaggagacg cggggaagac tatgtaaaga tgaaggcaga gatcggagtt ttgcagccac    6780
aagctaagaa acaccaagga ttgtggcaac catcagaagc ttggaagagg caaagaagaa    6840
ttcttcccta gaggctttag agggataacg gctctgctga caccttaatc tcagacttcc    6900
agcctcctga acgaagaaag aataaatttc ggctgttta agccaccaag gataattggt    6960
tatggcagct ctaggaaact aatacagctg ctaaaatgat ccctgtctcc tcgtgtttac    7020
```

```
attctgtgtg tgtcccctcc cacaatgtac caaagttgtc tttgtgacca atagaatatg    7080
gcagaagtga tggcatgcca cttccaagat taggttataa aagacactgc agcttctact    7140
tgagccctct ctctctgcca cccaccgccc ccaatctatc ttggctcact cgctctgggg    7200
gaagctagct tccatgctat gagcaggcct ataaagagac ttatgtggta aaaaatgaag    7260
tctcctgccc acagccacat tagtgaacct agaagcagag actctgtgag ataatcaatg    7320
tttgttgttt taagttgctc agttttggtc taacttgtta tgcagcaata gataaataat    7380
atgcagagaa agagaaacaa atgcatttgt tttattattg caattttctc caatattttt    7440
tattttcttt ctcacaatga acaactatcc ttcatttacc caaatattct atttaaaagc    7500
taataataca gcatttgttg agtcatctgg ttctgcaaga ttgagatcct cttgtcctat    7560
gtgccaggaa tgaactccag tgccccaccc aaaccctggg gaatg                   7605
```

<210> SEQ ID NO 9
<211> LENGTH: 178
<212> TYPE: PRT
<213> ORGANISM: Mus musculus

<400> SEQUENCE: 9

```
Met Glu Ile Cys Trp Gly Pro Tyr Ser His Leu Ile Ser Leu Leu Leu
 1               5                  10                  15

Ile Leu Leu Phe His Ser Glu Ala Ala Cys Arg Pro Ser Gly Lys Arg
            20                  25                  30

Pro Cys Lys Met Gln Ala Phe Arg Ile Trp Asp Thr Asn Gln Lys Thr
        35                  40                  45

Phe Tyr Leu Arg Asn Asn Gln Leu Ile Ala Gly Tyr Leu Gln Gly Pro
    50                  55                  60

Asn Ile Lys Leu Glu Glu Lys Ile Asp Met Val Pro Ile Asp Leu His
65                  70                  75                  80

Ser Val Phe Leu Gly Ile His Gly Gly Lys Leu Cys Leu Ser Cys Ala
                85                  90                  95

Lys Ser Gly Asp Asp Ile Lys Leu Gln Leu Glu Glu Val Asn Ile Thr
            100                 105                 110

Asp Leu Ser Lys Asn Lys Glu Glu Asp Lys Arg Phe Thr Phe Ile Arg
        115                 120                 125

Ser Glu Lys Gly Pro Thr Thr Ser Phe Glu Ser Ala Ala Cys Pro Gly
    130                 135                 140

Trp Phe Leu Cys Thr Thr Leu Glu Ala Asp Arg Pro Val Ser Leu Thr
145                 150                 155                 160

Asn Thr Pro Glu Glu Pro Leu Ile Val Thr Lys Phe Tyr Phe Gln Glu
                165                 170                 175

Asp Gln
```

<210> SEQ ID NO 10
<211> LENGTH: 178
<212> TYPE: PRT
<213> ORGANISM: Rattus norvegicus

<400> SEQUENCE: 10

```
Met Glu Ile Cys Arg Gly Pro Tyr Ser His Leu Ile Ser Leu Leu Leu
 1               5                  10                  15

Ile Leu Leu Phe Arg Ser Glu Ser Ala Gly His Pro Ala Gly Lys Arg
            20                  25                  30

Pro Cys Lys Met Gln Ala Phe Arg Ile Trp Asp Thr Asn Gln Lys Thr
```

```
                35                  40                  45
Phe Tyr Leu Arg Asn Asn Gln Leu Ile Ala Gly Tyr Leu Gln Gly Pro
 50                  55                  60

Asn Thr Lys Leu Glu Glu Lys Ile Asp Met Val Pro Ile Asp Phe Arg
 65                  70                  75                  80

Asn Val Phe Leu Gly Ile His Gly Gly Lys Leu Cys Leu Ser Cys Val
                 85                  90                  95

Lys Ser Gly Asp Asp Thr Lys Leu Gln Leu Glu Glu Val Asn Ile Thr
                100                 105                 110

Asp Leu Asn Lys Asn Lys Glu Glu Asp Lys Arg Phe Thr Phe Ile Arg
            115                 120                 125

Ser Glu Thr Gly Pro Thr Thr Ser Phe Glu Ser Leu Ala Cys Pro Gly
130                 135                 140

Trp Phe Leu Cys Thr Thr Leu Glu Ala Asp His Pro Val Ser Leu Thr
145                 150                 155                 160

Asn Thr Pro Lys Glu Pro Cys Thr Val Thr Lys Phe Tyr Phe Gln Glu
                165                 170                 175

Asp Gln

<210> SEQ ID NO 11
<211> LENGTH: 177
<212> TYPE: PRT
<213> ORGANISM: Oryctolagus cuniculus

<400> SEQUENCE: 11

Met Arg Pro Ser Arg Ser Thr Arg Arg His Leu Ile Ser Leu Leu Leu
 1               5                  10                  15

Phe Leu Phe His Ser Glu Thr Ala Cys Arg Pro Ser Gly Lys Arg Pro
                 20                  25                  30

Cys Arg Met Gln Ala Phe Arg Ile Trp Asp Val Asn Gln Lys Thr Phe
             35                  40                  45

Tyr Leu Arg Asn Asn Gln Leu Val Ala Gly Tyr Leu Gln Gly Pro Asn
 50                  55                  60

Ala Lys Leu Glu Glu Arg Ile Asp Val Val Pro Leu Glu Pro Gln Leu
 65                  70                  75                  80

Leu Phe Leu Gly Ile Gln Arg Gly Lys Leu Cys Leu Ser Cys Val Lys
                 85                  90                  95

Ser Gly Asp Lys Met Lys Leu His Leu Glu Ala Val Asn Ile Thr Asp
                100                 105                 110

Leu Gly Lys Asn Lys Glu Gln Asp Lys Arg Phe Thr Phe Ile Arg Ser
            115                 120                 125

Asn Ser Gly Pro Thr Thr Thr Phe Glu Ser Ala Ser Cys Pro Gly Trp
130                 135                 140

Phe Leu Cys Thr Ala Leu Glu Ala Asp Gln Pro Val Ser Leu Thr Asn
145                 150                 155                 160

Thr Pro Asp Asp Ser Ile Val Val Thr Lys Phe Tyr Phe Gln Glu Asp
                165                 170                 175

Gln

<210> SEQ ID NO 12
<211> LENGTH: 18
<212> TYPE: PRT
<213> ORGANISM: Homo sapiens

<400> SEQUENCE: 12
```

Asn Tyr Pro Lys Lys Lys Met Glu Lys Arg Phe Val Phe Asn Lys Ile
1               5                   10                  15

Glu Ile

<210> SEQ ID NO 13
<211> LENGTH: 18
<212> TYPE: PRT
<213> ORGANISM: Homo sapiens

<400> SEQUENCE: 13

Leu Ser Glu Asn Arg Lys Gln Asp Lys Arg Phe Ala Phe Ile Arg Ser
1               5                   10                  15

Asp Ser

<210> SEQ ID NO 14
<211> LENGTH: 159
<212> TYPE: PRT
<213> ORGANISM: Homo sapiens

<400> SEQUENCE: 14

Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
                20                  25                  30

Arg Asn Asn Gln Leu Val Ala Gly Tyr Leu Gln Gly Pro Asn Val Asn
            35                  40                  45

Leu Glu Glu Lys Ile Asp Val Val Pro Ile Glu Pro His Ala Leu Phe
        50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
                85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
        115                 120                 125

Cys Thr Ala Met Glu Ala Asp Gln Pro Val Ser Leu Thr Asn Met Pro
    130                 135                 140

Asp Glu Gly Val Met Val Thr Lys Phe Tyr Phe Gln Glu Asp Glu
145                 150                 155

<210> SEQ ID NO 15
<211> LENGTH: 21
<212> TYPE: DNA
<213> ORGANISM: Gene-specific 5' primer

<400> SEQUENCE: 15
ccccactgga tggtgctact g                                            21

<210> SEQ ID NO 16
<211> LENGTH: 21
<212> TYPE: DNA
<213> ORGANISM: Gene-specific 3' primer

<400> SEQUENCE: 16
gggaagagat aggaaaggta g                                            21

<210> SEQ ID NO 17
<211> LENGTH: 12

<212> TYPE: DNA
<213> ORGANISM: Intron

<400> SEQUENCE: 17
tctgaggtat gc                                                              12

<210> SEQ ID NO 18
<211> LENGTH: 12
<212> TYPE: DNA
<213> ORGANISM: Exon

<400> SEQUENCE: 18
aaatagggga gt                                                              12

<210> SEQ ID NO 19
<211> LENGTH: 12
<212> TYPE: DNA
<213> ORGANISM: Intron

<400> SEQUENCE: 19
cttccggtga gt                                                              12

<210> SEQ ID NO 20
<211> LENGTH: 12
<212> TYPE: DNA
<213> ORGANISM: Exon

<400> SEQUENCE: 20
tttcagaatg aa                                                              12

<210> SEQ ID NO 21
<211> LENGTH: 12
<212> TYPE: DNA
<213> ORGANISM: Intron

<400> SEQUENCE: 21
ttaaaggttg gt                                                              12

<210> SEQ ID NO 22
<211> LENGTH: 12
<212> TYPE: DNA
<213> ORGANISM: Exon

<400> SEQUENCE: 22
ccacaggtga ag                                                              12

<210> SEQ ID NO 23
<211> LENGTH: 12
<212> TYPE: DNA
<213> ORGANISM: Intron

<400> SEQUENCE: 23
ctagaggtga ga                                                              12

<210> SEQ ID NO 24
<211> LENGTH: 12
<212> TYPE: DNA
<213> ORGANISM: Exon

<400> SEQUENCE: 24
cggcagccag tg                                                              12

<210> SEQ ID NO 25

```
<211> LENGTH: 29
<212> TYPE: DNA
<213> ORGANISM: Artificial Sequence
<220> FEATURE:
<223> OTHER INFORMATION: TBD

<400> SEQUENCE: 25
gaagatctat ggtcctgagt ggggccctg                              29

<210> SEQ ID NO 26
<211> LENGTH: 29
<212> TYPE: DNA
<213> ORGANISM: Artificial Sequence
<220> FEATURE:
<223> OTHER INFORMATION: TBD

<400> SEQUENCE: 26
gaagatctgt cacactgctg gaagtagaa                              29

<210> SEQ ID NO 27
<211> LENGTH: 12
<212> TYPE: DNA
<213> ORGANISM: Artificial Sequence
<220> FEATURE:
<223> OTHER INFORMATION: TBD

<400> SEQUENCE: 27
ctgtaggcct gg                                                12

<210> SEQ ID NO 28
<211> LENGTH: 12
<212> TYPE: DNA
<213> ORGANISM: Artificial Sequence
<220> FEATURE:
<223> OTHER INFORMATION: TBD

<400> SEQUENCE: 28
aaaaaggtaa gg                                                12

<210> SEQ ID NO 29
<211> LENGTH: 12
<212> TYPE: DNA
<213> ORGANISM: Artificial Sequence
<220> FEATURE:
<223> OTHER INFORMATION: TBD

<400> SEQUENCE: 29
cctcaggtcc tg                                                12

<210> SEQ ID NO 30
<211> LENGTH: 177
<212> TYPE: PRT
<213> ORGANISM: Homo sapiens

<400> SEQUENCE: 30
```

Met Glu Ile Cys Arg Gly Leu Arg Ser His Leu Ile Thr Leu Leu Leu
 1               5                  10                  15

Phe Leu Phe His Ser Glu Thr Ile Cys Arg Pro Ser Gly Arg Lys Ser
                20                  25                  30

Ser Lys Met Gln Ala Phe Arg Ile Trp Asp Val Asn Gln Lys Thr Phe
            35                  40                  45

Tyr Leu Arg Asn Asn Gln Leu Val Ala Gly Tyr Leu Gln Gly Pro Asn
        50                  55                  60

Val Asn Leu Glu Glu Lys Ile Asp Val Val Pro Ile Glu Pro His Ala

```
                         -continued
65                  70                  75                  80
Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```

ANTI-INTERLEUKIN-1 RECEPTOR ANTAGONIST ANTIBODIES AND USES THEREOF

RELATED APPLICATIONS

This patent application is a continuation-in-part of U.S. patent application Ser. No. 09/348,942 filed Jul. 7, 1999 which is a continuation-in-part of U.S. patent application Ser. No. 09/287,210 filed Apr. 5, 1999 which is a continuation-in-part of U.S. patent application Ser. No. 09/251,370 filed Feb. 17, 1999 now abandoned which is a continuation-in-part of U.S. patent application Ser. No. 09/127,698 filed Jul. 31, 1998 now abandoned, and a continuation-in-part of U.S. patent application Ser. No. 09/229,591 filed Jan. 13, 1999, now abandoned which is a continuation of U.S. patent application Ser. No. 09/099,818 filed Jun. 19, 1998 now abandoned. U.S. patent application Ser. Nos. 09/127,698 and 09/099,818 are continuations in part of U.S. patent application Ser. No. 09/082,364 filed May 20, 1998 now abandoned, which is a continuation-in-part of U.S. patent application Ser. No. 09/079,909 filed May 15, 1998 now abandoned, which is a continuation-in-part of U.S. patent application Ser. No. 09/055,010 filed Apr. 3, 1998 now abandoned, all of which are incorporated by reference herein in their entirety.

FIELD OF THE INVENTION

The present invention provides novel polynucleotides and proteins encoded by such polynucleotides, along with therapeutic, diagnostic and research utilities for these polynucleotides and proteins.

BACKGROUND

Technology aimed at the discovery of protein factors (including e.g., cytokines, such as lymphokines, interferons, CSFs, chemokines, and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). More recent "indirect" cloning techniques such as signal sequence cloning, which isolates DNA sequences based on the presence of a now well-recognized secretory leader sequence motif, as well as various PCR-based or low stringency hybridization cloning techniques, have advanced the state of the art by making available large numbers of DNA/amino acid sequences for proteins that are known to have biological activity by virtue of their secreted nature in the case of leader sequence cloning, or by virtue of the cell or tissue source in the case of PCR-based techniques. It is to these proteins and the polynucleotides encoding them that the present invention is directed. In particular, this invention is directed to a novel Interleukin-1 Receptor Antagonist.

Cytokines, such as Interleukin-1, are well known to cause morphological and functional alterations in endothelial cells. These alterations occur in part as a result of "endothelial cell activation" Distinct immune-mediators such as tumor necrosis factor (TNF), interleukin-1 (Interleukin-1), and gamma-interferon (IFN) appear to induce different but partially overlapping patterns of endothelial cell activation including increased procoagulant activity (Bevilaqua (1986) PNAS, 83:4533–4537), PGI and 2 production (Rossi (1985), Science, 229:174–176), HLA antigen expression (Pober (1987) J. Immunol., 138:3319–3324) and lymphocyte adhesion molecules (Carender (1987) J. Immunol., 138:2149–2154). These cytokines are also reported to cause hypotension, vascular hemorrhage, and ischemia (Goldblum et al. 1989, Tracey et al. Science 234:470, 1986). A major dose limiting toxicity of these and other biological response modifiers is hypotension and vascular leakage (Dvorak (1989) J.N.C.I., 81:497–502).

The ability of IL-1 to modify biological responses has been demonstrated in a variety of studies. For example, the administration of Interleukin-1 to rabbits (Wakabayashi et al., FASEB J 1991;5:338; Okusawa et al. J Clin Invest 1988;81:1162; Ohlsson et al., Nature 1990;348:550; Aiura, et al. Cytokine 1991;4:498) and primates (Fischer et al. Am J Physiol 1991;261:R442) has been shown to result in hypotension, tachycardia, lung edema, renal failure, and, eventually, death, depending on the dose. When the serum from the Interleukin-1 treated animals is examined, the elevation of other cytokines is evident, mimicking the levels seen in acute pancreatitis in humans. (Guice et al., J Surg Res 1991;51:495–499; Heath et al., Pancreas 1993;66:41–45) There is a large body of evidence currently available which supports the role of Interleukin-1 as a major mediator of the systemic response to diseases such as sepsis and pancreatitis and as an activator of the remaining members of the cytokine cascade. (Dinarello et al., Arch Surg 1992;127:1350–1353).

The cytokine Interleukin-1 is a key mediator in the inflammatory response (for reviews, see Dinarello (1991) Blood 77: 1627–1652; Dinarello et al. (1993) New England J. Med. 328:106–113; Dinarello (1994) FASEB J. 8:1314–1325). The importance of Interleukin-1 in inflammation has been demonstrated by the ability of the highly specific Interleukin-1 receptor antagonist protein to relieve inflammatory conditions (for review, see Dinarello (1991) Blood 77: 1627–1652; Dinarello et al. (1993) New England J. Med. 328:106–113; Dinarello (1994) FASEB J. 8:1314–1325; Dinarello (1993) Immunol. Today 14:260–264). Many of the proinflammatory effects of Interleukin-1, such as the upregulation of cell adhesion molecules on vascular endothelia, are exerted at the level of transcriptional regulation. The transcriptional activation by Interleukin-1 of cell adhesion molecules and other genes involved in the inflammatory response appears to be mediated largely by NF-kappa B (Shirakawa et al. (1989) Molc. Cell Biol. 9:2424–2430; Osborn et al., (1989) Proc. Natl. Acad. Sci. USA 86:2336–2340; Krasnow et al., (1991) Cytokine 3:372–379; Collins et al., (1993) Trends Cardiovasc. Med. 3:92–97). In response to Interleukin-1, the NF-kappa B inhibitory factor I kappa B is degraded and NF-kappa B is released from its inactive cytoplasmic state to localize within the nucleus where it binds DNA and activates transcription (Liou et al. (1993) Curr. Opin. Cell Biol. 5:477–487; Beg et al., (1993) Mol. Cell. Bid. 13:3301–3310).

Interleukin-1 is also a mediator of septic shock . Septic shock, a life-threatening complication of bacterial infections, affects 150,000 to 300,000 patients annually in the United States (Parrillo, J. E. (1989), Septic Shock in Humans: Clinical Evaluation, Pathogenesis, and Therapeutic Approach (2nd ed.) In: Textbook of Critical Care Shoemaker, et al., editors, Saunders Publishing Co., Philadelphia, Pa., pp. 1006). The cardiovascular collapse and multiple metabolic derangements associated with septic shock are due largely to bacterial endotoxin (ET), which has been shown to elicit a septic shock-like condition when administered to animals (Natanson, et al. (1989), Endotoxin and Tumor Necrosis Factor Challenges in Dogs Simulate the Cardiovascular Profile of Human Septic Shock, J. Exp. Med. 169:823). Thus, there is a great need for modulators of Interleukin-1.

SUMMARY OF THE INVENTION

The compositions of the present invention include novel isolated polypeptides, in particular, novel Interleukin-1 Receptor Antagonist proteins (referred to hereafter as IL-1Hy1), isolated polynucleotides encoding such polypeptides, including recombinant DNA molecules, cloned genes or degenerate variants thereof, especially naturally occurring variants such as allelic variants, and antibodies that specifically recognize one or more epitopes present on such polypeptides.

The compositions of the present invention additionally include vectors, including expression vectors, containing the polynucleotides of the invention, cells genetically engineered to contain such polynucleotides and cells genetically engineered to express such polynucleotides.

The isolated polynucleotides of the invention include, but are not limited to, a polynucleotide encoding a polypeptide comprising the amino acid sequence of SEQ ID NO: 3 or 5.

The isolated polynucleotides of the invention further include, but are not limited to, a polynucleotide comprising the nucleotide sequence of SEQ ID NO: 1, 2, 4, or 6; a polynucleotide comprising the full length protein coding sequence of SEQ ID NO: 1, 2, 4, or 6, and; a polynucleotide comprising the nucleotide sequence of the mature protein coding sequence of SEQ ID NO: 1, 2, 4, or 6. The polynucleotides of the present invention also include, but are not limited to, a polynucleotide that hybridizes to the complement of the nucleotide sequence of SEQ ID NO: 1, 2, 4, or 6 under stringent hybridization conditions; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ ID NO: 1, 2, 4, or 6.

The isolated polynucleotides of the invention further include, but are not limited to a polynucleotide comprising the nucleotide sequence of the genomic clone SEQ ID NO: 7 or 8; a polynucleotide assembled from one or more of the exons of SEQ ID NO: 7 or 8; a polynucleotide assembled from one or more of the introns of SEQ ID NO: 7 or 8; a polynucleotide assembled from one or more of the exons of SEQ ID NO: 7 or 8 and one or more of the introns of SEQ ID NO: 7 or 8; a polynucleotide comprising the full length protein coding sequence of SEQ ID NO: 7 or 8; a polynucleotide comprising the nucleotide sequence of the mature protein coding sequence of SEQ ID NO: 7 or 8; or a polynucleotide.

The polynucleotides of the present invention also include, but are not limited to, a polynucleotide that hybridizes to the complement of the nucleotide sequence of SEQ ID NO: 7 or 8 under stringent hybridization conditions; a polynucleotide that hybridizes to the complement of any one of the introns or exons of SEQ ID NO: 7 or 8 under stringent hybridization conditions; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ ID NO: 7 or 8.

The polynucleotides of the present invention still further include, but are not limited to, a polynucleotide comprising the nucleotide sequence of the cDNA insert of clone pIL-1Hy deposited with the American Type Culture Collection (ATCC; 10801 University Blvd., Manassas, Va., 20110-2209, U.S.A.); a polynucleotide comprising a nucleotide sequence encoding the amino acid sequence of SEQ ID NO: 3 or 5 which polynucleotide is assembled from the cDNA insert of clone pIL-1Hy273; a polynucleotide comprising the full length protein coding sequence of SEQ ID NO: 3 or 5 which polynucleotide is assembled from the cDNA insert of clone pIL-1Hy273; or, a polynucleotide comprising the nucleotide sequence of the mature protein coding sequence of SEQ ID NO: 3 or 5.

The polynucleotides of the invention additionally include the complement of any of the polynucleotides recited above.

The isolated polypeptides of the invention include, but are not limited to, a polypeptide comprising the amino acid sequence of SEQ ID NO: 3 or 5, a full length protein of SEQ ID NO: 3 or 5; a mature protein coding sequence of SEQ ID NO: 3 or 5.; or, a polypetide encoded by one or more of the exons of SEQ ID NO: 7 or 8.

The polypeptides of the present invention further include, but are not limited to, a polypeptide comprising the amino acid sequence encoded by the cDNA insert of clone pIL-1Hy273 deposited with the American Type Culture Collection (ATCC; 10801 University Blvd., Manassas, Va., 20110-2209, U.S.A.); a full length protein of SEQ ID NO: 3 or 5 assembled from the amino acid sequence encoded by the cDNA insert of clone pIL-1Hy273; or, a mature protein coding sequence of SEQ ID NO: 3 or 5 assembled from the amino acid sequence encoded by cDNA insert of clone pIL-1Hy273.

Protein compositions of the present invention may further comprise an acceptable carrier, such as a hydrophilic, e.g., pharmaceutically acceptable, carrier.

The invention also relates to methods for producing a polypeptide comprising growing a culture of the cells of the invention in a suitable culture medium, and purifying the protein from the culture. Preferred embodiments include those in which the protein produced by such process is a mature form of the protein.

Polynucleotides according to the invention have numerous applications in a variety of techniques known to those skilled in the art of molecular biology. These techniques include use as hybridization probes, use as oligomers for PCR, use for chromosome and gene mapping, use in the recombinant production of protein, and use in generation of anti-sense DNA or RNA, their chemical analogs and the like. For example, when the expression of an mRNA is largely restricted to a particular cell or tissue type, polynucleotides of the invention can be used as hybridization probes to detect the presence of the particular cell or tissue mRNA in a sample using, e.g., in situ hybridization.

In other exemplary embodiments, the polynucleotides are used in diagnostics as expressed sequence tags for identifying expressed genes or, as well known in the art and exemplified by Vollrath et al., Science 258:52–59 (1992), as expressed sequence tags for physical mapping of the human genome.

The polypeptides according to the invention can be used in a variety of conventional procedures and methods that are currently applied to other proteins. For example, a polypeptide of the invention can be used to generate an antibody that specifically binds the polypeptide. The polypeptides of the invention can also be used as molecular weight markers, and as a food supplement.

Methods are also provided for preventing, treating or ameliorating a medical condition which comprises administering to a mammalian subject a therapeutically effective amount of a composition comprising a protein of the present invention and a pharmaceutically acceptable carrier.

In particular, the polypeptides and polynucleotides of the invention can be utilized, for example, as part of methods for the prevention and/or treatment of disorders involving sepsis, acute pancreatitis, endotoxic shock, cytokine induced shock, rheumatoid arthritis, chronic inflammatory arthritis, pancreatic cell damage from diabetes mellitus type 1, graft versus host disease, inflammatory bowel disease, inflamation associated with pulmonary disease, other autoimmune disease or inflammatory disease, an antiproliferative agent such as for acute or chronic mylegenous leukemia or in the prevention of premature labor secondary to intrauterine infections.

The methods of the present invention further relate to methods for detecting the presence of the polynucleotides or polypeptides of the invention in a sample. Such methods can, for example, be utilized as part of prognostic and diagnostic evaluation of disorders as recited above and for the identification of subjects exhibiting a predisposition to such conditions. Furthermore, the invention provides methods for evaluating the efficacy of drugs, and monitoring the progress of patients, involved in clinical trials for the treatment of disorders as recited above.

The invention also provides methods for the identification of compounds that modulate the expression of the polynucleotides and/or polypeptides of the invention. Such methods can be utilized, for example, for the identification of compounds that can ameliorate symptoms of disorders as recited above. Such methods can include, but are not limited to, assays for identifying compounds and other substances that interact with (e.g., bind to) the polypeptides of the invention.

The methods of the invention also include methods for the treatment of disorders as recited above which may involve the administration of such compounds to individuals exhibiting symptoms or tendencies related to disorders as recited above. In addition, the invention encompasses methods for treating diseases or disorders as recited above by administering compounds and other substances that modulate the overall activity of the target gene products. Compounds and other substances can effect such modulation either on the level of target gene expression or target protein activity.

BRIEF DESCRIPTION OF THE DRAWINGS

FIG. 1 shows the sequence alignment of SEQ ID NO: 3 with human (SEQ ID NO: 30), mouse (SEQ ID NO: 9), rat (SEQ ID NO: 10) and rabbit Interleukin-1 receptor antagonist (SEQ ID NO: 11). A—Alanine; R—Arginine;—Asparagine; D—Aspartic Acid; C—Cysteine; E—Glutamic Acid; Q—Glutamine; G—Glycine; H—Histidine; I—Isoleucine; L—Leucine; K—Lysine;—Methionine; F—Phenylalanine; P—Proline; S—Serine; T—Threonine; W—Tryptophan; Y—Tyrosine; V—Valine; X—any of the twenty amino acids. Gaps are presented as dashes. Amino acid numbers for all four sequences are labeled accordingly.

FIG. 2 shows the nucleic acid sequences that were obtained from the b²HFLS20W cDNA library using standard PCR, sequencing by hybridization signature analysis, and single pass gel sequencing technology. These sequences are designated as SEQ ID NOS: 1 and 2. A—adenosine; C—cytosine; G—guanosine; T—thymine; and N—any of the four bases.

FIG. 3 shows the amino acid sequences which correspond to nucleotides 1 through 240 of SEQ ID NO: 2. These sequences are designated as SEQ ID NO: 3. A—Alanine; R—Arginine; —Asparagine; D—Aspartic Acid; C—Cysteine; E—Glutamic Acid; Q—Glutamine; G—Glycine; H—Histidine; I—Isoleucine; L—Leucine; K—Lysine; —Methionine; F—Phenylalanine; P—Proline; S—Serine; T—Threonine; W—Tryptophan; Y—Tyrosine; V—Valine; X—any of the twenty amino acids.

FIG. 4 shows the sequence alignment of receptor binding regions of human Interleukin-1 beta (SEQ ID NO: 12) and human Interleukin-1 receptor antagonist (SEQ ID NO: 13)aligned with a cognate region of SEQ ID NO:3 (amino acids 13 through 30 of SEQ ID NO:3). Residues conserved among all three domains are shown in boldface.

FIG. 5 shows the nucleic acid sequence designated SEQ ID NO: 4 (nucleotides 297 through 1282 of SEQ ID NO: 4 correspond to SEQ ID NO: 2) and are described in Example 6 . The first eleven nucleic acid sequences correspond to vector sequence.

FIG. 6 shows the amino acid sequence encoded by SEQ ID NO: 4 (amino acids 76 through 155 of SEQ ID NO: 5 correspond to SEQ ID NO; 3). This amino acid sequence is designated SEQ ID NO: 5 and is described in Example 6.

FIG. 7 presents an amino acid alignment of SEQ ID NO: 5 (amino acids 1 through 155 of SEQ ID NO: 5) with the cytoplasmic form of human IL-1 Ra (SEQ ID NO: 14; labeled "HUMIL1RASIC"). The homology between these two sequences is discussed in Example 6.

FIG. 8 shows SEQ ID NO: 6 which represents an extension (the underlined sequence) of the nucleic acid sequence corresponding to SEQ ID NO: 4 and is described in Example 7.

FIGS. 9A–C show the genomic sequence corresponding to SEQ ID NOS: 1, 2, and 4 6. The isolation of the genomic clone (SEQ ID NO: 7 ) from which this sequence was derived is described in Example 8. A—adenosine; C—cytosine; G—guanosine; T—thymine. Ambiguous positions are designated as follows: R indicates A or G; M indicates A or C; W indicates A or T; Y indicates C or T; S indicates C or G; K indicates G or T; V indicates A or C or G; H indicates A or C or T; D indicates A or G or T; B indicates C or G or T; and N indicates any of the four bases.

FIGS. 10A–C show a genomic clone (SEQ ID NO: 8) which is an extension of the genomic sequence presented in FIG. 9A–C (SEQ ID NO: 7). SEQ ID NO: 8 includes the extended sequence shown in SEQ ID NO: 6 for the Interleukin-1 Receptor Antagonist extension presented in SEQ ID NO: 6. The isolation of this genomic clone (SEQ ID NO: 7 ) from which this sequence was derived is described in Example 11. A—adenosine; C—cytosine; G—guanosine; T—thymine. Ambiguous positions are designated as follows: R indicates A or G; M indicates A or C; W indicates A or T; Y indicates C or T; S indicates C or G; K indicates G or T; V indicates A or C or G; H indicates A or C or T; D indicates A or G or T; B indicates C or G or T; and N indicates any of the four bases.

DETAILED DESCRIPTION

Definitions

Figure 11:
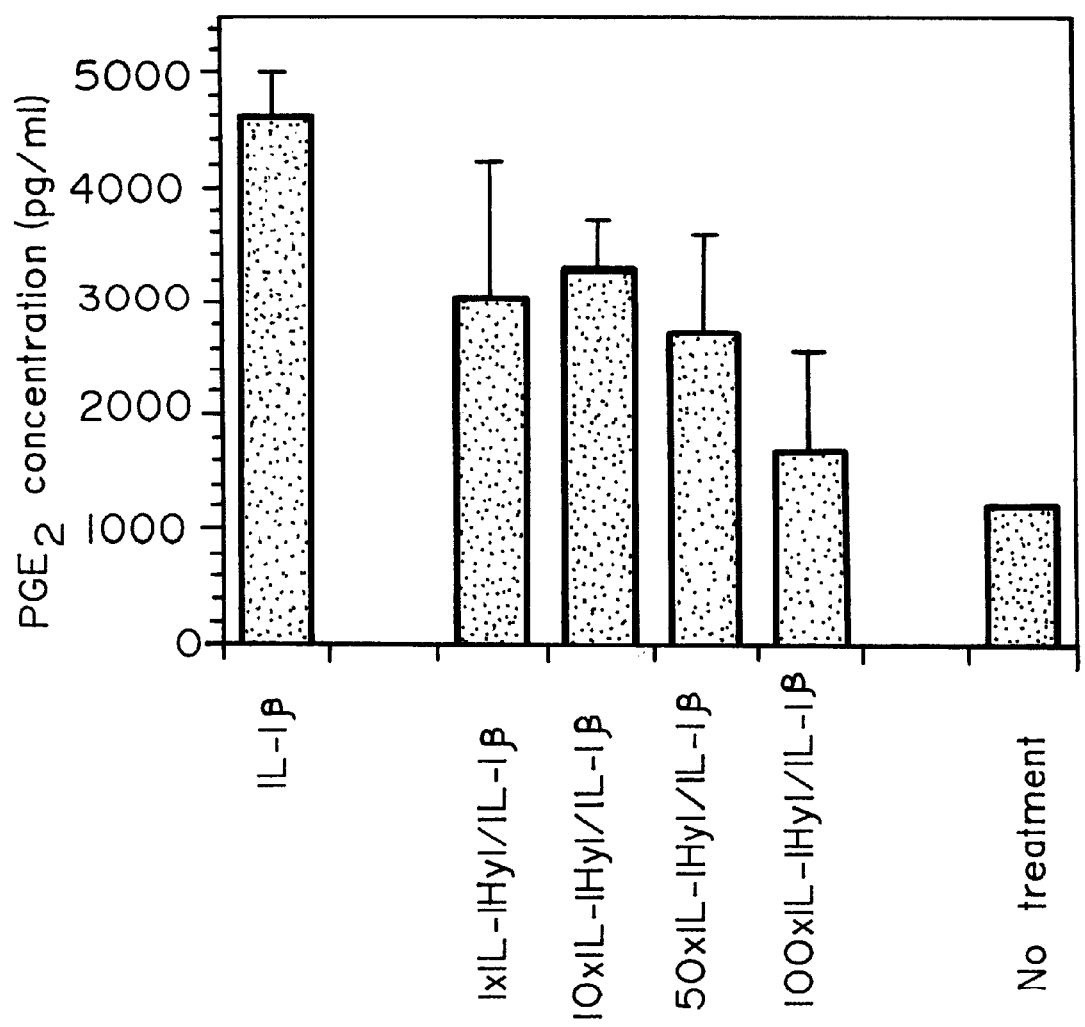
FIG. 11 shows the dose dependent ability of IL-1Hy1 to inhibit IL-1β induced PGE$_2$ production.

The term "nucleotide sequence" refers to a heteropolymer of nucleotides or the sequence of these nucleotides. The terms "nucleic acid" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment", "portion," or "segment" is a stretch of polypeptide nucleotide residues which is long enough to use in polymerase chain reaction (PCR) or various hybridization procedures to identify or amplify identical or related parts of mRNA or DNA molecules.

The terms "oligonucleotides" or "nucleic acid probes" are prepared based on the polynucleotide sequences provided in the present invention. Oligonucleotides comprise portions of such a polynucleotide sequence having at least about 15 nucleotides and usually at least about 20 nucleotides. Nucleic acid probes comprise portions of such a polynucleotide sequence having fewer nucleotides than about 6 kb, usually fewer than about 1 kb. After appropriate testing to eliminate false positives, these probes may, for example, be used to determine whether specific mRNA molecules are present in a cell or tissue or to isolate similar nucleic acid sequences from chromosomal DNA as described by Walsh et al. (Walsh, P. S. et al., 1992, PCR Methods Appl 1:241–250).

The term "probes" includes naturally occurring or recombinant or chemically synthesized single- or double-stranded nucleic acids. They may be labeled by nick translation, Klenow fill-in reaction, PCR or other methods well known in the art. Probes of the present invention, their preparation and/or labeling are elaborated in Sambrook, J. et al., 1989, Molecular Cloning: A Laboratory Manual, Cold Spring Harbor Laboratory, NY; or Ausubel, F. M. et al., 1989, Current Protocols in Molecular Biology, John Wiley & Sons, New York, N.Y., both of which are incorporated herein by reference in their entirety.

The term "stringent" is used to refer to conditions that are commonly understood in the art as stringent. Stringent conditions can include highly stringent conditions (i.e., hybridization to filter-bound DNA under in 0.5 M $NaHPO_4$, 7% sodium dodecyl sulfate (SDS), 1 mM EDTA at 65° C., and washing in 0.1×SSC/0.1% SDS at 68° C.), and moderately stringent conditions (i.e., washing in 0.2×SSC/0.1% SDS at 42° C.).

In instances wherein hybridization of deoxyoligonucleotides is concerned, additional exemplary stringent hybridization conditions include washing in 6×SSC/0.05% sodium pyrophosphate at 37° C. (for 14-base oligos), 48° C. (for 17-base oligos), 55° C. (for 20-base oligos), and 60° C. (for 23-base oligos).

The term "recombinant," when used herein to refer to a polypeptide or protein, means that a polypeptide or protein is derived from recombinant (e.g., microbial or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *E. coli,* will be free of glycosylation modifications; polypeptides or proteins expressed in yeast will have a glycosylation pattern in general different from those expressed in mammalian cells.

The term "recombinant expression vehicle or vector" refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "open reading frame," ORF, means a series of nucleotide triplets coding for amino acids without any termination codons and is a sequence translatable into protein.

The term "expression modulating fragment," EMF, means a series of nucleotides which modulates the expression of an operably linked ORF or another EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments which induce the expression or an operably linked ORF in response to a specific regulatory factor or physiological event.

As used herein, an "uptake modulating fragment," UMF, means a series of nucleotides which mediate the uptake of a linked DNA fragment into a cell. UMFs can be readily identified using known UMFs as a target sequence or target motif with the computer-based systems described below.

The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

The term "active" refers to those forms of the polypeptide which retain the biologic and/or immunologic activities of any naturally occurring polypeptide.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "derivative" refers to polypeptides chemically modified by such techniques as ubiquitination, labeling (e.g., with radionuclides or various enzymes), pegylation (derivatization with polyethylene glycol) and insertion or substitution by chemical synthesis of amino acids such as ornithine, which do not normally occur in human proteins.

The term "recombinant variant" refers to any polypeptide differing from naturally occurring polypeptides by amino acid insertions, deletions, and substitutions, created using recombinant DNA techniques. Guidance in determining which amino acid residues may be replaced, added or deleted without abolishing activities of interest, such as cellular trafficking, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 20% (i.e., the number of individual residue substitutions, additions, and/or deletions in a substantially equivalent sequence, as compared to the corresponding reference sequence, divided by the total number of residues in the substantially equivalent sequence is about 0.2 or less). Such a sequence is said to have 80% sequence identity to the listed sequence. In one embodiment, a substantially equivalent, e.g., mutant, sequence of the invention varies from a listed sequence by no more than 10% (90% sequence identity); in a variation of this embodiment, by no more than 5% (95% sequence identity); and in a further variation of this embodiment, by no more than 2% (98% sequence identity).

Substantially equivalent, e.g., mutant, amino acid sequences according to the invention generally have at least 95% sequence identity with a listed amino acid sequence, whereas substantially equivalent nucleotide sequence of the invention can have lower percent sequence identities, taking into account, for example, the redundancy or degeneracy of the genetic code. For the purposes of the present invention, sequences having substantially equivalent biological activity and substantially equivalent expression characteristics are considered substantially equivalent. For the purposes of determining equivalence, truncation of the mature sequence (e.g., via a mutation which creates a spurious stop codon) should be disregarded.

Nucleic acid sequences encoding such substantially equivalent sequences, e.g., sequences of the recited percent identities, can routinely be isolated and identified via standard hybridization procedures well known to those of skill in the art.

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any polypeptide must have sufficient length to display biologic and/or immunologic activity.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide, to modify the properties of any part of the polypeptide, to change characteristics such as ligand-binding affinities, interchain affinities, or degradation/turnover rate.

The term "activated" cells as used in this application are those which are engaged in extracellular or intracellular membrane trafficking, including the export of neurosecretory or enzymatic molecules as part of a normal or disease process.

The term "purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "infection" refers to the introduction of nucleic acids into a suitable host cell by use of a virus or viral vector.

The term "transformation" means introducing DNA into a suitable host cell so that the DNA is replicable, either as an extrachromosomal element, or by chromosomal integration.

The term "transfection" refers to the taking up of an expression vector by a suitable host cell, whether or not any coding sequences are in fact expressed.

The term "intermediate fragment" means a nucleic acid between 5 and 1000 bases in length, and preferably between 10 and 40 bp in length.

The term "secreted" includes a protein that is transported across or through a membrane, including transport as a result of signal sequences in its amino acid sequence when it is expressed in a suitable host cell. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum. "Secreted" proteins are also intended to include proteins containing non-typical signal sequences (e.g. Interleukin-1 Beta, see Krasney, P. A. and Young, P. R. (1992) Cytokine 4(2): 134–143) and factors released from damaged cells (e.g. Interleukin-1 Receptor Antagonist, see Arend, W. P. et. al. (1998) Annu. Rev. Immunol. 16:27–55)

Each of the above terms is meant to encompasses all that is described for each, unless the context dictates otherwise.

Nucleic Acids and Polypeptides of the Invention

Nucleotide and amino acid sequences of the invention are reported below. Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein-IgM fusion would generate a decavalent form of the protein of the invention.

The present invention also provides both full-length and mature forms (for example, without a signal sequence or precursor sequence) of the disclosed proteins. The full-length form of the such proteins is identified in the sequence listing by translation oil the nucleotide sequence of each disclosed clone. The mature form of such protein may be obtained by expression of the disclosed full-length polynucleotide in a suitable mammalian cell or other host cell. The sequence of the mature form of the protein is also determinable from the amino acid sequence of the full-length form. Where protein of the present invention is membrane bound, soluble forms of the protein are also provided. In such forms part or all of the regions causing the protein to be membrane bound are deleted so that the protein is fully secreted from the cell in which it is expressed.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. Species homologs of the disclosed polynucleotides and proteins are also provided by the present invention. Species homologs may be isolated and identified by making suitable probes or primers from the sequences provided herein and screening a suitable nucleic acid source from the desired species. The invention also encompasses allelic variants of the disclosed polynucleotides or proteins; that is, naturally-occurring alternative forms of the isolated polynucleotide which also encode proteins which are identical, homologous or related to that encoded by the polynucleotides. The compositions of the present invention include isolated polynucleotides, including recombinant DNA molecules, cloned genes or degenerate variants thereof, especially naturally occurring variants such as allelic variants, novel isolated polypeptides, and antibodies that specifically recognize one or more epitopes present on such polypeptides. Species homologs of the disclosed polynucleotides and proteins are also provided by the present invention. Species homologs may be isolated and identified by making suitable probes or primers from the sequences provided herein and screening a suitable nucleic acid source from the desired species. The invention also encompasses allelic variants of the disclosed polynucleotides or proteins; that is, naturally-occurring alternative forms of the isolated polynucleotide which also encode proteins which are identical, homologous or related to that encoded by the polynucleotides.

Nucleic Acids of the Invention

The isolated polynucleotides of the invention include, but are not limited to, a polynucleotide encoding a polypeptide comprising the amino acid sequence of SEQ ID NOS: 3 or 5.

The isolated polynucleotides of the invention further include, but are not limited to a polynucleotide comprising the nucleotide sequence of SEQ ID NOS: 1, 2, 4, or 6; a polynucleotide comprising the full length protein coding sequence of SEQ ID NOS: 1, 2, 4, or 6, and; a polynucleotide comprising the nucleotide sequence of the mature protein coding sequence of SEQ ID NOS: 1, 2, 4, or 6. The polynucleotides of the present invention also include, but are not limited to, a polynucleotide that hybridizes to the complement of the nucleotide sequence of SEQ ID NOS: 1, 2, 4, or 6 under stringent hybridization conditions; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ ID NOS: 1, 2, 4, or 6.

The isolated polynucleotides of the invention further include, but are not limited to a polynucleotide comprising the nucleotide sequence of the genomic clone SEQ ID NOS: 7 or 8; a polynucleotide assembled from one or more of the exons of SEQ ID NOS: 7 or 8 (e.g., alternative splicing); a polynucleotide assembled from one or more of the introns of SEQ ID NOS: 7 or 8; a polynucleotide assembled from one or more of the exons of SEQ ID NOS: 7 or 8 and one or more of the introns of SEQ ID NOS: 7 or 8; a polynucleotide comprising the full length protein coding sequence of SEQ ID NOS: 7 or 8; a polynucleotide comprising the nucleotide sequence of the mature protein coding sequence of SEQ ID NOS: 7 or 8.

The polynucleotides of the present invention also include, but are not limited to, a polynucleotide that hybridizes to the complement of the nucleotide sequence of SEQ ID NOS: 7 or 8 under stringent hybridization conditions; a polynucleotide that hybridizes to the complement of any one of the introns or exons of SEQ ID NOS: 7 or 8 under stringent hybridization conditions; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ ID NOS: 7 or 8.

The polynucleotides of the present invention still further include, but are not limited to, a polynucleotide comprising the nucleotide sequence of the cDNA insert of clone pIL-1Hy deposited with the American Type Culture Collection (ATCC; 10801 University Blvd., Manassas, Va., 20110-2209, U.S.A.); a polynucleotide comprising a nucleotide sequence encoding the amino acid sequence of SEQ ID NO: 3 or 5 which polynucleotide is assembled from the cDNA insert of clone pIL-1Hy273; a polynucleotide comprising the full length protein coding sequence of SEQ ID NO: 3 or 5 which polynucleotide is assembled from the cDNA insert of clone pIL-1Hy273; or, a polynucleotide comprising the nucleotide sequence of the mature protein coding sequence of SEQ ID NO): 3 or 5.

The polynucleotides of the invention additionally include the complement of any of the polynucleotides recited above.

The polynucleotides of the invention also provide polynucleotides including nucleotide sequences that are substantially equivalent to the polynucleotides recited above. Polynucleotides according to the invention can have at least about 80%, more typically at least about 90%, and even more typically at least about 95%, sequence identity to a polynucleotide recited above. The invention also provides the complement of the polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, NY). Useful nucleotide sequences for joining to polypeptides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The polynucleotides of the present invention also make possible the development, through, e.g., homologous recombination or knock out strategies, of animals that fail to express functional IL-1Hy1 or that express a variant of IL-1Hy1. Such animals are useful as models for studying the in vivo activities of IL-1Hy1 as well as for studying modulators of IL-1Hy1.

Knowledge of IL-1Hy1 DNA sequences allows for modification of cells to permit, or increase, expression of endogenous IL-1Hy1. Cells can be modified (e.g., by homologous recombination) to provide increased IL-1 Hy1 expression by replacing, in whole or in part, the naturally occurring IL-1 Hy1 promoter with all or part of a heterologous promoter so that the cells express IL-1Hy1 at higher levels. The heterologous promoter is inserted in such a manner that it is operatively linked to IL-1Hy1 encoding sequences. See, for example, PCT International Publication No. WO94/12650, PCT International Publication No. WO92/20808, and PCT International Publication No. WO91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the IL-1Hy1 coding sequence, amplification of the marker DNA by standard selection methods results in co-amplification of the IL-1Hy1 coding sequences in the cells.

The sequences falling within the scope of the present invention are not limited to the specific sequences herein described, but also include allelic variations thereof. Allelic variations can be routinely determined by comparing the sequence provided in SEQ ID NOS: 1, 2, 4, 6, 7 or 8, a representative fragment thereof, or a nucleotide sequence at least 99.9% identical to SEQ ID NOS: 1, 2, 4, 6, 7, or 8, with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated. Any specific sequence disclosed herein can be readily screened for errors by resequencing a particular fragment, such as an ORF, in both directions (i.e., sequence both strands).

The present invention further provides recombinant constructs comprising a nucleic acid having the sequence of SEQ ID NOS: 1, 2, 4, 6, 7 or 8, or a fragment thereof. The recombinant constructs of the present invention comprise a vector, such as a plasmid or viral vector, into which a nucleic acid having the sequence of SEQ ID NOS: 1, 2, 4, 6, 7 or 8 or a fragment thereof is inserted, in a forward or reverse orientation. In the case of a vector comprising one of the ORFs of the present invention, the vector may further comprise regulatory sequences, including for example, a promoter, operably linked to the ORF. For vectors comprising the EMFs and UMFs of the present invention, the vector may further comprise a marker sequence or heterologous ORF operably linked to the EMF or UMF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotec, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

Included within the scope of the nucleic acid sequences of the invention are nucleic acid sequences that hybridize under stringent conditions to a fragment of the DNA sequence in FIGS. 2, 5, 8, or 9 or its complement, which fragment is greater than about 10 bp, preferably 20–50 bp, and even greater than 100 bp. In accordance with the invention, polynucleotide sequences which encode the novel nucleic acids, or functional equivalents thereof, may be used to generate recombinant DNA molecules that direct the expression of that nucleic acid, or a functional equivalent thereof, in appropriate host cells.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the nucleic acids are preferably constructed by mutating the polynucleotide to give an amino acid sequence that does not occur in nature. These amino acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells.

In a preferred method, polynucleotides encoding the novel nucleic acids are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Edelman et al., DNA 2:183 (1983). A versatile and efficient method for producing site-specific changes in a polynucleotide sequence was published by Zoller and Smith, Nucleic Acids Res. 10:6487–6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives the desired amino acid variant.

A further technique for generating amino acid variants is the cassette mutagenesis technique described in Wells et al., Gene 34:315 (1985); and other mutagenesis techniques well known in the art, such as, for example, the techniques in Sambrook et al., supra, and Current Protocols in Molecular Biology, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

Hosts

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al., *Basic Methods in Molecular Biology* (1986)). The host cells containing one of polynucleotides of the invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as *E. coli* and *B. subtilis*. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell tines. Mammalian expression vectors will comprise an origin of replication, a suitable promoter and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals. mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

Polypeptides of the Invention

SEQ ID NO: 2 encodes the polypeptide sequence of SEQ ID NO: 3. An amino acid alignment of SEQ ID NO: 3 and rat, mouse, rabbit and human Interleukin-1 receptor antagonist polypeptides is shown FIG. 1. SEQ ID NO: 3 displays significant (71%) amino acid homology with human Interleukin-1 receptor antagonist, and thus, represents a novel molecule that is highly related to, yet distinct from Interleukin-1 receptor antagonist. This is the first cloned sequence of an Interleukin-1 receptor antagonist related gene. This discovery of SEQ ID NO: 3 indicates that a family of Interleukin-1 receptor antagonist related genes exists. Additional family members can be identified using SEQ ID NO: 1 or 2 as a molecular probe. SEQ ID NO: 3 encodes a protein that contains a 4 amino acid insertion differing from all other previously characterized Interleukin-1 receptor antagonists sequences (FIG. 1). This insertion may provide SEQ ID NO: 3 with a novel and previously uncharacterized activity. Likewise, FIG. 7 presents an amino acid alignment of SEQ ID NO: 5 with the cytoplasmic form of human IL-1 Ra (labeled "HUMIL1RASIC"). The alignment reveals a high degree of homology between the two; 48% of the amino acids were identical and 54% represent conservative amino acid substitutions.

Interleukin-1 has pleiotropic biological activities many of which adversely affect the organism, it would be expected that the molecule must be tightly regulated if it is not to be injurious. Indeed, there are several reports of Interleukin-1 inhibitors that regulate the action of Interleukin-1. Interleukin-1 inhibitory activity has been reported in monocyte conditioned medium, wherein the monocytes are grown on adherent immune complexes. Arena, W. P., et al., 1985, Journal of Immun., 134:3868. Additionally, an inhibitor has been reported to be present urine. Seckinger, P., et al., 1987, Journal of Immun., 139:1546. Lastly, a protein inhibitor, purified and cloned, that has interleukin-1 receptor antagonist activity has been reported. Hannum, et at., 1990, Nature, 343:336, and Eisenberg, S., et al., 1990, Nature, 343:341.

It is thought that the Interleukin-1 inhibitor present in urine, and which has been partially purified and characterized by Seckinger, P. et al., and Seckinger, P., et al., 1987, Journal of Immun., 139:1541 is similar, if not identical to the cloned Interleukin-1 receptor antagonist reported by Eisenberg, S., et al. (1990), Nature, 343:341; and Carter, D., et al (1990), Nature, 344:633.

Interleukin-1 receptor antagonist is a naturally occurring peptide secreted by macrophages in response to many of the same stimuli which cause the secretion of Interleukin-1 itself. Interleukin-1 receptor antagonist is a naturally occurring antagonist to the cytokines and recognizes receptors on various cell types and blocks Interleukin-1 mediated responses by occupying the receptor. (Wakabayashi et al., FASEB J 1991;5:338; Okusawa et al. J Clin Invest 1988;81:1162; Ohlsson et al., Nature 1990;348:550; Aiura, et al. Cytokine 1991;4:498; Fischer et al. Am J Physiol 1991;261:R442). In humans, Interleukin-1 receptor antagonist is a naturally occurring group of molecules; three forms have been characterized (two glycosylated and one nonglycosylated).

Fischer et al. (Am J Physiol 1991;261:R442) demonstrated that the administration of a naturally occurring antagonist to Interleukin-1 will significantly blunt the cytokine cascade and improve survival in baboons given a lethal dose of live bacteria. Interleukin-1 receptor antagonist significantly attenuates the decrease in mean arterial pressure and cardiac output and improves survival for severe acute pancreatitis. (U.S. Pat. No. 5,508,262) The systemic Interleukin-1 response observed as a result of bacterial sepsis was also diminished significantly, correlating with a decrease in the systemic response to bacterial sepsis.

Studies by Aiura et al. 9 Cytokine 1991;4:498) have shown that Interleukin-1 receptor antagonist is protective in a rabbit model of hypotensive gram-positive septic shock. The administration of Interleukin-1 receptor antagonist in this animal model has been shown to maintain mean arterial pressure compared to control, as well as decreasing lung water and maintaining urine output. This work demonstrated the role of Interleukin-1 and the protective role of Interleukin-1 receptor antagonist in gram-positive septic shock. Interleukin-1 is the principal mediator in a patient's clinical response to multiple different stresses regardless of the etiology (including acute pancreatitis, sepsis, endotoxin shock, and cytokine induced shock).

The isolated polypeptides of the invention include, but are not limited to, a polypeptide comprising the amino acid sequence of SEQ ID NOS: 3 or 5; a full length protein coding sequence of SEQ ID NOS: 3 or 5; a mature protein coding sequence of SEQ ID NOS: 3 or 5, or; a polypetide encoded by one or more of the exons of SEQ ID NOS: 7 or 8.

The polypeptides of the present invention further include, but are not limited to, a polypeptide comprising the amino acid sequence encoded by the cDNA insert of clone pIL-1Hy273 deposited with the American Type Culture Collection (ATCC; 10801 University Blvd., Manassas, Va., 20110-2209, U.S.A.); a full length protein of SEQ ID NO: 3 or 5 assembled from the amino acid sequence encoded by the cDNA insert of clone pIL-1Hy273; or, a mature protein coding sequence of SEQ ID NO: 3 or 5 assembled from the amino acid sequence encoded by cDNA insert of clone pIL-1Hy273.

Protein compositions of the present invention may further comprise an acceptable carrier, such as a hydrophilic, e.g., pharmaceutically acceptable, carrier.

The invention also relates to methods for producing a polypeptide comprising growing a culture of the cells of the invention in a suitable culture medium, and purifying the protein from the culture. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, and further purified. Preferred embodiments include those in which the protein produced by such process is a full length or mature form of the protein.

The invention further provides a polypeptide including an amino acid sequence that is substantially equivalent to SEQ ID NOS: 3 or 5. Polypeptides according to the invention can have at least about 95%, and more typically at least about 98%, sequence identity to SEQ ID NOS: 3 or 5.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins. A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, Protein Purification: Principles and Practice, Springer-Verlag (1994); Sambrook, et al., in Molecular Cloning: A Laboratory Manual; Ausubel et al., Current Protocols in Molecular Biology.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention. The purified polypeptides can be used in in vitro binding assays which are well known in the art to identify molecules which bind to the polypeptides. These molecules include but are not limited to, for e.g., small molecules, molecules from combinatorial libraries, antibodies or other proteins. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

In addition, the binding molecules may be complexed with toxins, e.g., ricin or cholera, or with other compounds that are toxic to cells. The toxin-binding molecule complex is then targeted to a tumor or other cell by the specificity of the binding molecule for SEQ ID NO: 3 or 5.

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat.RTM. kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl.RTM. or Cibacrom blue 3GA Sepharose.RTM.; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.). Pharmacia (Piscataway, N.J.) and In Vitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The polypeptides of the invention include Interleukin-1 Receptor Antagonist (IL-1 RA) analogs. This embraces fragments of IL-1 RA of the invention, as well as Interleukin-1 Receptor Antagonists which comprise one or more amino acids deleted, inserted, or substituted. Also, analogs of Interleukin-1 Receptor Antagonist of the invention embrace fusions of Interleukin-1 Receptor Antagonist or modifications of Interleukin-1 Receptor Antagonist, wherein the Interleukin-1 Receptor Antagonist or analog is fused to another moiety or moieties, e.g., targeting moiety or another therapeutic agent. Such analogs may exhibit improved properties such as activity and/or stability. Examples of moieties which may be fused to Interleukin-1 Receptor Antagonist or an analog include, for example, targeting moieties which provide for the delivery of polypeptide to pancreatic cells, e.g., antibodies to pancreatic cells, antibodies to immune cells such as T-cells, monocytes, dendritic cells, granulocytes, etc., as well as receptor and ligands expressed on pancreatic or immune cells. Other moieties which may be fused to Interleukin-1 Receptor Antagonist include therapeutic agents which are used for treatment, for example, immunosuppressive drugs such as cyclosporin, SK506, azathioprine, CD3 antibodies and steroids. Also, Interleukin-1 Receptor Antagonist may be fused to immunostimulants, immune modulators, and other cytokines such as alpha or beta interferon.

Gene Therapy

Mutations in the IL-1Hy1 gene that result in loss of normal function of the IL-1Hy1 gene product underlie IL-1Hy1-related human disease states. The invention comprehends gene therapy to restore IL-1Hy1 activity that would thus be indicated in treating those disease states. Delivery of a functional IL-1Hy1 gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, Nature, supplement to vol. 392, no 6679, pp. 25–30 (1998). For additional reviews of gene therapy technology, see Friedmann, Science, 244: 1275–1281 (1989); Verma, Scientific American: 68–84 (1990); and Miller, Nature, 357: 455–460 (1992). Alternatively, it is contemplated that in other human disease states, preventing the expression of or inhibiting the activity of IL-1Hy1 will be useful in treating the disease states. It is contemplated that antisense therapy or gene therapy could be applied to negatively regulate the expression of IL-1Hy1.

Deposit of Clone

The following clone, pIL-1Hy 273 was deposited with the American Type Culture Collection (ATCC) 10801 University Avenue, Manassas, Va., on Mar. 12, 1999 under the terms of the Budapest Treaty. The 2,648 base pair cDNA insert of clone pIL-1Hy 273 is contained in vector pSPORT1 and is flanked by Not1 and Sal1 restriction sites. The clone represent a plasmid clone as described in the Examples set forth below.

| Microorganism/Clone | ATCC Accession No. |
| --- | --- |
| pIL-1Hy 273 | 203841 |

Uses and Biological Activity

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. A polynucleotide of the invention can encode a polypeptide exhibiting such attributes. Many protein factors discovered to date, including all known cytokines, have exhibited activity in one or more factor-dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e and CMK. The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., I. Immunol. 149:3778–3783, 1992; Bowman et al., I. Immunol. 152:1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1–3.12.14, John Wiley and Sons, Toronto. 1994; and Measurement of mouse and human interleukin gamma., Schreiber, R. D. In Current Protocols in Immunology. J. E. e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1–6.3.12, John Wiley and Sons, Toronto. 1991; deVries et al., J. Exp. Med. 173: 1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6-Nordan, R. In Current Protocols in Immunology. J. E. e.a. Coligan eds. Vol 1 pp. 6.6.1–6.6.5, John Wiley and Sons, Toronto. 1991; Smith et al., Proc. Natl. Aced. Sci. U.S.A. 83:1857–1861, 1986; Measurement of human Interleukin 11—Bennett, F., Giannotti, J., Clark, S. C. and Turner, K. J. In Current Protocols in Immunology. J. E. e.a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In Current Protocols in Immunology. J. E. e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Immune Stimulating or Suppressing Activity

A protein of the present invention may also exhibit immune stimulating or immune suppressing activity, including without limitation the activities for which assays are described herein. A polynucleotide of the invention can encode a polypeptide exhibiting such activities. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpes viruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to modulate immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a therapeutic composition of the invention may prevent cytokine synthesis by immune cells, such as T cells, and thus acts as an immunosuppressant. Moreover, a lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular therapeutic compositions in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4lg fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of therapeutic compositions of the invention on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block stimulation of T cells can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (e.g., a B lymphocyte antigen function), as a means of up regulating immune responses, may also be useful in therapy. Upregulation of immune responses may be in the form of enhancing an existing immune response or eliciting an initial immune response. F-or example, enhancing an immune response may be useful in cases of viral infection, including systemic viral diseases such as influenza, the common cold, and encephalitis.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

A peptide of the present invention may provide the necessary stimulation signal to T cells to induce a T cell mediated immune response against the transfected tumor cells. In addition, tumor cells which lack MHC class I or MHC class II molecules, or which fail to reexpress sufficient mounts of MHC class I or MHC class II molecules, can be transfected with nucleic acid encoding all or a portion of (e.g., a cytoplasmic-domain truncated portion) of an MHC class I $\alpha$. chain protein and $\beta$.sub.2 microglobulin protein or an MHC class II $\alpha$. chain protein and an MHC class II $\beta$. chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., I. Immunol. 137:3494–3500, 1986; Takai et al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D.. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15: 141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lymphohematopoiesis) include, without limitation, those described in: Methylcellulose colony forming assays, Freshney, M. G. In Culture of Hematopoietic Cells. R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In Culture of Hematopoietic Cells. R. I. Freshney, et al. eds. Vol pp. 23–39, Wiley-Liss, Inc., New York, N.Y. 1994;

Neben et al., Experimental Hematology 22:353–359, 1994; Cobblestone area forming cell assay, Ploemacher, R. E. In Culture of Hematopoietic Cells. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In Culture of Hematopoietic Cells. R. I. Freshney, et al. eds. Vol pp. 163–179, Wiley-Liss, Inc., New York, N.Y. 1994; Long term culture initiating cell assay, Sutherland, H. J. In Culture of Hematopoietic Cells. R. I. Freshney, et al. eds. Vol pp. 139–162, Wiley-Liss, Inc., New York, N.Y. 1994.

Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, Epidermal Wound Healing, pps. 71–112 (Maibach, H. I. and Rovee, D. T., eds.), Year Book Medical Publishers, Inc., Chicago, as modified by Eaglstein and Mertz, J. Invest. Dermatol 71:382–84 (1978).

Activin/Inhibin Activity

A protein of the present invention may also exhibit activin- or inhibin-related activities. A polynucleotide of the invention may encode a polypeptide exhibiting such characteristics. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin α-family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. A polynucleotide of the invention can encode a polypeptide exhibiting such attributes. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Marguiles, E. M. Shevach, W. Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25:1744–1748; Gruber et al. J. of Immunol. 152:5860–5867, 1994; Johnston et al. J. of Immunol. 153:1762–1768, 1994.

Hemostatic and Thrombolytic Activity

A protein of the invention may also exhibit hemostatic or thrombolytic activity. A polynucleotide of the invention can encode a polypeptide exhibiting such attributes. Such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

Receptor/Ligand Activity

A protein of the present invention may also demonstrate activity as receptors, receptor ligands or inhibitors or agonists of receptor/ligand interactions. A polynucleotide of the invention can encode a polypeptide exhibiting such characteristics. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selecting, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptoriligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

By way of example, the novel Interleukin-1 Receptor Antagonist of the invention may be used as a ligand for a cytokine receptor thereby modulating the biological activity of that receptor. Examples of cytokine receptors that may be used include, but are not limited to, the Interleukin-1 Type I or the Interleukin-Type II Receptor. Whether the novel Interleukin-1 Receptor Antagonist of the invention exhibits agonist, partial agonist, antagonist, or partial antagonist activity for a particular receptor, such as a cytokine receptor, in a particular cell type can be determined by conventional techniques known to those skilled in the art. In one embodiment, one or more cells expressing a cytokine receptor (e.g., Interleukin-1 Type I or Type II Receptors) are contacted with the protein of the invention. Examples of cells that may be contacted with the protein of the invention include, but are not limited to, mammalian cells such as fibroblasts and T-cells. Preferably the novel protein of the invention acts as an antagonist for a cytokine receptor (e.g.-the Interleukin-I Receptor) so that the biological activities of that receptor are inhibited.

Studies characterizing drugs or proteins as agonist or antagonist or partial agonists a partial antagonist require the use of other proteins as competing ligands. The novel protein of the present invention exhibit an affinity for Interleukin-1 Receptor. Thus, the proteins of the present invention may be used, for example, as competitors in assays involving Interleukin-1 Receptors (e.g., Example 12). Alternatively ,the protein of the invention may be labeled by being coupled to radioisotopes, colorimetric molecules or a toxin molecules by conventional methods. ("Guide to Protein Purification" Murray P. Deutscher (ed) Methods in Enzymology Vol. 182 (1990) Academic Press, Inc. San Diego) and used in both in vivo and in vitro to bind to the Interleukin-1 Receptor. Examples of radioisotopes include, but are not limited to, tritium and carbon-14. Examples of colorimetric molecules include, but are not limited to, fluorescent molecules such as fluorescamine, or rhodamine or other colorimetric molecules. Examples of toxins include, but are not limited, to riacin. By way of example, the proteins coupled to such molecules are useful in studies involving in vivo or in vitro metabolism of the Interleukin-1 Receptor.

Drug Screening with the Novel interleukin-1 Receptor Antagonist Polypeptides

This invention is particularly useful for screening compounds by using the novel Interleukin-1 Receptor Antagonist polypeptides or binding fragments thereof in any of a variety of drug screening techniques. The novel Interleukin-1 receptor antagonist polypeptides or fragments employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between novel Interleukin-1 receptor antagonist polypeptides or fragments and the agent being tested or examine the diminution in complex formation between the novel Interleukin-1 receptor antagonist polypeptides and an appropriate cell line, which are well known in the art.

Assay for Anti-Interleukin-1 Receptor Activity

In one embodiment, the Interleukin-1 receptor antagonist activity of the polypeptides of the invention is determined using a method that involve (1) forming a mixture comprising Interleukin-1, the Interleukin-1 receptor, and the Interleukin-1 receptor antagonist polypeptides of the invention and/or its agonists and antagonists (or agonist or antagonist drug candidates) and/or antibodies specific for the Interleukin-1 receptor antagonist polypeptides of the invention; (2) incubating the mixture under conditions whereby, but for the presence of said Interleukin-1 receptor antagonist polypeptide of the invention and/or its agonists and antagonists (or agonist or antagonist drug candidates) and/or antibodies specific for the Interleukin-1 receptor antagonist polypeptides of the invention, the Interleukin-1 binds to the Interleukin-1 receptor; and (3) detecting the presence or absence of specific binding of Interleukin-1 to the Interleukin-1 receptor.

Assay for Antagonists and Agonists

Human HepG2 cells are incubated at 37 degree(s) C. for 18–24 hours in serum-free Dulbecco's modified Eagle medium. Separate monolayers of cells are incubated in the same medium supplemented with Interleukin-1 at various concentrations and in the same medium supplemented with Interleukin-1 receptor antagonists of the invention at various concentrations.

Monolayers are rinsed vigorously with isotonic buffer and incubated in (35-S) methionine, 250 mu ci/ml methionine-free medium and pulsed for a period of 15–30 minutes to assess net synthesis. Cell culture fluid is discarded and monolayers are again rinsed and resuspended in cell lysis buffer. The newly synthesized radiolabeled hepatic proteins in these cell lysates are detected by immunoprecipitation, SDS-PAGE and fluorography.

Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation intimation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material. In particular, the Interleukin-1 receptor antagonist of this invention may be utilized to prevent or treat condition such as, but not limited to, utilized, for example, as part of methods for the prevention and/or treatment of disorders involving sepsis, acute pancreatitis, endotoxic shock, cytokine induced shock, rheumatoid arthritis, chronic inflammatory arthritis, pancreatic cell damage from diabetes mellitus type 1, graft versus host disease, inflammatory bowel disease, inflamation associated with pulmonary disease, other autoimmune disease or inflammatory disease, an anti-proliferative agent such as for acute or chronic mylegenous leukemia or in the prevention of premature labor secondary to intrauterine infections.

Leukemias

Leukemias and related disorders may be treated or prevented by administration of a therapeutic that promotes or inhibits function of the polynucleotides and/or polypeptides of the invention. Such leukemias and related disorders include but are not limited to acute leukemia, acute lymphocytic: leukemia, acute myelocytic leukemia, myeloblastic, promyelocytic, myelomonocytic, monocytic, erythroleukemia, chronic leukemia, chronic myelocytic (granulocytic) leukemia and chronic lymphocytic leukemia (for a review of such disorders, see Fishman et al., 1985, Medicine, 2d Ed., J. B. Lippincott Co., Philadelphia).

Nervous System Disorders

Nervous system disorders, involving cell types which can be tested for efficacy of intervention with compounds that modulate the activity of the polynucleotides and/or polypeptides of the invention, and which can be treated upon thus observing an indication of therapeutic utility, include but are not limited to nervous system injuries, and diseases or disorders which result in either a disconnection of axons, a diminution or degeneration of neurons, or demyelination.

Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(iv) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(v) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vi) neurological lesions associated with systemic diseases including but not limited to diabetes (diabetic neuropathy, Bell's palsy), systemic lupus erythematosus, carcinoma, or sarcoidosis;

(vii) lesions caused by toxic substances including alcohol, lead, or particular neurotoxins; and (viii) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons. For example, and not by way of limitation, therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo. Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, co-factors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

Therapeutic Methods

The novel Interleukin-1 Receptor Antagonist of the invention has numerous applications in a variety of therapeutic methods. Examples of therapeutic applications include, but are not limited to, those exemplified below.

Sepsis

One embodiment of the invention is the administration of an effective amount of the Interleukin-1 receptor antagonist polypeptides of the invention to individuals that are at a high risk of developing sepsis, or that have developed sepsis. An example of the former category are patients about to undergo surgery. While the mode of administration is not particularly important, parenteral administration is preferred because of the rapid progression of sepsis, and thus, the need to have the inhibitor disseminate quickly throughout the body. Thus, the preferred mode of administration is to deliver an I.V. bolus slightly before, during, or after surgery. The dosage of the Interleukin-1 receptor antagonist polypeptides of the invention will normally be determined by the prescribing physician. It is to be expected that the dosage will vary according to the age, weight and response of the individual patient. Typically, the amount of inhibitor administered per dose will be in the range of about 0.1 to 25 mg/kg of body weight, with the preferred dose being about 0.1 to 10 mg/kg of patient body weight. For parenteral administration, the Interleukin-1 receptor antagonist polypeptides of the invention will be formulated in an injectable form combined with a pharmaceutically acceptable parenteral vehicle. Such vehicles are well known in the art and examples include water, saline, Ringer's solution, dextrose solution, and solutions consisting of small amounts of the human serum albumin. The vehicle may contain minor amounts of additives that maintain the isotonicity and stability of the inhibitor. The preparation of such solutions is within the skill of the art. Typically, the cytokine inhibitor will be formulated in such vehicles at a concentration of about 1–8 mg/ml to about 10 mg/ml.

Arthritis and Inflammation

The immunosuppressive effects of the Interleukin-1 inhibitor against rheumatoid arthritis is determined in an experimental animal model system. The experimental model system is adjuvant induced arthritis in rats, and the protocol is described by J. Holoshitz, et at., 1983, Science, 219:56, or by B. Waksman et al., 1963, Int. Arch. Allergy Appl. Immunol., 23:129. Induction of the disease can be caused by a single injection, generally intradermally, of a suspension of killed Mycobacterium tuberculosis in complete Freund's adjuvant (CFA). The route of injection can vary, but rats may be injected at the base of the tail with an adjuvant mixture. The inhibitor is administered in phosphate buffered solution (PBS) at a dose of about 1–5 mg/kg. The control consists of administering PBS only.

The procedure for testing the effects of the Interleukin-1 inhibitor would consist of intradermally injecting killed Mycobacterium tuberculosis in CFA followed by immediately administering the inhibitor and subsequent treatment every other day until day 24. At 14, 15, 18, 20, 22, and 24 days after injection of Mycobacterium CFA, an overall arthritis score may be obtained as described by J. Holoskitz above. An analysis of the data would reveal that the inhibitor would have a dramatic affect on the swelling of the joints as measured by a decrease of the arthritis score.

Diabetes

Interleukin-1 has been shown to be involved in the destruction of islet cells in diabetes mellitus (DM) (Mandrup-Paulsen, T., K. Bendtzen, J. Nerup, C. A. Dinarello, M. Svenson, and J. H. Nielson [1986] Diabetologia 29:63–67). The Interleukin-1 receptor antagonist polypeptides of the invention limit lymphocyte and macrophage mediated damage to islet cells in incipient cases of DM identified by disease susceptibility via genetic background and family history. The inflammatory destruction of the pancreatic beta islet cells in such individuals with early DM is reduced by parenterally administering the Interleukin-1 receptor antagonist ;polypeptides of the invention which have an anti-Interleukin-1 effect in the pancreas.

Anti-Hypotensive Arginine-Free Formulations

The parenteral formulation of the therapeutic regimen is defined as including: about 3–4 g/l isoleucine, about 4–6 g/l leucine, about 3–4 g/l lysine, about 1–2 g/l methionine, about 1–2 g/l phenylalanine, about 2–3 g/l threonine, about 0.5–1.5 g/l tryptophan, about 3–4 g/l valine, about 4–5 g/l alanine, about 1–2 g/l histidine, about 3–4 g/l proline, about 1–2 g/l serine, about 0.25–0.75 g/l tyrosine, about 4–5 g/l glycine and about 2–3 g/l aspartic acid, together in a pharmacologically acceptable excipient. In another preferred embodiment of the described parenteral formulation, the formulation may further include ornithine, most particularly at a concentration of about 1–2 g/l. In still another embodiment of the described parenteral formulation, the formulation may include citruline, most preferably at a concentration of between about 1 g/l and about 2 g/l. Both citrulline and ornithine may be included in still another embodiment of the formulation, again at the concentrations indicated.

The method includes an arginine-free formulation which comprises the amino acids and concentrations thereof already described herein, together in a pharmacologically acceptable excipient. Again, the formulation may further include ornithine, citrulline, or both, to even further supply physiologically required concentrations of urea cycle substrates in the animal. Most preferably, the formulation is provided as a parenteral formulation.

Another aspect of the method comprises a method for treating chemotherapeutic agent-related hypotension. In a most preferred embodiment, the method comprises monitoring an animal receiving a chemotherapeutic agent for a decrease in systolic blood pressure to less than about 100 mm Hg to detect an animal with systemic hypotension, treating the animal having systemic hypotension with a therapeutic regimen comprising a therapeutically effective amount of an arginine-free formulation sufficient to reduce plasma or serum arginine concentrations administered concurrently with or followed by the administration of a therapeutically effective concentration of an interleukin-1 receptor antagonist, and maintaining the animal on the therapeutic regimen until an increase of systolic blood pressure to at least about 100 mm Hg is detectable. Most preferably, the arginine-free formulation is a parenteral formulation.

In a preferred embodiment, the interleukin-1 receptor antagonist polypeptide of the invention is used in combination with the anti-hypotensive arginine free formulation to treat hypotension in an animal, particularly that hypotension caused by exposure to endotoxin or septic shock.

A patient having a systolic blood pressure of less than about 100 mm Hg will be targeted for the present treatment. Such a patient is to be placed on a continuous feed of an arginine-free formulation which includes a mixture of essential and nonessential amino acids as described in U.S. Pat. No. 5,334,380. The patient is treated concurrently with the interleukin-1 antagonist polypeptides of the invention. Blood samples are to be obtained from the patient and arginine levels in the serum or plasma fraction are determined.

Pharmaceutical Formulations and Routes of Administration

A protein of the present invention (from whatever source derived, including without limitation from recombinant and non-recombinant sources) may be administered to a patient in need, by itself, or in pharmaceutical compositions where it is mixed with suitable carriers or excipient(s) at doses to treat or ameliorate a variety of disorders. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin.

The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent. A protein of the present invention may be active in multimers (e.g., heterodimers or homodimers) or complexes with itself or other proteins. As a result, pharmaceutical compositions of the invention may comprise a protein of the invention in such multimeric or complexed form.

Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

Alternately, one may administer the compound in a local rather than systemic manner, for example, via injection of the compound directly into a arthritic joints or in fibrotic tissue, often in a depot or sustained release formulation. In order to prevent the scarring process frequently occurring as complication of glaucoma surgery, the compounds may be administered topically, for example, as eye drops. Furthermore, one may administer the drug in a targeted drug delivery system, for example, in a liposome coated with a specific antibody, targeting, for example, arthritic or fibrotic tissue. The liposomes will be targeted to and taken up selectively by the afflicted tissue.

Compositions/Formulations

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the compounds of the invention may be provided as salts with pharmaceutically compatible counterions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention. The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 μg to about 100 mg (preferably about 0.1 μg to about 10 mg, more preferably about 0.1 μg3 to about 1 mg) of protein of the present invention per kg body weight. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone arid/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells. In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-.alpha. and TGF-.beta.), and insulin-like growth factor (IGF).

The therapeutic compositions are also presently valuable for veterinary applications. Particularly domestic animals and thoroughbred horses, in addition to humans, are desired patients for such treatment with proteins of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA). Cells may also be cultured ex vivo in the presence of proteins of the present invention in order to proliferate or to produce a desired effect on or activity in such cells. Treated cells can then be introduced in vivo for therapeutic purposes.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein. For any compound used in the method of the invention, the therapeutically effective dose can be estimated initially from cell culture assays. For example, a dose can be formulated in animal models to achieve a circulating concentration range that includes the $IC_{50}$ as determined in cell culture. Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p.1. Dosage amount and interval may be adjusted individually to provide plasma levels of the active moiety which are sufficient to maintain the desired therapeutic effects, or minimal effective concentration (MEC). The MEC will vary for each compound but can be estimated from in vitro data; for example, the concentration necessary to achieve 50–90% inhibition of cytokine activity using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

Antibodies

Another aspect of the invention is an antibody that specifically binds the polypeptide of the invention. Such antibodies can be either monoclonal or polyclonal antibodies, as well fragments thereof and humanized forms or fully human forms, such as those produced in transgenic animals. The invention further provides a hybridoma that produces an antibody according to the invention. Antibodies of the invention are useful for detection and/or purification of the polypeptides of the invention.

Protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein. In general, techniques for preparing polyclonal and monoclonal antibodies as well as hybridomas capable of producing the desired antibody are well known in the art (Campbell, A. M., Monoclonal Antibodies Technology: Laboratory Techniques in Biochemistry and Molecular Biology, Elsevier Science Publishers, Amsterdam, The Netherlands (1984); St. Groth et al., J. Immunol. 35:1–21 (1990); Kohler and Milstein, Nature 256:495–497 (1975)), the trioma technique, the human B-cell hybridoma technique (Kozbor et al., Immunology Today 4:72 (1983); Cole et al., in Monoclonal Antibodies and Cancer Therapy, Alan R. Liss, Inc. (1985), pp. 77–96).

Any animal (mouse, rabbit, etc.) which is known to produce antibodies can be immunized with a peptide or polypeptide of the invention. Methods for immunization are well known in the art. Such methods include subcutaneous or intraperitoneal injection of the polypeptide. One skilled in the art will recognize that the amount of the protein encoded by the ORF of the present invention used for immunization will vary based on the animal which is immunized, the antigenicity of the peptide and the site of injection. The protein that is used as an immunogen may be modified or administered in an adjuvant in order to increase the protein's antigenicity. Methods of increasing the antigenicity of a protein are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Research. 175:109–124 (1988)).

Hybridomas secreting the desired antibodies are cloned and the class and subclass is determined using procedures known in the art (Campbell, A. M., Monoclonal Antibody Technology: Laboratory Techniques in Biochemistry and Molecular Biology, Elsevier Science Publishers, Amsterdam, The Netherlands (1984)). Techniques described for the production of single chain antibodies (U.S. Pat. No. 4,946,778) can be adapted to produce single chain antibodies to proteins of the present invention.

For polyclonal antibodies, antibody containing antiserum is isolated from the immunized animal and is screened for the presence of antibodies with the desired specificity using one of the above-described procedures. The present invention further provides the above-described antibodies in delectably labeled form. Antibodies can be delectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling are well-known in the art, for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

The labeled antibodies of the present invention can be used for in vitro, in vivo, and in situ assays to identify cells or tissues in which a fragment of the polypeptide of interest is expressed. The antibodies may also be used directly in therapies or other diagnostics. The present invention further provides the above-described antibodies immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., "Handbook of Experimental Immunology" 4th Ed., Blackwell Scientific Publications, Oxford, England, Chapter 10 (1986); Jacoby, W. D. et al., Meth. Enzym. 34 Academic Press, N.Y. (1974)). The immobilized antibodies of the present invention can be used for in vitro, in vivo, and in situ assays as well as for immuno-affinity purification of the proteins of the present invention.

Computer Readable Sequences

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention. As used herein, "recorded" refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the nucleotide sequence information of the present invention. By providing the nucleotide sequence of SEQ ID NOS: 1, 2, 4, 6 or 7 or a representative fragment thereof, or a nucleotide sequence at least 99.9% identical to SEQ ID NOS: 1, 2, 4, 5, 6 or 7 or 8 in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., J. Mol. Biol. 215:403–410 (1990)) and BLAZE (Brutlag et al., Comp. Chem. 17:203–207 (1993)) search algorithms on a Sybase system is used to identify open reading frames (ORFs) within a nucleic acid sequence. Such ORFs may be protein encoding fragments and may be useful in producing commercially important proteins such as enzymes used in fermentation reactions and in the production of commercially useful metabolites.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention. As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of a known sequence which match a particular target sequence or target motif. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTA (NPOLYPEPTIDEIA). A skilled artisan can readily recognize that any one of the available algorithms or implementing software packages for conducting homology searches can be adapted for use in the present computer-based systems. As used herein, a "target sequence" can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Triple Helix Formation

In addition, the fragments of the present invention, as broadly described, can be used to control gene expression through triple helix formation or antisense DNA or RlNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., Nucl. Acids Res. 6:3073 (1979); Cooney et al., Science 15241:456 (1988); and Dervan et al., Science 251:1360 (1991)) or to the mRNA itself (antisense—Olmno, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

Diagnostic Assays and Kits

The present invention further provides methods to identify the presence or expression of one of the ORFs of the present invention, or homolog thereof, in a test sample, using a nucleic acid probe or antibodies of the present invention.

In general, methods for detecting a polynucleotide of the invention can comprise contacting a sample with a compound that binds to and forms a complex with the polynucleotide for a period sufficient to form the complex, and detecting the complex, so that if a complex is detected, a polynucleotide of the invention is detected in the sample. Such methods can also comprise contacting a sample under stringent hybridization conditions with nucleic acid primers that anneal to a polynucleotide of the invention under such conditions, and amplifying annealed polynucleotides, so that if a polynucleotide is amplified, a polynucleotide of the invention is detected in the sample.

In general, methods for detecting a polypeptide of the invention can comprise contacting a sample with a compound that binds to and forms a complex with the polypeptide for a period sufficient to form the complex, and detecting the complex, so that if a complex is detected, a polypeptide of the invention is detected in the sample.

In detail, such methods comprise incubating a test sample with one or more of the antibodies or one or more of nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

Screening Assays

Using the isolated proteins and polynucleotides of the invention, the present invention further provides methods of obtaining and identifying agents which bind to a polypeptide encoded by the ORF from a polynucleotide with a sequence of SEQ ID NOS: 1, 2, 4, 6, 7 or 8 to a specific domain of the polypeptide encoded by the nucleic acid, or to a nucleic acid with a sequence of SEQ ID NOS: 1, 2 4, 6, 7 or 8. In detail, said method comprises the steps of:

(a) contacting an agent with an isolated protein encoded by an ORF of the present invention, or nucleic acid of the invention; and (b) determining whether the agent binds to said protein or said nucleic acid.

In general, therefore, such methods for identifying compounds that bind to a polynucleotide of the invention can comprise contacting a compound with a polynucleotide of the invention for a time sufficient to form a polynucleotide/compound complex, and detecting the complex, so that if a polynucleotide/compound complex is detected, a compound that binds to a polynucleotide of the invention is identified.

Likewise, in general, therefore, such methods for identifying compounds that bind to a polypeptide of the invention can comprise contacting a compound with a polypeptide of the invention for a time sufficient to form a polypeptidel-compound complex, and detecting the complex, so that if a polypeptide/compound complex is detected, a compound that binds to a polynucleotide of the invention is identified.

Methods for identifying compounds that bind to a polypeptide of the invention can also comprise contacting a compound with a polypeptide of the invention in a cell for a time sufficient to form a polypeptide/compound complex, wherein the complex drives expression of a receptor gene sequence in the cell, and detecting the complex by detecting reporter gene sequence expression, so that if a polypeptide/compound complex is detected, a compound that binds a polypeptide of the invention is identified.

Compounds identified via such methods can include compounds which modulate the activity of a polypeptide of the invention (that is, increase or decrease its activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, for example see Hurby et al., Application of Synthetic Peptides: Antisense Peptides, "In Synthetic Peptides, A User's Guide, W. H. Freeman, N.Y. (1992), pp. 289–307, and Kaspczak et al., Biochemistry 28:9230–8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control. One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents. Agents which bind to a protein encoded by one of the ORFs of the present invention can be used as a diagnostic agent, in the control of bacterial infection by modulating the activity of the protein encoded by the ORF. Agents which bind to a protein encoded by one of the ORFs of the present invention can be formulated using known techniques to generate a pharmaceutical composition.

Use of Nucleic Acids as Probes

Another aspect of the subject invention is to provide for polypeptide-specific nucleic acid hybridization probes capable of hybridizing with naturally occurring nucleotide sequences. The hybridization probes of the subject invention may be derived from the nucleotide sequence of the SEQ ID NOS: 1, 2, 4, 6, 7 or 8. Because the corresponding gene is only expressed in a limited number of tissues, especially adult tissues, a hybridization probe derived from SEQ ID NOS: 1, 2, 4, 6, 7, or 8 can be used as an indicator of the presence of RNA of cell type of such a tissue in a sample.

Any suitable hybridization technique can be employed, such as, for example, in situ hybridization. PCR as described U.S. Pat. Nos. 4,683,195 and 4,965,188 provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides. The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals. The nucleotide sequence may be used to produce purified polypeptides using well known methods of recombinant DNA technology. Among the many publications that teach methods for the expression of genes after they have been isolated is Goeddel (1990) Gene Expression Technology, Methods and Enzymology, Vol 185, Academic Press, San Diego. Polypeptides may be expressed in a variety of host cells, either prokaryotic or eukaryotic. Host cells may be from the same species from which a particular polypeptide nucleotide sequence was isolated or from a different species. Advantages of producing polypeptides by recombinant DNA technology include obtaining adequate amounts of the protein for purification and the availability of simplified purification procedures.

Each sequence so obtained was compared to sequences in GenBank using a search algorithm developed by Applied Biosystems and incorporated into the INHERIT™ 670 Sequence Analysis System. In this algorithm, Pattern Specification Language (developed by TRW Inc., Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search. Peptide and protein sequence Homologue were ascertained using the INHERIT™ 670 Sequence Analysis System in a way similar to that used in DNA sequence Homologue. Pattern Specification Language and parameter windows were used to search protein databases for sequences containing regions of homology that were scored with an initial value. Dot-matrix homology plots were examined to distinguish regions of significant homology from chance matches.

Alternatively, BLAST, which stands for Basic Local Alignment Search Tool, is used to search for local sequence alignments (Altschul SF (1993) J Mol Evol 36:290–300; Altschul, SF et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. Whereas it is ideal for matches which do not contain gaps, it is inappropriate for performing motif-style searching. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

In addition, BLAST analysis was used to search for related molecules within the libraries of the LIFESEQ™ database. This process, an "electronic northern" analysis is analogous to northern blot analysis in that it uses one cellubrevin sequence at a time to search for identical or homologous molecules at a set stringency. The stringency of the electronic northern is based on "product score". The product score is defined as (% nucleotide or amino acid [between the query aid reference sequences] in Blast multiplied by the % maximum possible BLAST score [based on the lengths of query and reference sequences]) divided by 100. At a product score of 40, the match will be exact within a 1–2% error; and at 70, the match will be exact. Homologous or related molecules can be identified by selecting those which show product scores between approximately 15 and 30.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples.

EXAMPLES

Example 1
A Novel Interleukin-1 Receptor Antagonist Obtained from a cDNA Library of Fetal Liver-Spleen A plurality of novel nucleic acids were obtained from the $b^2$HFLS20W cDNA library prepared from human fetal liver-spleen tissue, as described in Bonaldo et al., Genome Res. 6:791–806 (1996), using standard PCR, SBH sequence signature analysis and Sanger sequencing techniques. The inserts of the library were amplified with PCR using primers specific for vector sequences which flank the inserts. These samples were spotted onto nylon membranes and interrogated with oligonucleotide probes to give sequence signatures. The clones were clustered into groups of similar or identical sequences, and single representative clones were selected from each group for gel sequencing. The 5' sequence of the amplified inserts was then deduced using the reverse M13 sequencing primer in a typical Sanger sequencing protocol. PCR products were purified and subjected to flourescent dye terminator cycle sequencing. Single pass gel sequencing was done using a 377 Applied Biosystems (ABI) sequencer. Two (2) of these inserts have been identified as novel sequences not previously obtained from this library, and not previously reported in public databases. These sequences are shown in FIG. 2 as SEQ ID NO: 1 and 2. The polypeptide sequences corresponding to these nucleic acid sequences are shown in FIG. 3 as SEQ ID NO: 3. These amino acid sequences have striking homology to Interleukin-1 receptor antagonist.

Example 2
Expression Study Using SEQ ID NO: 2

To study the role of SEQ ID NO: 2 in the regulation of the inflammatory response, gene expression was analyzed using a semi-quantitative polymerase chain reaction-based technique. cDNA libraries were used as sources of expressed genes from tissues of interest (three leukocyte preparations [two stimulated and one unstimulated], heart, lung, spleen, placenta, testes, fetal liver, adult liver, bone marrow, lymph node, macrophages, endothelial cells, fetal skin, and umbilical cord). Gene specific primers were used to amplify portions of the SEQ ID NO: 2 sequence (corresponding to bases 105–772 and 161–690, as numbered from the 5' end of SEQ ID NO: 2) from the samples. Amplified products were separated on an agarose gel, transferred and chemically linked to a nylon filter. The filter was then hybridized with a radioactively labeled ($^{33}$Palpha-dCTP) double-stranded probe generated from the full-length SEQ ID NO: 2 sequence using a Klenow polymerase, random prime method. The filters were washed (high stringency) and used to expose a phosphorimaging screen for several hours. Bands indicated the presence of cDNA including SEQ ID NO: 2 sequences in a specific library, and thus mRNA expression in the corresponding cell type or tissue.

SEQ ID NO: 2 was expressed in a very limited set of human tissues. Of the 16 human tissues tested, fetal skin and umbilical cord were the only samples that provided a signal, indicating that expression of SEQ ID NO: 2 is tightly regulated. Expression of both IL-1 Ra are tightly restricted to a subset of tissues and cell types; both constitutively expressed in skin but not present in other tissues or cell types without stimulation Thus, the expression pattern of SEQ ID NO: 2 parallels that of the IL-1 Ra genes, indicating that the novel cytokine encoded by SEQ ID NO: 2 plays a role in the regulation of the inflammatory response.

Example 3
Chromosomal Localization Study Using SEQ ID NO: 2

Chromosome mapping technologies allow investigators to link genes to specific regions of chromosomes. Chromosomal mapping was performed with the Stanford G3 Radiation Hybrid Panel (Research Genetics). The panel was screened with gene-specific primers (5' primer: CCCCACTGGATGGTGCTACTG; (SEQ ID NO: 15), 3' primer: GGGMGAGATAGGAAAGGTAG) (SEQ ID NO: 16)that generated a sequence tag site (STS), and the results of the PCR screening were submitted to the Stanford Radiation Hybrid mapping email server at the Stanford Human Genome Center (SHGC). The gene position on the radiation hybrid framework map was provided by linking the STS corresponding to SEQ ID NO: 2 with the SHGC marker with best linkage.

The results indicated that SEQ ID NO: 2 is located on the long arm of chromosome 2. The STS was linked to the marker SHGC-7020 with a LOD (log of the odds) score of 12.25 and cR-1000 of 5, indicating that the STS was within 120 kb (kilobases) of this marker. SHGC-7020 is in turn located within 120 kb of the IL-1 Ra gene. Thus, the STS corresponding to SEQ ID NO: 2 is located within about 240 kilobases of the IL-1 Ra gene and could be in close proximity to the IL-1 Ra gene.

Gene family members are often linked to specific regions of chromosomes owing to intrachromosomal gene duplication events that give rise to multimember gene families during the process of evolution. The interleukin-1 gene family has been mapped to chromosome 2. More specifically, all of the interleukin 1 genes (IL-1a, IL-1b) and the receptors (IL-1 RI and IL-1 RII), as well as the receptor antagonist IL-1 Ra, have been found to be situated on the long arm of chromosome 2. The identification of SEQ ID NO: 2 sequences in this same region establishes the physical linkage of SEQ ID NO: 2 to the interleukin-1 locus which evidences that the cytokine encoded by SEQ ID NO: 2 functions as a modulator of the inflammatory response.

Example 4
Intron/Exon Structure of the Locus Corresponding to SEQ ID NO: 2

Members within gene families often maintain genomic organization by virtue of the fact that they arose from a common ancestral precursor. The intron/exon structure of IL-1a, IL-1b and IL-1 Ra have been highly conserved, demonstrating that they probably arose from a common precursor gene. We have isolated a bacterial artificial chromosome (BAC) containing SEQ ID NO: 2. Using gene-specific primers we have sequenced in the 5' direction of the clone, delineating coding sequence (identical to SEQ ID NO: 2) and intronic sequence. The intron/exon structure is identical between IL-1 Ra and the BAC fragment containing SEQ ID NO: 2, providing evidence that these two sequences are members of the same family and were generated from a common gene precursor.

Example 5
Interleukin-1 Receptor Binding Domain and interleukin-1 Receptor Assay The receptor binding region of both IL-1β and IL-1 Ra have been mapped an 18 amino acid region in the carboxy terminal half of the proteins (i.e., residues 88–105 of IL-1β) by site-directed mutagenesis and protein modification studies. An amino acid alignment of SEQ ID NO: 3 with both IL-1β and IL-1 Ra demonstrates that SEQ ID NO: 3 contains a receptor binding region. SEQ ID NO: 3 is 39% identical to IL-1 Ra and 22% identical (39% conserved) with IL-1β in this region. In comparison, IL-1 Ra, which is known to bind to the IL-1 receptor, is 28% identical and 50% conserved with IL-1β in this region. The remarkable similarity between this region of SEQ ID NO: 3 and the receptor binding regions of both IL1β and IL-1Ra indicates that SEQ ID NO: 3 also contains an IL1 receptor binding region. The alignment of all three proteins in the receptor binding region is shown in FIG. 4.

Because SEQ ID NO: 3 contains a IL-1 receptor binding region, SEQ ID NO: 3 and truncated forms of SEQ ID NO: 3 that include the receptor binding region are useful as reagents to identify cells and tissues expressing IL-1 receptors. The IL-1 receptor binding assay described in Hannum et al. Nature 343:336–340 (1990) is used. Briefly, highly radioactive recombinant SEQ ID NO: 3 is prepared by growing E. coli expressing SEQ ID NO: 3 on M9 medium containing [35S] sulphate and purifying the labeled SEQ ID NO: 3 by chromatography on a Mono-S column. The labeled SEQ ID NO: 3 is incubated with the cells or tissue under standard IL-1 binding assay conditions, and [35S] binding. Significant [35S] binding indicates the presence of IL-1 receptors.

Example 6
Determination of a Nucleotide Sequence Encoding a 155-Amino Acid Protein with Sequence Homology to Human interleukin-1 beta and Human Interleukin-1 Receptor Antagonist The nucleotide sequence presented in FIG. 5, and labeled SEQ ID NO: 4, encodes the translated amino acid sequence SEQ ID NO: 5, which is presented in FIG. 6. The extended nucleotide sequence was obtained by isolating PCR products generated from pools of clones from a fetal skin cDNA library. In short, a fetal skin cDNA library was plated on ampicillin containing plates in pools of about 40,000 colonies. The colonies were recovered into LB medium and PCR was used to detect pools which contained SEQ ID NO: 2 (FIG. 2). Two pools were identified. PCR using vector- and gene-specific primers amplified the 5' portion of the cDNA. Nested primers were used to generate sequence from the two amplified products. Laser gene™ software was used to edit and "contig" the partial sequences into a full length sequence.

SEQ ID NO: 4 encodes a protein of 155 amino acids, lacking a typical hydrophobic leader peptide, suggesting that this protein is retained as a cytoplasmic molecule, similar to the cytoplasmic isoform of the human IL-1 Ra gene product. FIG. 7 presents an amino acid alignment of SEQ ID NO: 5 with the cytoplasmic form of human IL-1 Ra (labeled "HUMIL1RASIC"). The alignment reveals a high degree of homology between the two; 48% of the amino acids were identical and 54% represent conservative amino acid substitutions. Three residues have been proven to be critical for receptor activation by IL-1β (marked with asterisks in FIG. 7). The corresponding residues in IL-1 Ra differ, conferring IL-1 Ra's antagonistic activity. These residues are R21, W23, and K152 for IL-1 Ra, and T9, R11, and D145 for the mature IL-1β. SEQ ID NO: 5 possesses a combination of both residues, R10 (identical to the corresponding residue in IL-1 Ra) and K12 and D148 (similar and identical, respectively, to the corresponding residues in IL-1β). The overall homology and agonist/antagonist site-specific sequence Homologue clearly define SEQ ID NO: 5 as a protein modulator of the inflammatory response.

Example 7
Three Prime Extension of SEQ ID NO: 4

SEQ ID NO: 6 (FIG. 8) is an extension of the 3' end of the nucleic acid sequence of SEQ ID NO: 4. SEQ ID NO: 6 was obtained from a fetal skin cDNA library as described above for SEQ ID NO: 4.

Example 8
Isolation and Mapping of a Genomic Clone Corresponding to SEQ ID NOS: 1, 2, and 4

A human BAC genomic library (Research Genetics) was screened with gene-specific primers (273-D, 5'-CCCCACTGGATGGTGCTACTG-3' (SEQ ID NO: 15) which hybridizes at position 4533 to 4553 in the genomic sequence and 273-E, 5'-GGGMGAGATAGGAAAGGTAG-3' (SEQ ID NO: 16) which hybridizes at position 4849 to 4869) using a PCR based assay. Briefly, the gene specific primers were used to amplify BAC DNAs as templates using standard PCR conditions. BACs that produce a fragment of DNA corresponding to the predicted size were pursued. BAC393-I6 was isolated and its DNA sequenced with gene-specific primers derived from SEQ ID NO 2. The sequence (16403 bases in length) is shown in FIG. 9. The IL-1Ra coding sequence was found to be distributed over 5 exons. The splice donor and acceptor sites are shown below, along with intron and exon sizes.

| Exon | Splice Donor | Intron Size | Splice Acceptor | Exon Size |
|---|---|---|---|---|
| 1 | TCTGAGgtatgc (SEQ ID NO:17) | 172 bp | aaatagGGGAGT (SEQ ID NO:18) | 2(66 bp) |
| 2 | CTTCCGgtgagt (SEQ ID NO:19) | 1396 bp | tttcagAATGAA (SEQ ID NO:18) | 3(87 bp) |
| 3 | TTAAAGGTTGGT (SEQ ID NO:21) | 1189 bp | ccacagGTGAAG (SEQ ID NO:22) | 4(120 bp) |
| 4 | CTAGAGgtgaga (SEQ ID NO:23) | 204 bp | cggcagCCAGTG (SEQ ID NO:24) | |

Example 9
Expression of SEQ ID NO: 3 in E. coli

SEQ ID NO: 3 was expressed in E. coli by subcloning the entire coding region of the SEQ ID NO: 2 into a prokaryotic expression vector. The expression vector (pQE16) used was from the QIAexpression prokaryotic protein expression system (Qiagen). The features of this vector that make it useful for protein expression include: an efficient promoter (phage T5) to drive transcription; expression control provided by the lac operator system, which can be induced by addition of IPTG (isopropyl-β-D-thiogalactopyranoside), and an encoded His$_6$ tag. The latter is a stretch of 6 histidine amino acid residues which can bind very tightly to a nickel atom. The vector can be used to express a recombinant protein with a His$_6$ tag fused to its carboxyl terminus, allowing rapid and efficient purification using Ni-coupled affinity columns.

The coding sequence of SEQ ID NO: 2 (including the start codon but excluding the stop codon) was amplified using the PCR reaction primers AP1 (5'gaagatctatggtcctgagtggggccctg-3') (SEQ ID NO: 25) and AP2 (5'gaagatctgtcacactgctggaagtagaa-3') (SEQ ID NO: 26). Both primers have Bgl II restriction sites incorporated at the 5' ends for cloning purposes. The PCR fragment obtained upon amplification was restricted with Bgl II to generate staggered ends for ligating the insert into the vector. The pQE16 plasmid was digested with Bgl II and BamHI to remove a segment containing the dihydrofolate reductase coding sequence and also to generate the staggered ends compatible with those on the PCR fragment. The PCR fragment was ligated into the digested pQE16 vector to produce p16BB-273. The ligation was transformed by electroporation into electrocompetent E. coli cells (strain M15 [pREP4] from Qaigen), and the transformed cells were plated on ampicillin-containing plates. Colonies were screened for the correct insert in the proper orientation using a PCR reaction employing a gene-specific primer and a vector-specific primer. Positives were then sequenced to ensure correct orientation and sequence. To express SEQ ID NO: 3, a colony containing a correct recombinant clone was inoculated into L-Broth containing 100 μg/ml of ampicillin, 25 μg/ml of kanamycin, and the culture was allowed to grow overnight at 37° C. The saturated culture was then diluted 20-fold in the same medium and allowed to grow to an optical density at 600 nm of 0.5. At this point, IPTG was added to a final concentration of 1 mM to induce protein expression. The culture was allowed to grow for 5 more hours, and then the cells were harvested by centrifugation at 3000×g for 15 minutes.

The resultant pellet was lysed using a mild, nonionic detergent in 20 mM Tris HCl (pH 7.5) (B-PER™ Reagent from Pierce), or by sonication until the turbid cell suspension turned translucent. The lysate obtained was further purified using a nickel containing column (Ni-NTA spin column from Qiagen) under non-denaturing conditions. Briefly, the lysate was brought up to 300 mM NaCl and 10 mM imidazole and was centrifuged at 700×g through the spin column to allow the His-tagged recombinant protein to bind to the nickel column. The column was then washed twice with Wash Buffer (50 mM NaH$_2$PO$_4$, pH 8.0; 300 mM NaCl; 20 mM imidazole) and was eluted with Elution Buffer (50 mM NaH$_2$PO$_4$, ph 8.0; 300 mM NaCl; 250 mM imidazole). All the above procedures were performed at 4° C. The purified protein was checked with SDS-PAGE. A strong single band was observed, indicating a molecular weight of 16 kD, which is consistent with the predicted size of SEQ ID NO: 3.

Example 10

Use of SEQ ID NOS: 3 and 5

Medical Imaging

The novel Interleukin-1 receptor antagonist polypeptides of the invention are useful in medical imaging, e.g., imaging the site of infection, inflammation, and other sites having interleukin-1 receptor antagonist receptor molecules. See, e.g., Kunkel et al., U.S. Pat. No. 5,413,778. Such methods involve chemical attachment of a labeling agent, administration of the labeled Interleukin-1 receptor antagonist polypeptide to a subject in a pharmaceutically acceptable carrier, and imaging the labeled Interleukin-1 receptor antagonist polypeptide in vivo at the target site.

Pancreatitis

Acute edematous, necrotizing pancreatitis is induced in adult male Swiss mice weighing more than 35 grams using caerulein—an analog of cholecystokinin. Mice are divided into four groups with three of the groups receiving caerulein 50 mu g/kg by intraperitoneal (IP) injection in four doses over three hours as previously described. (Murayama et al., Arch Surg 1990;125:1570–1572; Tani et al., International J Pancreatology 1987;2:337–348; Schoenberg et al., Free Radical Biology & Medicine 1992;12:515–522; Heath et al., Pancreas 1993;66:41–45; Saluja et al., Amer Physiological Society 1985: G702-G710; Manso et al., Digestive Disease and Sciences 1992;37:364–368).

Group 1 is a control group (n-9) which received only IP saline injections. Group 2 (n=12) is an untreated disease control. Group 3 (n=12) received three injections (10 mg/kg/hr) starting one hour prior to induction of pancreatitis. Group 4 (n=12) received three injections (10 mg/kg/hr) starting one hour after induction of pancreatitis.

After a suitable time period, all animals are euthanized, the blood collected, and the pancreata surgically excised and weighed. Serum is assayed for amylase, lipase, IL-6, and TNF levels. Each pancreas is fixed, stained, and graded histologically in a blinded fashion for interstitial edema, granulocyte infiltration, acinar vacuolization, and acinar cell. Additionally, serum levels of Interleukin-1 receptor antagonist are determined, therefore allowing comparisons between dosage, serum level, systemic cytokine response, and degree of pancreatic damage.

Interleukin-6, Interleukin-1, Interleukin-1 receptor antagonist, and TNF are measured by commercially available ELISA kits (Genzyme Corp., Boston, Mass.). All specimens are run in triplicate. Serum levels of amylase and lipase are measured on a Kodak Ectachem 700 automated analyzer (Eastman Kodak Company, Rochester, N.Y.).

Histologic slides are prepared as is known in the art after rapid excision and subsequent fixation in 10% formalin. The tissues are paraffin embedded as is known in the art and then stained with Hematoxylin and Eosin in a standard fashion. These slides are examined and graded in a blinded fashion by a board certified pathologist.

Inhibition of Interleukin-1 Induced Cell Proliferation

Murine D10 T cells are obtained from the American Type Culture Collection (Rockville, Md.). Cells are maintained in Dulbecco's modified Eagle medium and Ham's F-12 medium (1:1) containing 10 mM HEPES buffer (pH 7.4) and 10% fetal bovine serum. All tissue culture reagents contained less than 0.25 ng/mL endotoxin as measured by the limulus amebocyte assay.

Murine D10 cells, an Interleukin-1 dependent T-cell line, are used to measure Interleukin-1 mitogenic activity. Cell proliferation in the present of Interleukin1 with and without the Interleukin-1 receptor antagonist polypeptides of the invention is assessed by incorporation of ( sup 3 H) thymidine as previously described (Bakouche, O., et al. J. Immunol. 138:4249–4255, 1987). In a preferred embodiment, antagonists and agonist of the Interleukin-1 receptor antagonist polypeptides of the invention are identified in this assay by adding the candidate compounds with the Interleukin-1 and Interleukin-1 receptor antagonist polypeptides of the invention and measuring the change in cell proliferation caused by the candidate compound.

Inhibition of Interleukin-1 Induced Cell Cytotoxicity

Inhibition of Interleukin-1 -induced cytotoxicity is studied using an appropriate cell line, such as, for example, A375 tumor cells plated at a density of 6000 cells per well in 96-well micro titer plates. After overnight attachment, Interleukin-1 (3–300 ng/mL) is added in the presence or absence of NAA or NMA. After cells are incubated for 3 days, ($^3$H) thymidine is added (1 mu Ci per well) for an additional 2 hours. Cells are harvested onto glass fiber disks (PHD Cell Harvested; Cambridge Technology, Inc., Watertown, Mass.) Disks are air dried overnight, and radioactivity is determined with a Model 1900TR Scintillation Counter (Packard Instrument Division, Downers Grove, Ill.)

Induction of Nitrite Synthesis in Smooth Muscle Cells

Aortic smooth muscle cells are cultured by explanting segments of the medial layer of aortas from adult male Fischer 344 rats. Aortas are removed aseptically and freed of adventitial and endothelial cells by scraping both the luminal and abluminal surfaces. Medial fragments are allowed to attach to Primaria 25-cm$^2$ tissue culture flasks (Becton-Dickinson, Lincoln Park, N.J.) which are kept moist with growth medium until cells emerged. Cultures are fed twice weekly with medium 199 containing 10% fetal bovine serum, 25 mM HEPES buffer (pH 7.4), 2 mM L-glutamine, 40 mu g/mL endothelial cell growth supplement (Biomedical Technologies, Inc., Stoughton, Mass.) and 10 mu g/ml gentamicin (GIBCO BRL, Grand Island, N.Y.). When primary cultures become confluent, they are passaged by trypsinization, and explants are discarded. For these studies, cells from passages 12–14 are seeded at 20,000 per well in 96-well plates and are used at confluence (60,000–80,000 cells per well). The cells exhibit the classic smooth muscle cell phenotype with hill and valley morphology, and they stain positively for smooth muscle actin.

Rat aortic smooth muscle cells are incubated with RPMI-1640 medium containing 10% bovine calf serum, 25 mM HEPES buffer 7.4), 2 mM glutamine, 80 U/mL penicillin, 80 mu g/mL streptomycin, 2 mu g/mL fungizone, and Interleukin-1, IFN-gamma, and various inhibitors. At the desired times, nitrite concentration in the culture medium is measured using the standard Griess assay (Green, L., et al. Anal. Biochem. 126:131–138, 1982) adapted to a 96-well micro titer plate reader (Gross, S. S., et al. Biochem. Biophys. Res. Commun. 178:823–829, 1991). Thus, 100 muL of Griess reagent (0.5% sulfanilic acid, 0.05% naphthalenediamine, and 2.5% phosphoric acid) is added to an equal volume of culture medium, and the OD$_{550}$ is measured and related to nitrite concentration by reference to a standard curve. The background OD$_{550}$ of medium incubated in the absence of cells is subtracted from experimental values.

Rat aortic smooth muscle cells are incubated with RPMI-1640 medium containing 10% bovine calf serum, 25 mM HEPES buffer (pH 7.4), 2 mM glutamine, 80 mu g/mL penicillin, 80 mu g/mL streptomycin, 2 mu g/mL fungizone, 30 mu g/mL lipopolysaccharide (*Escherichia coli* 0111:B4), and 50 U/mL IFN-y. Cells are harvested after 24 hours, and cytosol is prepared (Gross, S. S., et al. Biochem. Biophys. Res. Commun. 178:823–829, 1991). Cytosolic NO synthase activity is assayed by the Fe$^{2+}$-myoglobin method described previously (Gross, S. S., et al. Biochem. Biophys. Res. Commun. 178:823–829, 1991).

Alloreactivity Determined by Lymph Node Weight Gain

Experiments are conducted to show that systemic administration of the Interleukin-1 receptor antagonists polypeptides of the invention suppress a localized, T cell-dependent, immune response to alloantigen presented by allogeneic cells. Mice are injected in the footpad with irradiated, allogeneic spleen cells. The mice are then injected in the contralateral footpad with irradiated, syngeneic spleen cells. An alloreactive response (marked by proliferation of lymphocytes and inflammation) occurs in the footpad receiving the allogeneic cells, which can be measured by determining the increase in size and weight of the popliteal lymph node draining the site of antigen deposition relative to controls or by an increase in cellularity.

Specific pathogen free 8–12 week old BALB/c (H-2$^d$) and C57BL/6 (H-2$^b$) mice (Jackson Laboratory, Bar Harbor, Me.) are used in this experiment. 48 BALB/c mice are divided into 16 groups, each having 3 mice (unless otherwise indicated). Each group of mice received a different mode of treatment. On day 0 the left footpads of all mice are injected intracutaneously with 10$^7$ irradiated (2500R), allogeneic spleen cells from C57BL/6 mice in 50 µl of RPMI-1640 (Gibco) as antigen and the right contralateral footpads of the same mice are injected with 10$^7$ irradiated (2500R), syngeneic spleen cells from BALB/c mice.

Seven days after antigen administration, the mice are sacrificed and the popliteal lymph nodes (PLN) are removed from the right and left popliteal fossa by surgical dissection. Lymph nodes are weighed and the results expressed as the difference (DELTA) in weight (mg) of the lymph node draining the site of allogeneic cell injection and the weight of the node draining the syngeneic cell injection site. Lymph nodes draining the syngeneic cell injection site weighed approximately 1 mg, regardless of whether they are obtained from mice treated with MSA or Interleukin-1 receptor antagonist polypeptides of the invention, and did not differ significantly in weight from nodes obtained from mice given no cell injection.

Suppression of Organ Graft Rejection In vivo

Neonatal C57BL/6 (H-2$^b$) hearts are transplanted into the ear pinnae of adult BALB/c (H-2$^d$) recipients utilizing the method of Fulmer et al., Am. J. Anat. 113:273, 1963, modified as described by Trager et al., Transplantation 47:587, 1989, and Van Buren et al., Transplant Proc. 15:2967, 1983. Survival of the transplanted hearts is assessed by visually inspecting the grafts for pulsatile activity. Pulsatile activity is determined by examining the ear-heart grafts of anesthetized recipients under a dissecting microscope with soft reflected light beginning on day 5 or 6 post transplant. The time of graft rejection is defined as the day after transplantation on which contractile activity ceases.

Recipient mice are transplanted on day 0 and injected with either interleukin-1 receptor antagonist polypeptides of the invention plus MSA (mouse serum albumin, 100 ng) or with MSA alone on days 0 through 6, alternating i.p. and s.c. routes. In a second heart transplant experiment, the mice are injected with MSA alone on days 0 through 2, i.p. route only.

Suppression of Inflammatory Arthritis 20 rats are divided into 4 groups, designated Groups G–J, each having 5 rats. All rats are immunized by subcutaneous injection. On day 21 following immunization with mBSA, an inflammatory arthritis response is elicited. On the same day, a negative control group is injected with a 0.2 ml volume of saline. Groups are injected with increasing amounts of Interleukin-1 receptor antagonist polypeptides of the invention. Interleukin-1 is injected in one group as a positive control. The diameter of the largest region of the treated joints is measured using a caliper on days 2, 4, 6 and 8 relative to day 0 intra-articular injection of antigen.

Example 11

Isolation and Mapping of a Genomic Clone Corresponding to SEQ ID NO: 6

FIGS. 10A–C show a genomic clone (SEQ ID NO: 8) which is an extension of the genomic sequence presented in FIG. 9A–C (SEQ ID NO: 7). SEQ ID NO: 8 includes the extended sequence (three prime untranslated) shown in SEQ ID NO: 6. The isolation of this genomic clone (SEQ ID NO: 8) was the same as described in Example 8. The sequence is 7,605 nucleotides in length) is shown in FIGS. 10A–C. The organization of the exons for this clone is described below.

| Exon | Nucleotide Range of Exon | Intronic/Exonic Sequences*** |
|---|---|---|
| Exon 1E* | 1308–1383 | ctgtagGCCTGG------AAAAAGgtaagg(SEQ ID NOS:27 & 28) |
| Exon 1M** | 1780–1890 | cctcagGTCCTG------TCTGAGgtatgc(SEQ ID NOS:29 & 17) |
| Exon 2 | 2061–2116 | aaatagGGGAGT------CTTCCGgtgagt(SEQ ID NOS:18 & 19) |
| Exon 3 | 3504–3589 | tttcagAATGAA------TTAAAGgttggt(SEQ ID NOS:20 & 21) |
| Exon 4 | 4777–4905 | ccacagGTGAAG------CTAGAGgtgaga(SEQ ID NOS:22 & 23) |
| Exon 5 | 5107–7395 | cggcagCCAGTG------AAAGAG(SEQ ID NO:24) |

*Exon 1 E, exon 1 in epidermoid carcinoma cell line A431
**Exon 1M, exon 1 in activated macrophage cell line THP1
***Intronic sequences shown in lowercase, exonic sequences shown in uppercase.

Example 12
Recombinant Protein Expression and Purification

An expression vector placing the Interleukin-1 Receptor Antagonist coding sequence (SEQ ID NO: 3) without the N terminal hydrophobic sequence was placed after the $His_6$ tag (a stretch of 6 histidine amino acid residues) and express tags (antibody tag) in the pRSET vector (conferring ampicillin resistance). The $His_6$ tag fused to its amino terminus of a recombinant protein allows rapid and efficient purification using Ni-coupled affinity columns.

This construct was transformed into *E. coli* (BL-21 with the pLYS plasmid conferring chloramphenicol resistance) and expression was induced using IPTG (1 mM final). Bacterial pellet was suspended in 50 mM Tris pH.7.5. Sonic dismembrator was employed to lyse cells in the presence of 1 mg/ml of lysozyme (10 ml of buffer per gram of wet cells). Cell debris was removed by centrifugation. Imidazole was added at 10 mM final concentration with 100 mM NaCl. The extract was loaded on a Nickel chelate column. The protein was eluted off the column with a linear gradient of imidazole from 50 mM to 300 mM. After the peak was collected, it was desalted on a sephadex G-25 column into 20 mM sodium phosphate buffer. Protein was loaded onto a Q-sepharose column and eluted off the gradient from 0–350 mM NaCl. The final recombinant protein was filter sterilized and stored at −20° C.

Example 13
Binding of the Interleukin-1 Receptor Antagonist to the Interleukin-1 Receptor A cell binding assay was carried out to demonstrate that Interleukin-1 Receptor Antagonist of the invention binds to the Interleukin-1 receptor. Briefly, cell binding of the recombinant protein (see Example 12) with and without the presence of 100 fold greater amounts of non tagged Interleukin-1 βeta (IL-1β) ligand was analyzed by using fluorescent antibodies specific for the express tag in the Interleukin-1 Receptor Antagonist recombinant protein on the fluorescent activated cell sorter (FACS). In each reaction, $10^6$ cells NHDF (normal human dermal fibroblasts) were resuspended in 100 ul of FACS buffer (distilled PBS and 3% calf serum and 0.01% azide). Cell binding was done by adding 5 nM recombinant Interleukin-1 Receptor Antagonist in 100 μl cell suspension and as a competition in one reaction, 500 nM of recombinant IL-1β was also added. The cells were incubated on ice for 1 hr. The cells were pelleted, 200 μl of 0.2 mM BS3 (crosslinker) was added, and the cells were kept on ice for 30 min. Next, 10 μl 1 M Tris pH 7.5 was added and the cells were incubated for 15 minutes on ice. The cells were pelleted, washed 1 time in FACS buffer, resuspended in 100 μl volume of FACS buffer and 2 μl primary antibody (anti-express tag antibody 1 mg/ml) was added, and incubated on ice for 30 min. The cells were pelleted, washed with FACS buffer, and resuspended in FACS buffer (100 μl volume). The secondary antibody (phycoerythrin conjugated) 2 ul of anti-mouse Ig (1 mg/ml) was added and the cells were incubated for 30 minutes on ice. The cells were again pelleted, washed two times with FACS buffer, resuspended in 0.5 ml FACS buffer and analyzed on FACS. A shift in the fluorescence was observed in the cells treated with the recombinant tagged Interleukin-1Hy1 Receptor Antagonist. This binding was shown to be specific, as is was competed off with the non-tagged IL-1β protein. These results indicate binding of the Interleukin-1 Receptor Antagonist protein of the invention to the IL-1 receptor.

Example 14
Confirmation of IL-1 Antagonist Activity

II-1 antagonist activity was determined using a prostaglandin $E_2$ ($PGE_2$) based assay as follows. NHDF cells were plated at $2\times10^4$ cells per well in a 96-well plate 24 hours before the assay. The cells were then treated with 25 pg/ml recombinant human IL-1β for seven hours. To study the inhibition of IL-1β stimulated $PGE_2$ release by IL-1Hy1, the cells were pretreated with different amounts of IL-1Hy1 for two hours before the addition of IL-1β. The supernatants were then collected and cell debris was removed by centrifugation. The amount of $PGE_2$ in the supernatants was determined by ELISA using the $PGE_2$ assay system (R & D Systems) according to the manufacturer's directions.

When NHDF cells were treated with IL-1Hy1 alone, no $PGE_2$ activity was measured. To determine whether IL-1Hy1 could inhibit IL-1β induced $PGE_2$ production, the cells were pretreated with different concentrations of IL-1Hy1 before stimulation with IL-1β. IL-1Hy1 was able to inhibit IL-1β induced $PGE_2$ production in a dose dependent fashion as shown in FIG. 11. These results indicate that IL-1Hy1 acts in a manner similar to IL-1ra in vitro, indicating that they have overlapping functions.

Example 15
Inhibition of IL-1β Induced IL-6 Production

Inhibition of Interleukin-1β induced IL-6 production was studied using human endothelial cells from umbilical vein (Huvec). Huvec cells were seeded at $2\times10^4$ cells per well in a 96-well plate the day before cell stimulation. On the day of stimulation, cells were washed once with fresh medium (F12 medium with 100 µg/ml heparin, 50 µg/ml endothelial growth supplement and 10% fetal bovine serum) and replated with 200 µl of fresh medium [without supplements] in each well. The Huvec cells were then stimulated with 100 pg/ml (final volume) of IL-1β. Although this assay was done with IL-1β, any cytokine of interest can be used. To test IL-6 inhibition, different concentrations of IL-1Hy1 (ranging from 10× to 1000× the concentration of IL-1β) or IL-1ra (ranging from 10× to 1000× IL-1 β concentration) were added to the wells with the IL-1β.

After 16 hours of cell stimulation, the culture plate was spun for five minutes at 4000 rpm to remove cell debris. 100 µl of the supernatant was removed to test for the presence of IL-6 using a human IL-6 immunoassay kit (R&D Systems) according to the manufacturer's instructions.

IL-1Hy1 partially inhibited IL-1β-stimulated IL-6 production in a dose-dependent manner. In view of the fact that IL-6 blocks production of tumor necrosis factor (TNF), a pro-inflammatory cytokine, the fact that IL-1Hy1 only partially inhibits of IL-6 production by IL1-Hy1 may be beneficial in the treatment of inflammatory disease states with IL1-Hy1.

The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims. All references cited within the body of the instant specification are hereby incorporated by reference in their entirety.

What is claimed is:

1. An isolated antibody or fragment thereof which specifically binds to a human polypeptide having the amino acid sequence of SEQ ID NO: 5, and which does not bind to non-human polypeptides.

2. The antibody of claim 1 which is a monoclonal antibody.

3. A hybridoma which produces the monoclonal antibody of claim 2.

4. The antibody fragment of claim 1 which is a fragment of a monoclonal antibody.

5. The antibody of claim 1 which is a polyclonal antibody.

6. The antibody fragment of claim 1 which is a fragment of a polyclonal antibody.

7. The antibody or antibody fragment of claim 1 which is a humanized antibody or fragment thereof.

8. The antibody or antibody fragment of claim 1 which is a human antibody or fragment thereof.

9. The antibody of claim 1 which comprises a detectable label.

10. The antibody of claim 9 wherein the detectable label is a radioisotope, affinity label, enzymatic label, fluorescent label or paramagnetic moiety.

11. A kit comprising (a) the antibody or antibody fragment of claim 1 and (b) a polypeptide having the amino acid sequence of SEQ ID NO: 5 or a fragment thereof which is immunologically reactive with said antibody or antibody fragment.

12. A kit comprising (a) the antibody or antibody fragment of claim 1 and (b) a wash reagent or a reagent capable of detecting the presence of a bound antibody.

13. A composition comprising the antibody or antibody fragment of claim 1 and a pharmaceutically acceptable carrier, excipient or diluent.

14. A method of detecting the presence of an IL-1 Hy1 polypeptide having the amino acid sequence of SEQ ID NO: 5 or a fragment thereof in a cell, tissue or fluid sample comprising contacting said cell, tissue or fluid sample with an antibody or fragment of claim 10 under conditions which permit the formation of an antibody/polypeptide complex and detecting the presence of an antibody/polypeptide complex, wherein the presence of the antibody/polypeptide complex indicates the presence of an IL-1 Hy1 polypeptide.

* * * * *